(12) United States Patent
Simon et al.

(10) Patent No.: US 10,350,411 B2
(45) Date of Patent: Jul. 16, 2019

(54) DEVICES AND METHODS FOR TREATING MEDICAL DISORDERS WITH EVOKED POTENTIALS AND VAGUS NERVE STIMULATION

(71) Applicant: ElectroCore, LLC, Basking Ridge, NJ (US)

(72) Inventors: Bruce J. Simon, Mountain Lakes, NJ (US); Joseph P. Errico, Warren, NJ (US)

(73) Assignee: Electrocore, Inc., Basking Ridge, NJ (US)

( * ) Notice: Subject to any disclaimer, the term of this patent is extended or adjusted under 35 U.S.C. 154(b) by 0 days.

(21) Appl. No.: 15/232,158

(22) Filed: Aug. 9, 2016

(65) Prior Publication Data

US 2016/0346542 A1     Dec. 1, 2016

Related U.S. Application Data

(60) Division of application No. 14/212,992, filed on Mar. 14, 2014, now Pat. No. 9,427,581, which is a
(Continued)

(51) Int. Cl.
*A61B 5/00* (2006.01)
*A61N 1/04* (2006.01)
(Continued)

(52) U.S. Cl.
CPC ...... *A61N 1/36021* (2013.01); *A61B 5/04886* (2013.01); *A61B 5/4035* (2013.01);
(Continued)

(58) Field of Classification Search
CPC ............ A61N 1/36014; A61N 1/36114; A61N 1/0456
(Continued)

(56) References Cited

U.S. PATENT DOCUMENTS 3,590,810 A    7/1971   Kopecky
4,196,737 A    4/1980   Bevilacqua
(Continued)

FOREIGN PATENT DOCUMENTS

EP      2777764     8/2015
KR    101242190    3/2013
(Continued)

OTHER PUBLICATIONS

Greicius et al., Functional connectivity in the resting brain: A network analysis of the default mode hypothesis, PNAS, Jan. 2003, vol. 100, No. 1, pp. 253-258.
(Continued)

*Primary Examiner* — Amanda K Hulbert
*Assistant Examiner* — Philip C Edwards
(74) *Attorney, Agent, or Firm* — Dentons US LLP

(57) ABSTRACT

Devices, systems and methods for treating medical disorders, such as migraine or other primary headaches, or fibromyalgia, by noninvasive electrical stimulation of a vagus nerve, used in conjunction with the measurement of evoked potentials (EPs). The system comprises a stimulator that is applied to the surface of the patient's neck to apply electrical impulses sufficient to stimulate a cervical vagus nerve, scalp electrodes that are used to measure EPs that are evoked by that stimulation, feedback or biofeedback circuits to vary the stimulation based upon EP characteristics, and other sensory stimulation modalities that produce EPs. The system is preferably used to optimize the placement of the stimulator, to test whether a patient is a suitable candidate for treatment using vagus nerve stimulation, and to select the stimulation parameters that optimized acute or chronic treatment, e.g., by correcting an EP habituation deficit.

27 Claims, 16 Drawing Sheets

Related U.S. Application Data continuation-in-part of application No. 13/872,116, filed on Apr. 28, 2013, now Pat. No. 9,254,383.

(51) Int. Cl.

| | |
|---|---|
| *A61N 1/36* | (2006.01) |
| *A61N 1/40* | (2006.01) |
| *A61B 5/024* | (2006.01) |
| *A61B 90/00* | (2016.01) |
| *A61B 5/0488* | (2006.01) |
| *A61N 1/00* | (2006.01) |

(52) U.S. Cl.
CPC .......... *A61B 5/4041* (2013.01); *A61B 5/4803* (2013.01); *A61B 5/4836* (2013.01); *A61B 5/7264* (2013.01); *A61B 5/7267* (2013.01); *A61N 1/0456* (2013.01); *A61N 1/36014* (2013.01); *A61B 5/02405* (2013.01); *A61B 2090/3941* (2016.02); *A61N 1/40* (2013.01)

(58) Field of Classification Search
USPC ......................................................... 607/45
See application file for complete search history.

(56) References Cited

U.S. PATENT DOCUMENTS

| | | | |
|---|---|---|---|
| 4,989,605 A | 2/1991 | Rossen | |
| 5,109,847 A | 5/1992 | Liss et al. | |
| 5,458,141 A | 10/1995 | Neil | |
| 5,487,759 A | 1/1996 | Bastyr et al. | |
| 5,782,874 A | 7/1998 | Loos | |
| 5,899,922 A | 5/1999 | Loos | |
| 5,983,131 A | 11/1999 | Weaver et al. | |
| 6,341,236 B1 | 1/2002 | Osorio et al. | |
| 6,463,327 B1 | 10/2002 | Lurie et al. | |
| 6,587,719 B1 | 7/2003 | Barrett et al. | |
| 6,610,713 B2 | 8/2003 | Tracey | |
| 6,631,297 B1 | 10/2003 | Mo | |
| 7,561,918 B2 * | 7/2009 | Armstrong ......... | A61N 1/36071 607/28 |
| 7,734,340 B2 | 6/2010 | De Ridder | |
| 7,797,041 B2 | 9/2010 | Libbus et al. | |
| 2002/0099417 A1 | 7/2002 | Naritoku et al. | |
| 2002/0183237 A1 | 12/2002 | Puskas | |
| 2002/0183804 A1 | 12/2002 | Malaney et al. | |
| 2003/0212311 A1 | 11/2003 | Nova et al. | |
| 2004/0073271 A1 | 4/2004 | Harry et al. | |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0065574 A1 | 3/2005 | Rezai | |
| 2005/0113630 A1 | 5/2005 | Fox et al. | |
| 2005/0137644 A1 | 6/2005 | Boveja et al. | |
| 2005/0187590 A1 | 8/2005 | Boveja et al. | |
| 2005/0216062 A1 | 9/2005 | Herbst | |
| 2005/0267544 A1 | 12/2005 | Lee et al. | |
| 2006/0074284 A1 | 4/2006 | Juola et al. | |
| 2006/0074450 A1 | 4/2006 | Boveja et al. | |
| 2006/0100668 A1 | 5/2006 | Ben-David et al. | |
| 2006/0100671 A1 | 5/2006 | Ridder | |
| 2006/0173510 A1 | 8/2006 | Besio et al. | |
| 2006/0178703 A1 | 8/2006 | Huston et al. | |
| 2007/0027496 A1 | 2/2007 | Parnis et al. | |
| 2007/0038264 A1 | 2/2007 | Jaax et al. | |
| 2007/0106337 A1 | 5/2007 | Errico et al. | |
| 2007/0123952 A1 | 5/2007 | Strother et al. | |
| 2007/0142886 A1 | 6/2007 | Fischell et al. | |
| 2007/0150006 A1 | 6/2007 | Libbus et al. | |
| 2007/0156182 A1 | 7/2007 | Castel et al. | |
| 2007/0179557 A1 * | 8/2007 | Maschino ......... | A61N 1/36071 607/45 |
| 2007/0276449 A1 | 11/2007 | Gunter et al. | |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0077192 A1 | 3/2008 | Harry et al. | |
| 2008/0114199 A1 | 5/2008 | Riehl et al. | |
| 2008/0132964 A1 | 6/2008 | Cohen et al. | |
| 2008/0177190 A1 | 7/2008 | Libbus et al. | |
| 2008/0208266 A1 * | 8/2008 | Lesser ............... | A61N 1/36114 607/2 |
| 2008/0306325 A1 | 12/2008 | Burnett et al. | |
| 2009/0112283 A1 | 4/2009 | Kriksunov et al. | |
| 2009/0132018 A1 | 5/2009 | DiUbaldi et al. | |
| 2009/0157149 A1 | 6/2009 | Wahlgren et al. | |
| 2009/0234417 A1 | 9/2009 | Pastena et al. | |
| 2009/0234419 A1 | 9/2009 | Maschino et al. | |
| 2009/0240297 A1 | 9/2009 | Shavit et al. | |
| 2009/0287035 A1 | 11/2009 | Dietrich et al. | |
| 2010/0030299 A1 | 2/2010 | Covalin | |
| 2010/0152794 A1 | 6/2010 | Radivojevic et al. | |
| 2010/0286553 A1 | 11/2010 | Feler et al. | |
| 2011/0046432 A1 | 2/2011 | Simon et al. | |
| 2011/0152967 A1 | 6/2011 | Simon et al. | |
| 2011/0213295 A1 | 9/2011 | Henley et al. | |
| 2011/0224749 A1 | 9/2011 | Ben-David et al. | |
| 2011/0230701 A1 | 9/2011 | Simon et al. | |
| 2012/0029601 A1 | 2/2012 | Simon et al. | |
| 2012/0283697 A1 | 11/2012 | Kim et al. | |
| 2012/0303080 A1 | 11/2012 | Ben-David et al. | |
| 2013/0006322 A1 | 1/2013 | Tai | |
| 2013/0060304 A1 | 3/2013 | LaTendresse et al. | |
| 2013/0245486 A1 | 9/2013 | Simon et al. | |
| 2014/0005743 A1 | 1/2014 | Giuffrida et al. | |
| 2015/0165226 A1 | 6/2015 | Simon et al. | |
| 2015/0190637 A1 | 7/2015 | Simon et al. | |

FOREIGN PATENT DOCUMENTS

| | | |
|---|---|---|
| WO | WO 1993/01862 | 2/1993 |
| WO | WO2005/007120 | 1/2005 |
| WO | WO2007/092062 | 8/2007 |
| WO | WO2008/042902 | 4/2008 |
| WO | WO2007/058780 | 5/2008 |
| WO | WO 2009/021080 | 2/2009 |
| WO | WO 2009/064641 | 5/2009 |
| WO | WO 2009/135693 | 11/2009 |
| WO | WO2013066135 | 5/2013 |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

International Search Report and Written Opinion dated Aug. 25, 2015 in related Application No. PCT/US15/31847 filed May 20, 2015 (10 pages).

(56) References Cited

OTHER PUBLICATIONS

Europe Office Action dated Apr. 24, 2018 in related Application No. 15796247.3 filed May 20, 2015 (6 pages).
KR101242190 dated Mar. 25, 2013, Espacenet computer generated English translation (11 pages).
Europe Office Action dated Jul. 26, 2018 in related Application No. 11818591.7, filed Aug. 12, 2011 (8 pages).

* cited by examiner

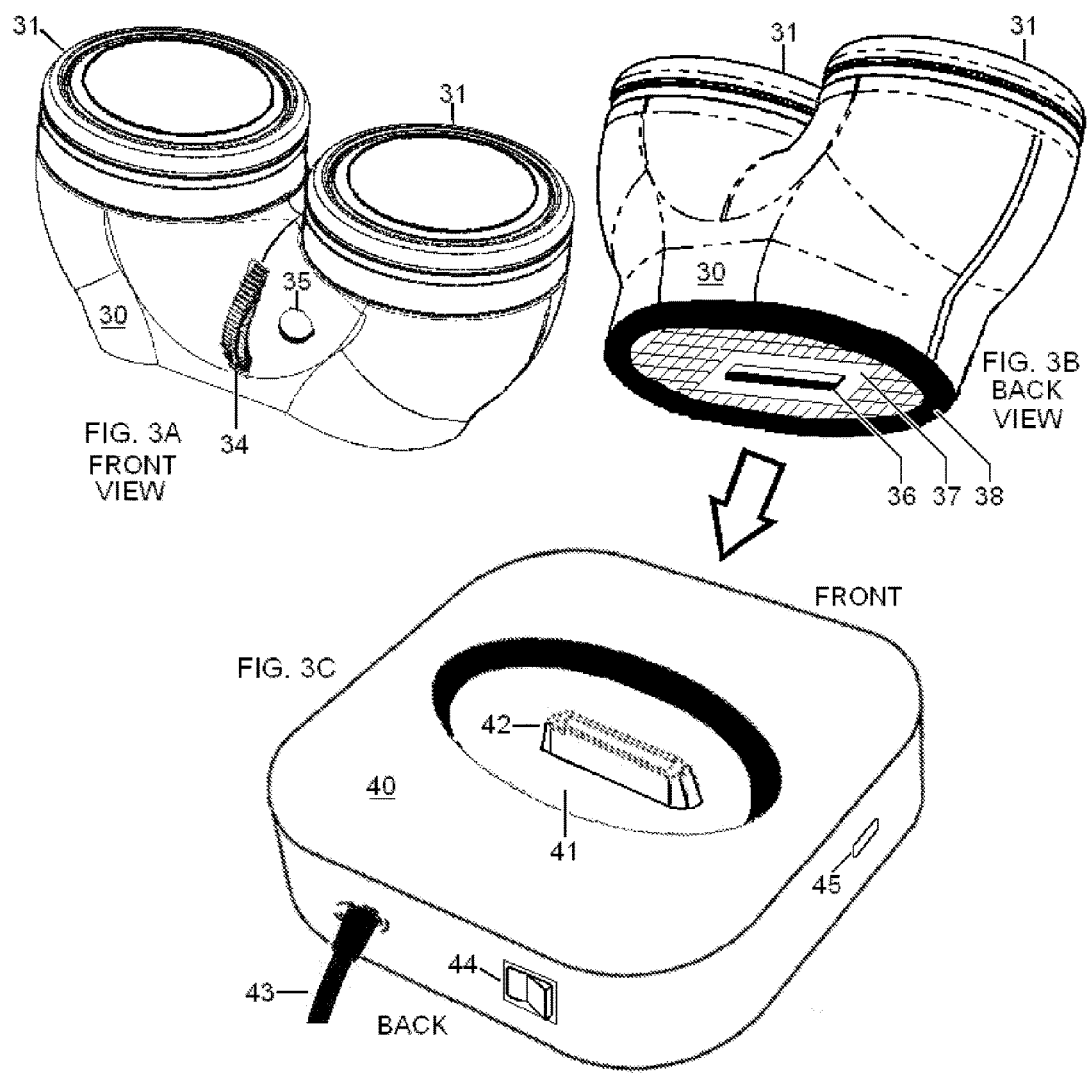

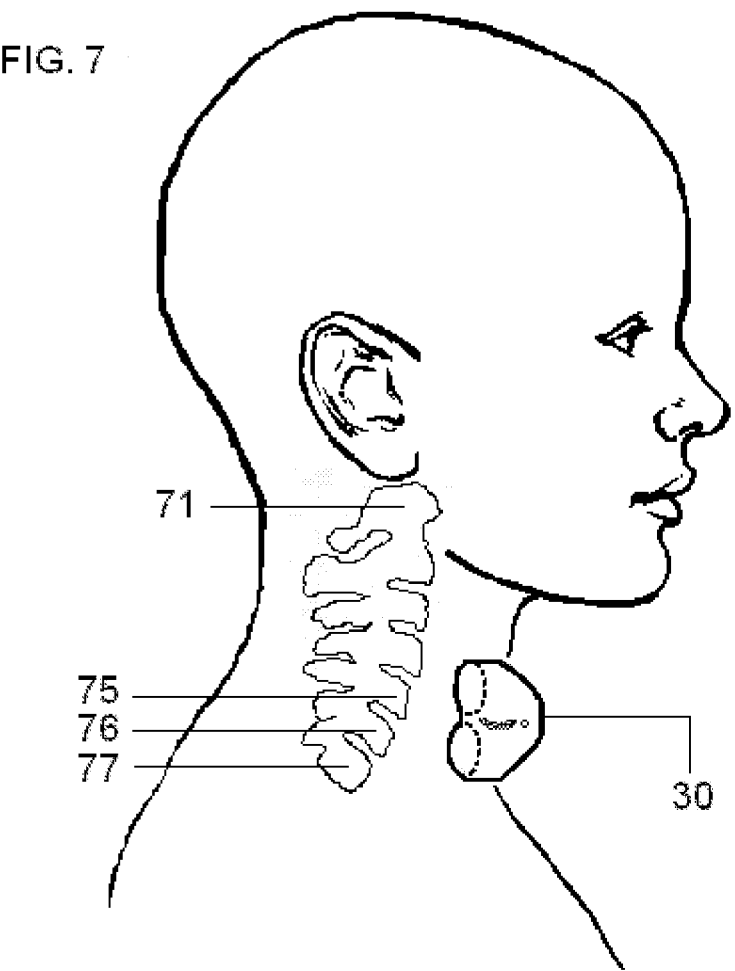

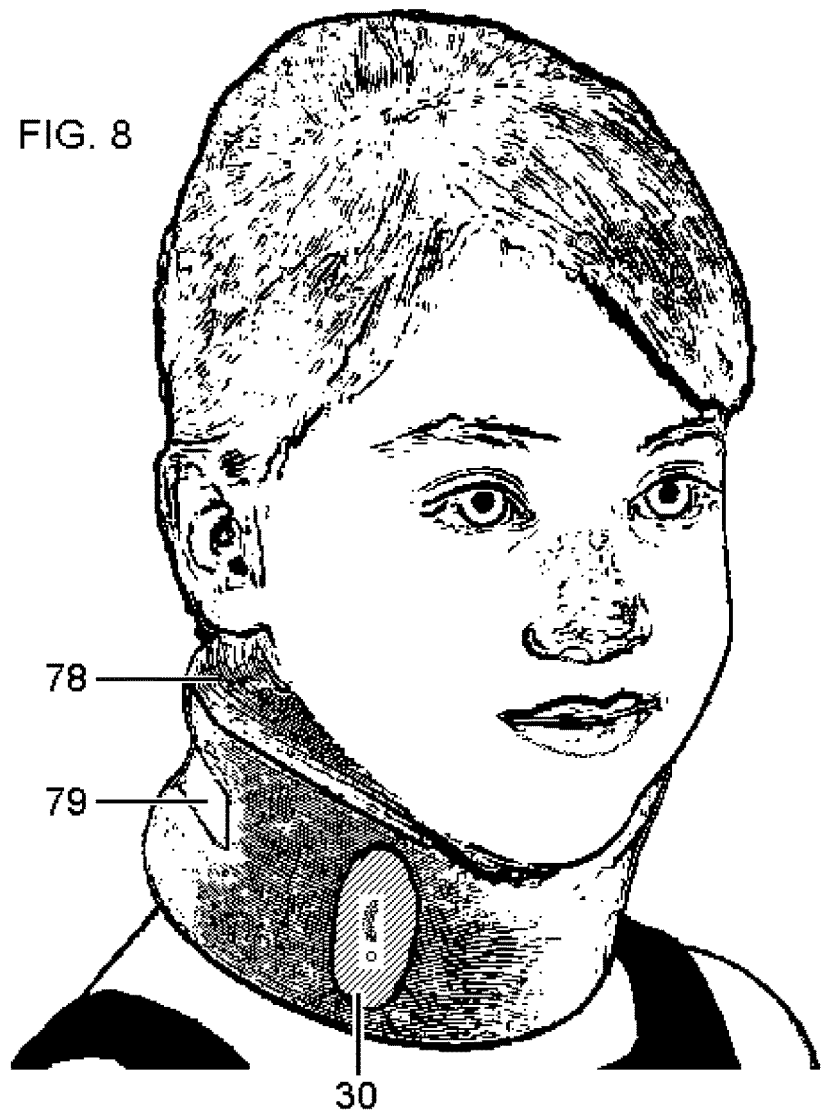

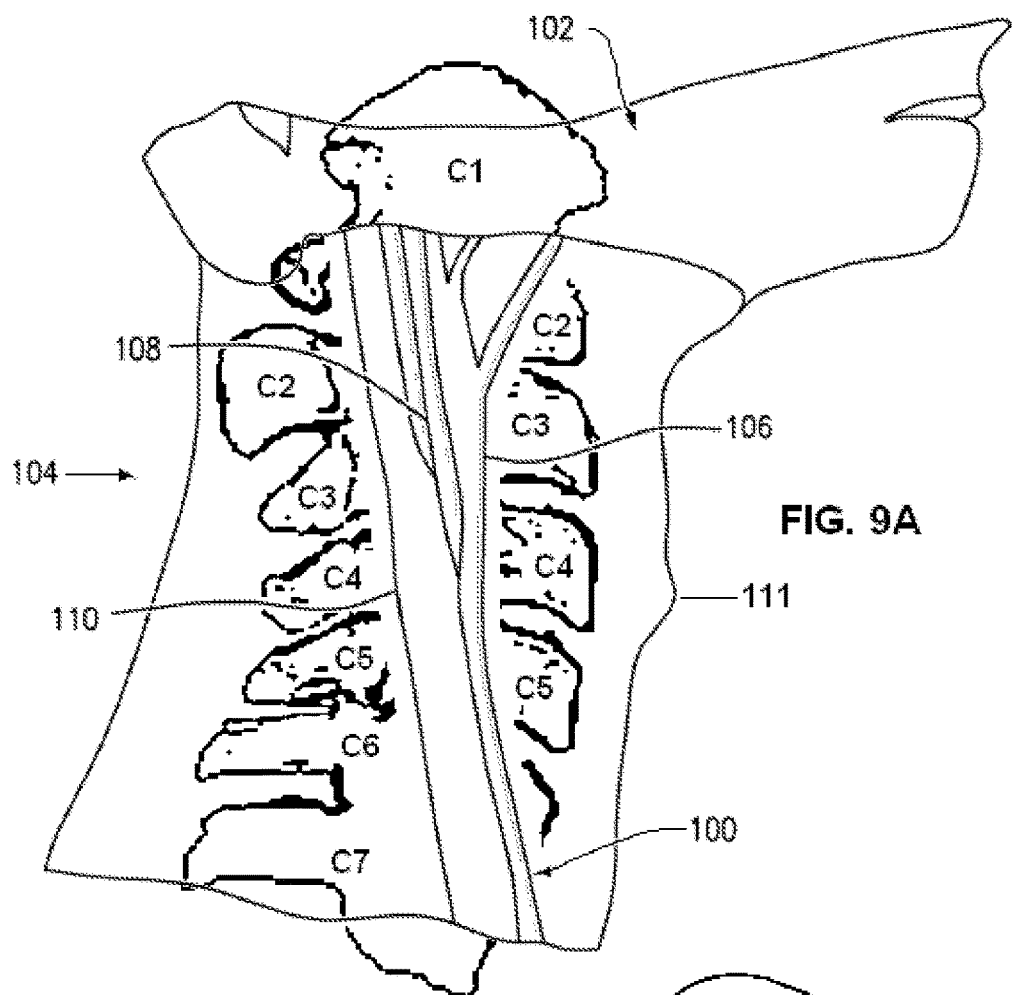
FIG. 9A
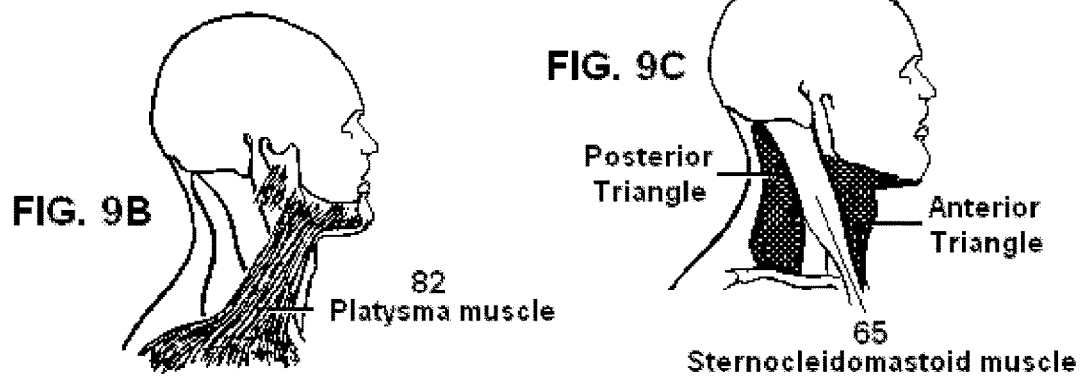
FIG. 9B
82 Platysma muscle
FIG. 9C
Posterior Triangle
Anterior Triangle
65 Sternocleidomastoid muscle

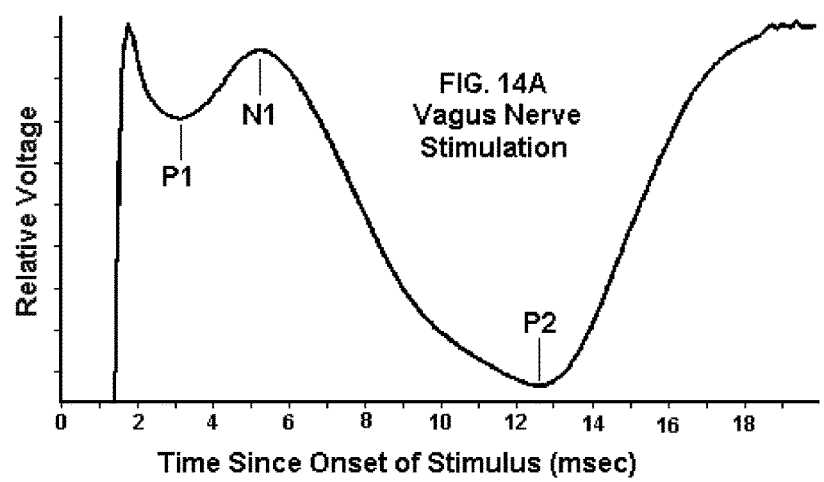
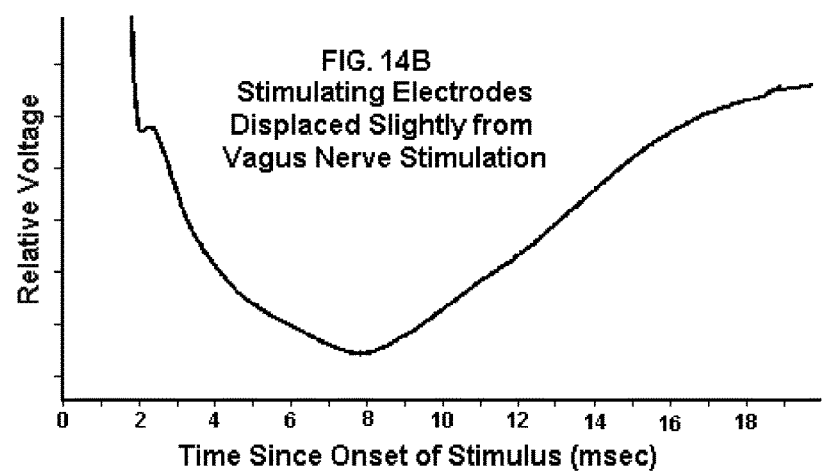

DEVICES AND METHODS FOR TREATING MEDICAL DISORDERS WITH EVOKED POTENTIALS AND VAGUS NERVE STIMULATION

CROSS REFERENCE TO RELATED APPLICATIONS

This application is a Divisional of U.S. application Ser. No. 14/212,992 filed 14 Mar. 2014; which is a Continuation in Part of U.S. application Ser. No. 13/872,116 filed 28 Apr. 2013; each of which is herein fully incorporated by reference for all purposes.

BACKGROUND

The field of the present invention relates to the delivery of energy impulses (and/or energy fields) to bodily tissues for therapeutic purposes. The invention relates more specifically to the use of non-invasive or minimally-invasive electrical stimulation of the vagus nerve in a patient's neck in order to treat various medical disorders, such as primary headache (e.g., migraine) or fibromyalgia.

Migraine headache is a type of primary headache, i.e., a headache that does not occur secondarily to another cause. Migraine is a highly disabling disorder, with an annual prevalence of 6-9% among men and 15-17% among women. Approximately 20-30% of migraine sufferers (migraineurs) experience an aura, ordinarily a visual aura. The aura typically lasts for 5 minutes to an hour, during which time the patient experiences sensations such as moving zig-zag flashes of light, blind spots or tingling in the hand or face. The migraine headache typically passes through the following stages: prodrome, aura, headache pain, and postdrome. All these phases do not necessarily occur, and there is not necessarily a distinct onset or end of each stage, with the possible exception of the aura. An interictal period follows the postdrome, unless the postdrome of one migraine attack overlaps the prodrome of the next migraine attack. The pain is often reported as starting in the occipital/neck regions, later becoming frontotemporal. It is throbbing and aggravated by physical effort [Bert B. VARGAS, David W. Dodick. The Face of Chronic Migraine: Epidemiology, Demographics, and Treatment Strategies. Neurol Clin 27 (2009) 467-479; Peter J. GOADSBY, Richard B. Lipton, Michel D. Ferrari. Migraine—Current understanding and treatment. N Engl J Med 346 (4, 2002): 257-270; Stephen D SILBERSTEIN. Migraine. LANCET 363 (2004):381-391].

Signs of sensory hyper-excitability often make their debut during the premonitory or prodromal phase of a migraine headache, which later accompany the headache phase. The hypersensitivity to external stimuli may manifest itself as photophobia, phonophobia, hyperosmia and cutaneous allodynia, corresponding respectively to heightened sensitivity to light, sound, odor, and touch (particularly of the scalp and face). Therefore, migraineurs often seek a dark, quiet place during the attack. In the interictal period between attacks, migraineurs also show abnormal processing of sensory information that is apparently due to dysfunctional regulation of cortical excitability [COPPOLA G, Pierelli F, Schoenen J. Is the cerebral cortex hyperexcitable or hyperresponsive in migraine? Cephalalgia 27(2007):1427-1439; AURORA S K, Wilkinson F. The brain is hyperexcitable in migraine. Cephalalgia 27(2007):1442-1445; COPPOLA G, Schoenen J. Cortical excitability in chronic migraine. Curr Pain Headache Rep 16(2012):93-100; MAGIS D, Vigano A, Sava S, d'Elia T S, Schoenen J, Coppola G. Pearls and pitfalls: electrophysiology for primary headaches. Cephalalgia 33(8,2013):526-539].

Pharmacological administration of triptans is currently the most effective treatment for acute migraine headaches (Sumatriptan, Zolmitriptan, Naratriptan, Rizatriptan, Eletriptan, Almotriptan, and Frovatriptan). However, only 30-40% of migraineurs are pain-free two hours after the administration of triptans. Of those who do respond, one in three will experience a migraine recurrence within 24 hours. Furthermore, because triptans constrict cranial blood vessels through activation of serotonin 5-HT1B receptors, as a side effect they may also cause vasoconstriction of coronary vessels. Switching to a different triptan might benefit some non-responders, but for many such migraineurs, non-migraine-specific rescue drugs that have significant side effects may be the last and potentially ineffective option (opioids, neuroleptics, and/or corticosteroids). Accordingly, migraine treatment methods are needed that are more effective than triptan pharmaceuticals but that do not exhibit significant side effects. Furthermore, more effective treatment methods are needed to reduce the likelihood that a migraine attack will occur [Stephen D Silberstein. Migraine. Lancet 363 (2004):381-391; Peter J GOADSBY, Till Sprenger. Current practice and future directions in the prevention and acute management of migraine. Lancet Neurol 9(2010): 285-98; Joel R. SAPER, Alvin E. Lake III, Philip A. Bain, et al. A Practice Guide for Continuous Opioid Therapy for Refractory Daily Headache: Patient Selection, Physician Requirements, and Treatment Monitoring. Headache 50(2010): 1175-1193].

Non-pharmacological treatments of migraine headaches have a long history, as an alternative or complement to treatment with drugs. Such non-parmacological treatments include behavioral therapy, physical treatments such as massage, phototherapy, acupuncture, greater occipital nerve blockade and trigger point injections, electrical stimulation with implanted electrodes in lieu of occipital or auriculotemporal nerve blockade, magnetic stimulation just below the occipital bone, and surgery [Peter J. KOEHLER and Christopher J. Boes. A history of non-drug treatment in headache, particularly migraine. Brain 133(2010): 2489-2500].

Another non-pharmacological treatment that is particularly relevant to the present invention is the electrical stimulation of the migraineur's vagus nerve. Vagus nerve stimulation (VNS) was developed initially for the treatment of partial onset epilepsy and was subsequently developed for the treatment of depression and other disorders. The left vagus nerve is ordinarily stimulated at a location within the neck by first implanting an electrode about the vagus nerve during open neck surgery and by then connecting the electrode to an electrical stimulator circuit (a pulse generator). The pulse generator is ordinarily implanted subcutaneously within a pocket that is created at some distance from the electrode, which is usually in the left infraclavicular region of the chest. A lead is then tunneled subcutaneously to connect the electrode assembly and pulse generator. The patient's stimulation protocol is then programmed using a device (a programmer) that communicates with the pulse generator, with the objective of selecting electrical stimulation parameters that best treat the patient's condition (pulse frequency, stimulation amplitude, pulse width, etc.) [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al; U.S. Pat. No. 5,299,569 entitled Treatment of neuropsychiatric disorders by nerve stimulation, to WER- NICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009):1042-1060; GROVES D A, Brown V J. Vagal nerve stimulation: a review of its applications and potential mechanisms that mediate its clinical effects. Neurosci Biobehav Rev 29(2005):493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (3,2008):E9, pp. 1-4; ANDREWS, R. J. Neuromodulation. I. Techniques-deep brain stimulation, vagus nerve stimulation, and transcranial magnetic stimulation. Ann. N. Y. Acad. Sci. 993(2003):1-13; LABINER, D. M., Ahern, G. L. Vagus nerve stimulation therapy in depression and epilepsy: therapeutic parameter settings. Acta. Neurol. Scand. 115(2007): 23-33; AMAR, A. P., Levy, M. L., Liu, C. Y., Apuzzo, M. L. J. Vagus nerve stimulation. Proceedings of the IEEE 96(7, 2008):1142-1151; BEEKWILDER J P, Beems T. Overview of the clinical applications of vagus nerve stimulation. J Clin Neurophysiol 27(2,2010):130-138; CLANCY J A, Deuchars S A, Deuchars J. The wonders of the Wanderer. Exp Physiol 98(1,2013):38-45].

Unlike conventional vagus nerve stimulation, which involves the surgical implantation of electrodes about the vagus nerve, in its preferred embodiment the present use of vagus nerve stimulation is non-invasive. Non-invasive procedures are distinguished from invasive procedures (including minimally invasive procedures) in that the invasive procedures insert a substance or device into or through the skin (or other surface of the body, such as a wound bed) or into an internal body cavity beyond a body orifice. For example, transcutaneous electrical stimulation of a nerve is non-invasive because it involves attaching electrodes to the skin, or otherwise stimulating at or beyond the surface of the skin or using a form-fitting conductive garment, without breaking the skin [Thierry KELLER and Andreas Kuhn. Electrodes for transcutaneous (surface) electrical stimulation. Journal of Automatic Control, University of Belgrade 18(2,2008):35-45; Mark R. PRAUSNITZ. The effects of electric current applied to skin: A review for transdermal drug delivery. Advanced Drug Delivery Reviews 18 (1996) 395-425].

The present invention differs in several respects from previously disclosed applications of vagus nerve stimulation (VNS) to treat migraine headaches. In particular, only invasive VNS had been reported prior to Applicant's commonly assigned, co-pending patent applications concerning the use of noninvasive VNS to treat migraine headache [application U.S. Ser. No. 13/109,250, Publication US20110230701, entitled Electrical and magnetic stimulators used to treat migraine/sinus headache and comorbid disorders, to SIMON et al. and application U.S. Ser. No. 13/183,721, Publication US 20110276107, entitled Electrical and magnetic stimulators used to treat migraine/sinus headache, rhinitis, sinusitis, rhinosinusitis, and comorbid disorders, to SIMON et al. (which are hereby incorporated by reference)]. Furthermore, the parameters of stimulation that had been used previously are different than the parameters that are disclosed here [R M SADLER, R A Purdy & S Rahey. Vagal nerve stimulation aborts migraine in patient with intractable epilepsy. Cephalalgia 22(2002), 482-484; E. Daniela HORD, M. Steven Evans, Sajjad Mueed, Bola Adamolekun, and Dean K. Naritoku. The Effect of Vagus Nerve Stimulation on Migraines. The Journal of Pain 4 (9,2003): 530-534; Duncan A. GROVES, Verity J. Brown. Vagal nerve stimulation: a review of its applications and potential mechanisms that mediate its clinical effects. Neuroscience and Biobehavioral Reviews 29 (2005) 493-500; A MAUSKOP. Vagus nerve stimulation relieves chronic refractory migraine and cluster headaches. Cephalalgia 25(2005):82-86; M E LENAERTS, K J Oommen, J R Couch & V Skaggs. Can vagus nerve stimulation help migraine? Cephalalgia 28(2008), 392-395; Alberto Proietti CECCHINI, Eliana Mea and Vincenzo Tullo, Marcella Curone, Angelo Franzini, Giovanni Broggi, Mario Savino, Gennaro Bussone, Massimo Leone. Vagus nerve stimulation in drug-resistant daily chronic migraine with depression: preliminary data. Neurol Sci 30 (Suppl 1,2009):S101-S104; A. MAY and T. P. Jürgens. Therapeutic neuromodulation in primary headache syndromes (Therapeutische Neuromodulation bei primären Kopfschmerzsyndromen). Nervenarzt 2010: doi_10.1007/s00115-010-3170-x; Patent application US20050216070, entitled Method and system for providing therapy for migraine/chronic headache by providing electrical pulses to vagus nerve(s), to Boveja et al.].

The present invention also differs from earlier applications of VNS to treat migraine headache in that it relies on the measurement of evoked potentials to select parameters for the electrical stimulation and to test whether a particular patient is a suitable candidate for treatment using VNS. Evoked potentials are physiological voltage differences, ordinarily measured on the patient's scalp, that are evoked by the patient's experience of an event (event-related potentials). The scalp-recorded evoked potentials arise from ionic currents within neural networks of the patient's brain that are responses to the event. Most commonly (and in the present invention), the event that evokes the potential is a brief sensory stimulus that is deliberately applied to the patient. Examples of such stimuli are a flash of light, an audio click, or an electrical shock that is applied to the patient's skin [William R. GOFF. Human average evoked potentials: procedures for stimulating and recording. Chapter 3, pp. 101-156 in: Bioelectric Recording Techniques. Part B. Electroencephalography and Human Brain Potentials (Richard F. Thompson and Michale M. Patterson, eds). New York: Academic Press, 1974; David REGAN. Human Brain Electrophysiology. Evoked potentials and evoked magnetic fields in science and medicine. New York: Elsevier Science Publishing Co., 1989, pp. 1-672; Terence W. PICTON, Otavio G. Lins and Michael Scherg. The recording and analysis of event-related potentials. Chapter 1 (pp. 3-73) in Handbook of Neuropsychology, Vol. 10 (F. Boller and J. Grafman, eds). Amsterdam: Elsevier Science B.V., 1995; Monica FABIANI, Gabriele Gratton and Michael G. H. Coles. Event Related Potentials. Methods, Theory, and Applications. Chapter 3, pp. 53-84 In: John T. Cacioppo, Louis G. Tassinary and Gary G. Berntson (eds). Handbook of Psychophysiology, 2nd Ed. Cambridge: Cambridge University Press, 2000; Steven J. LUCK. An introduction to event-related potentials and their neural origins. Chapter 1 (pp. 1-50) in: Steven J. LUCK. An Introduction to the Event-Related Potential Technique. Cambridge, Mass.: MIT Press, 2005; Todd C. HANDY (ed). Event-related Potentials: A Methods Handbook. Cambridge, Mass.: MIT Press, 2005, pp. 1-380; Steven J LUCK and Emily S Kappenman, eds. Oxford handbook of event-related potential components. Oxford: Oxford University Press, 2012, pp. 1-626].

It was noted above that migraineurs exhibit sensory hyper-excitability during the premonitory or prodromal phase of a migraine headache, as well as during the headache phase itself. The hypersensitivity to external stimuli may manifest itself as photophobia, phonophobia, hyperosmia and cutaneous allodynia, corresponding respectively to heightened sensitivity to light, sound, odor, and touch (particularly of the scalp and face). For many years, evoked potential measurements have been performed on migraineurs in order to quantify abnormalities in the way in which they process sensory information. They may exhibit unusual evoked potential waveforms in response to a particular sensory stimulus, but the most striking aspect of the migraineur's processing of sensory information is that their evoked potentials often do not habituate in the same manner as normal individuals. Habituation is an adaptive process in which evoked potentials decrease in amplitude when a sensory stimulus is presented to an individual over an extended period of time [MEGELA A L, Teyler T J. Habituation and the human evoked potential. J Comp Physiol Psychol 93(6,1979):1154-1170]. Whereas normal individuals may gradually reduce their response to repeated sensory stimuli, as evidenced by the magnitude of the corresponding evoked potential as a function of time, the migraineur may maintain a constant (or even increased) responsiveness to the stimulus over a prolonged period of time [AMBROSINI A, de Noordhout A M, Sándor P S, Schoenen J. Electrophysiological studies in migraine: a comprehensive review of their interest and limitations. Cephalalgia 23 (Suppl 1,2003):13-31; M VALERIANI, M de Tommaso, D Restuccia, D Le Pera, M Guido, G D lannetti, G Libro, A Truini, G Di Trapani, F Puca, P Tonali, G Cruccu. Reduced habituation to experimental pain in migraine patients: a $CO(2)$ laser evoked potential study. Pain 105(1-2,2003):57-64; AMBROSINI A, Schoenen J. Electrophysiological response patterns of primary sensory cortices in migraine. J Headache Pain 7(6,2006):377-388; COPPOLA G, Vandenheede M, Di Clemente L, Ambrosini A, Fumal A, De Pasqua V, Schoenen J. Somatosensory evoked high-frequency oscillations reflecting thalamo-cortical activity are decreased in migraine patients between attacks. Brain 128(Pt 1,2005):98-103; COPPOLA G, Pierelli F, Schoenen J. Habituation and migraine. Neurobiol Learn Mem 92(2,2009):249-259; COPPOLA G, lacovelli E, Bracaglia M, Serrao M, Di Lorenzo C, Pierelli F. Electrophysiological correlates of episodic migraine chronification: evidence for thalamic involvement. J Headache Pain 14(1,2013):76, pp. 1-8; de TOMMASO M, Lo Sito L, Di Fruscolo O, Sardaro M, Pia Prudenzano M, Lamberti P, Livrea P. Lack of habituation of nociceptive evoked responses and pain sensitivity during migraine attack. Clin Neurophysiol 116(6,2005):1254-1264; Neelam VANEY, Abhinav Dixit, Tandra Ghosh, Ravi Gupta, M. S. Bhatia. Habituation of event related potentials: a tool for assessment of cognition in headache patients. Delhi Psychiatry Journal 11 (1, 2008):48-51].

Accordingly, it is one objective of the present invention to treat migraineurs with non-invasive vagus nerve stimulation in such a way that their evoked potentials habituate, so as to more nearly resemble normal individuals in that regard. Another objective of the invention is to test the migraineurs acutely with vagus nerve stimulation and then predict the likelihood that they will respond to noninvasive vagus nerve stimulation over an extended period of time, in such a way that the frequency and severity of chronic migraine attacks decreases. Attempts to increase the habituation of evoked potentials to sensory stimuli have been made using drugs, but not with vagus nerve stimulation [DICLEMENTE L, Puledda F, Biasiotta A, Viganò A, Vicenzini E, Truini A, Cruccu G, Di Piero V. Topiramate modulates habituation in migraine: evidences from nociceptive responses elicited by laser evoked potentials. J Headache Pain 14(1,2013):25, pp. 1-8]. Also, chronic invasive vagus nerve stimulation has been described as affecting the location of some peaks and troughs in certain evoked potentials of epileptic patients, but it has not been disclosed that noninvasive vagus nerve stimulation can affect the habituation of evoked potentials, particularly in those of migraineurs [NARITOKU D K, Morales A, Pencek T L, Winkler D. Chronic vagus nerve stimulation increases the latency of the thalamocortical somatosensory evoked potential. Pacing Clin Electrophysiol 15(10 Pt 2,1992):1572-1578].

The present invention may also be used to treat patients suffering from fibromyalgia, which like migraine headache and other primary headaches, involves pain that is associated with abnormalities in the processing of sensory signals. Unlike migraineurs, fibromyalgia sufferers experience significant muscle pain, stiffness, and muscle fatigue as one of their primary complaints, which might be attributable to an over-sensitization of nociceptors that are located in muscle or other deep tissues [ARNOLD L M. The pathophysiology, diagnosis and treatment of fibromyalgia. Psychiatr Clin North Am 33(2,2010):375-408; CLAUW D J, Arnold L M, McCarberg B H. The science of fibromyalgia. Mayo Clin Proc 86(9,2011):907-911; CLAUW D J. Fibromyalgia: an overview. Am J Med 122(12 Suppl,2009):S3-S13; Laurence A. BRADLEY. Pathophysiology of Fibromyalgia. Am J Med 122(12 Suppl,2009): S22; VIERCK, C. J. A mechanism-based approach to prevention of and therapy for fibromyalgia. Pain Research and Treatment, Article ID 951354 (2012), pp. 1-11].

In the United States, three medications are frequently used to treat fibromyalgia: pregabalin, duloxetine, and milnacipran, which act differently to influence transmission of sensory signals via central nociceptive pathways [ARNOLD LM, Clauw D J, Dunegan L J, Turk D C; et al. A framework for fibromyalgia management for primary care providers. Mayo Clin Proc 87(5,2012):488-496; Jennifer FITZGIBBONS. The truth about fibromyalgia will help you help patients ease their pain. American Nurse Today 2(9,2007): 40-45]. However, there is a great deal of trial and error in designing fibromyalgia treatment because of the heterogeneous symptoms of the patients, so combination therapies are common. As an alternative or complement to the use of medication, noninvasive electrical stimulation of the patient has also been used to treat fibromyalgia patients, involving the application of transcutaneous electrical nerve stimulation to the patient's spine and leg [DAILEY D L, Rakel B A, Vance C G, Liebano R E, Amrit A S, Bush H M, Lee K S, Lee J E, Sluka K A. Transcutaneous electrical nerve stimulation reduces pain, fatigue and hyperalgesia while restoring central inhibition in primary fibromyalgia. Pain 154(11,2013):2554-2562]. Cervical vagus nerve stimulation has also been used to treat fibromyalgia, but this has only involved the use of invasive stimulation, not the noninvasive stimulation that is disclosed here. Furthermore, that work does not involve the measurement of evoked potentials [LANGE G, Janal M N, Maniker A, Fitzgibbons J, Fobler M, Cook D, Natelson B H. Safety and efficacy of vagus nerve stimulation in fibromyalgia: a phase I/II proof of concept trial. Pain Med 12(9,2011):1406-1413; U.S. Pat. No. 8,457,748, entitled Vagus Nerve Stimulation for the Treatment of Fibromyalgia to Gudrun LANGE]. The occipital nerve has also been stimulated electrically to treat fibromyalgia, but this too has not involved the use of evoked potentials [PLAZIER M, Dekelver I, Vanneste S, Stassijns G, Menovsky T, Thimineur M, De Ridder D. Occipital Nerve Stimulation in Fibromyalgia: A Double-Blind Placebo-Controlled Pilot Study With a Six-Month Follow-Up. Neuromodulation. 2013 Oct. 7, pp. 1-8]. U.S. Pat. No. 8,428,719, entitled Systems and Methods for Respiratory-Gated Auricular Vagal Afferent Nerve Stimulation, to NAPADOW, also discloses treatment of fibromyalgia (among other diseases) by a noninvasive method, but that disclosure only involves the stimulation of the auricular branch of the vagus nerve (not the cervical vagus nerve), and it too does not involve the measurement of evoked potentials.

It has been known for many years that some individuals have unusual voluntary control over visceral functions, serving as apparent exceptions to the general rule that control of visceral organs is autonomous and non-voluntary. For example, some individuals are able to voluntarily increase their heart rate at will [HF WEST and WE Savage. Voluntary acceleration of the heart beat. Archives of Internal Medicine 22(1918):290-295; John T. KING, Jr. An instance of voluntary acceleration of the pulse. Bull. Johns Hopkins Hosp. 31(1920): 303-305; H FEIL, H D Green, D Eiber. Voluntary acceleration of heart in a subject showing the Wolff-Parkinson-White syndrome: clinical, physiologic, and pharmacologic studies. Am Heart J. 34(3,1947):334-348].

It is conceivable that the rare individuals who can voluntarily control autonomic functions such as heart rate, eye-pupil diameters, piloerection ("goose bumps" or cutis anserina), etc., do so via direct neural connections between the portions of the brain involved in volition and the central autonomic nervous system that connects to efferent visceral and motor nerves [LINDSLEY, D. B. and Sassaman, W. H. Autonomic activity and brain potentials associated with 'voluntary' control of the pilomotors. Journal of Neurophysiology 1(1938):342-349]. However, it is more plausible that the visceral control may be indirect, through voluntary muscular control that also affects the viscera, or through voluntary control over the circuits of the brain affecting emotions, which in turn affect the autonomic state of the viscera during fear, anger, pain, joy, etc., or by otherwise taking advantage of classically acquired (Pavlovian) conditional reflexes [Joseph E. LEDOUX. Emotion circuits of the brain. Annu Rev Neurosci 23(2000):155-184; KREIBIG S D. Autonomic nervous system activity in emotion: a review. Biol Psychol 84 (3,2010):394-421; CRITCHLEY H D. Neural mechanisms of autonomic, affective, and cognitive integration. J Comp Neurol 493(1,2005):154-166; DWORKIN B R, Dworkin S. Learning of physiological responses: II. Classical conditioning of the baroreflex. Behav Neurosci 109(6,1995):1119-1136].

In the early 1960s, several publications suggested that most individuals could learn to voluntarily control autonomic functions, such as heart rate, vasoconstriction, salivation, intestinal contraction, and galvanic skin response, but they did not address the issue of direct versus indirect voluntary control [H. D. KIMMEL. Instrumental conditioning of autonomically mediated behavior. Psychological Bulletin 67(1967):337-345; H. D. KIMMEL. Instrumental conditioning of autonomically mediated responses in human beings. American Psychologist 29(5,1974):325-335]. A landmark publication in 1969 by MILLER had a profound influence on work concerning whether the viscera could be controlled directly and voluntarily [Neal E MILLER. Learning of visceral and glandular responses. Science 163(3866, 1969):434-445]. That publication described the use of operant conditioning (also known as instrumental conditioning or Skinnerian conditioning) to train animals to control their heart rate and other visceral functions. Operant conditioning is distinguished from classical conditioning (Pavlovian or respondent conditioning) in that operant conditioning deals with the modification of voluntary behavior, through the use of reinforcement and punishment. Whereas Pavlovian responses are involuntarily reflexive and involve stimulus events that precede the learned response, in contrast, during operant conditioning, the reinforcement or punishment follows the learned response that is performed voluntarily. In the experiments by MILLER and colleagues, animals were temporarily paralyzed with curare and were mechanically ventilated, in order to eliminate the possibility that muscular contraction was responsible for the purported learned ability to voluntarily change heart rate and other visceral physiological variables that were investigated.

The results that were described by MILLER had broad implications and spawned a great deal of related work by other investigators over the following two decades, particularly work that is described below as the use of biofeedback [Neal E. MILLER. Biofeedback and visceral learning. Ann. Rev. Psychol. 29(1978):373-404]. However, his experimental results were eventually determined to be irreproducible and were retracted, and the conduct of the assistant who performed much of the actual laboratory work became suspect before he committed suicide [Barry R. DWORKIN and Neal E. Miller. Failure to replicate visceral learning in the acute curarized rat preparation. Behavioral Neuroscience 100(3, 1986):299-314; Marion NOTT. Are the claims true? The Evening Independent (St. Petersburg, Fla.) Oct. 3, 1977, page 11]. Despite the still-frequent citation of the work that MILLER has long since retracted, there is currently no credible evidence that any mammal can directly and voluntarily control visceral autonomic functions, such as heart rate. In fact, it is thought that the direct, voluntary control of visceral autonomic functions is not possible in principle, unless it were to be accompanied by the adaptation of internal bodily sensors that operate largely below the level of consciousness (interoceptors, see below) [Barry R. DWORKIN. Learning and Physiological Regulation. Chicago: University of Chicago Press, 1993, Chapter 8, pp. 162-185]. However, as described above, voluntary control over the viscera might be exerted indirectly via skeletal muscles or through voluntary modulation of an individual's emotional state. With this in mind, one objective of the present invention is to teach methods and devices that actually enable most individuals to directly and voluntarily control visceral autonomic functions, with or without simultaneous indirect voluntary control via skeletal muscle or emotion.

One explanation for our inability to voluntarily control visceral function is that the conscious mind cannot generally sense the state of the viscera, so one would have little conscious basis for directing voluntary visceral control, even if control over efferent nerves modulating activity of the end organs could be voluntarily exercised. In fact, the body contains many types of internal sensors (interoceptors) that operate largely below the level of consciousness, including baroreceptors and mechanoceptors, chemoreceptors, thermoreceptors, and osmoreceptors. Sensors located in skeletal muscles, ligaments, and bursae (proprioceptors) sense information related to muscle strain, location and orientation. Sensors that respond to painful stimuli (nociceptors) may be like other interoceptors, except that they generally have a small diameter (A-delta and C fibers) and convey signals to the central nervous system with a high frequency of discharge only after a threshold in the stimulus has been exceeded. In contrast to other peripheral sensors, nociceptors also do a poor job of discriminating the location of the stimulus, and they convey their signals via a special anterolateral route up the spinal cord to the thalamus. To the extent that one is conscious of the state of the viscera, e.g., during painful internal stimuli (stomach ache, angina pectoris, etc.), that awareness appears to result from interoceptive representation that first reaches the thalamus and eventually resides in the brain's right anterior insula, working in conjunction with the adjoining frontal operculum and the anterior cingulate cortex [Dieter VAITL. Interoception. Biological Psychology 42 (1996):1-27; CRITCHLEY H D, Wiens S, Rotshtein P, Ohman A, Dolan R J. Neural systems supporting interoceptive awareness. Nat Neurosci 7(2, 2004):189-195; CRAIG, A. D. How do you feel? Introception: the sense of the physiological condition of the body. Nat. Rev. Neurosci 3(2002):655-666; CRAIG A D. How do you feel—now? The anterior insula and human awareness. Nat Rev Neurosci 10(1,2009):59-70].

In order to make an individual artificially conscious of the otherwise unperceived state of an internal organ, investigators may electrically transduce a physiological signal, then use the magnitude of that signal to generate a proportionate signal that may be sensed by one of the individual's external senses. The generated signal is ordinarily an audio or visual representation of the magnitude of the transduced physiological signal. However, the generated signal may also be directed to another exteroceptive sense, e.g., using electrical stimulation, tactile stimulation with vibration or pressure, thermal stimulation, or olfactory stimulation. The individual whose physiological signal is being transduced may then voluntarily respond mentally to the magnitude of the generated signal. To the extent that the individual learns to control his or her body in such a way as to voluntarily modulate the value of the transduced physiological signal, then the patient is said to have learned to perform biofeedback.

According to rules of the U.S. Food and Drug Administration, "a biofeedback device is an instrument that provides a visual or auditory signal corresponding to the status of one or more of a patient's physiological parameters (e.g., brain alpha wave activity, muscle activity, skin temperature, etc.) so that the patient can control voluntarily these physiological parameters . . . ." [21 CFR 882.5050—Biofeedback device]. The individual will not necessarily be able to understand or explain how the voluntary control over the physiological signal has been achieved. Such biofeedback may also be considered to be a form of instrumental operant learning, in which the reward to the individual is the satisfaction of being able to voluntarily control the transduced physiological signal [Frank ANDRASIK and Amanda O. Lords. Biofeedback. Chapter 7, pp. 189-214 In: Lynda W. Freeman, ed. Mosby's Complementary & Alternative Medicine A Research-based Approach. St. Louis, Mo.: Mosby Elsevier, 2009; John V. BASMAJIAN. Biofeedback—Principles and Practices for Clinicians, 3rd Edn. Baltimore: Williams & Wilkins, 1989 pp 1-396; Mark S. SCHWARTZ (ed). Biofeedback. A Practitioner's Guide (2nd. Ed). New York: Guilford Press, 1995. pp 1-908].

Biofeedback methods and devices have been used in an attempt to manage many medical conditions, including migraine headache and fibromyalgia. Some such methods involve relaxation of muscles using electromyographic (EMG) biofeedback to counteract factors that contribute to the onset of symptoms. Other methods use biofeedback involving EEG or other physiological signals [William J. MULLALLY, Kathryn Hall M S, and Richard Goldstein. Efficacy of Biofeedback in the Treatment of Migraine and Tension Type Headaches. Pain Physician 12(2009):1005-1011; STOKES D A, Lappin M S. Neurofeedback and biofeedback with 37 migraineurs: a clinical outcome study. Behav Brain Funct 6(2010):9, pp. 1-10; Yvonne NESTORIUC, Alexandra Martin, Winfried Rief, Frank Andrasik. Biofeedback Treatment for Headache Disorders: A Comprehensive Efficacy Review. Appl Psychophysiol Biofeedback 33(2008):125-140; BABU A S, Mathew E, Danda D, Prakash H. Management of patients with fibromyalgia using biofeedback: a randomized control trial. Indian J Med Sci 61(8,2007):455-461; CARO X J, Winter E F. EEG biofeedback treatment improves certain attention and somatic symptoms in fibromyalgia: a pilot study. Appl Psychophysiol Biofeedback 36(3,2011):193-200]. One objective of the present invention is to treat headaches and fibromyalgia using improved biofeedback mechanisms by making use of evoked potentials that are evoked by the stimulation of the vagus nerve.

SUMMARY

The present invention is concerned primarily with devices and methods for the treatment of medical disorders, such as migraine or other primary headaches, or of fibromyalgia, in which treatment involves the noninvasive electrical stimulation of a cervical vagus nerve.

In one aspect of the invention, an evoked potential of the patient is measured and the signal delivered to the vagus nerve by the stimulator is adjusted based upon the measured evoked potential in order to optimize the signal and the treatment. Sensors used by the invention include one or more electrodes applied to the scalp of the patient, in order to measure the evoked potentials. However, the invention contemplates the use of many other types of physiological sensors as well, particularly ones that are used for ambulatory monitoring. Parameters of the nerve stimulation impulse that can be varied include certain aspects of the signal, such as the frequency, amplitude (voltage or current), duty cycle and/or the duration of the electrical impulse. Alternatively or additionally, the position and/or orientation of the stimulation device on the patient's neck may be adjusted based on the evoked potential. In certain embodiments, the device may be alternated between the right and left side of the patient's neck to optimize the signal based on the measurement of evoked potentials.

In another aspect of the invention, feedback provided by the system's sensors is used to optimize the signal applied to the nerve. The use of such feedback is useful in establishing an initial set of stimulation parameter values for an individual patient. Furthermore, the plotting of some feature(s) of the evoked potential waveform as a function of the varied parameters of the electrical stimulation waveform may be used to characterize the electrophysiology of the individual patient (stimulus/response gain, threshold, saturation, linearity or non-linearity, etc.). In fact, even the demonstrated ability to vary the evoked potential waveform as a function of the parameters of the electrical stimulus waveform may be used to verify that the vagus nerve is in fact being stimulated, or that the position and/or orientation of the stimulation electrodes are optimal.

The system comprises software and hardware components allowing it to fix the parameters of the electrical impulses once they have been optimized, based upon criteria that are sensed by the system's sensor(s). Thereafter, the system's signal generator is capable of applying the fixed electrical impulses to the patient. However, if the sensed properties of the patient change over an extended period of time, the system may re-optimize the stimulation parameters as the need arises.

Once the stimulator is properly placed against the skin on the right or left side of the neck of the patient, electrical impulses are applied through the electrodes of the stimulator to the vagus nerve, to treat the patient's condition or a symptom of that condition. For some conditions, the treatment may be acute, meaning that the electrical impulse immediately begins to interact with one or more nerves to produce a response in the patient. In some cases, the electrical impulse will produce a response in the nerve(s) to improve the patient's condition or symptom in less than 3 hours, preferably less than 1 hour and more preferably less than 15 minutes. For other conditions, intermittently scheduled or as-needed stimulation of the nerve may produce improvements in the patient over the course of several days, weeks, months or even years (i.e., chronic treatment). A more complete description of such a device for the treatment of migraineurs can be found in one of applicant's co-pending patent applications referenced above.

The noninvasive vagus nerve stimulator is configured to induce a peak pulse voltage sufficient to produce an electric field in the vicinity of the nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m (preferably less than 100 V/m) and/or an electrical field gradient of greater than 2 V/m/mm. Electric fields that are produced at the vagus nerve are generally sufficient to excite all myelinated A and B fibers, but not necessarily the unmyelinated C fibers. However, by using a suitable amplitude of stimulation, excitation of A-delta and B fibers may also be avoided.

In another aspect of the invention, devices and methods are disclosed for modulating neurotransmitter levels within the central nervous system of patients who have a demonstrable habituation deficit with regard to their evoked potentials. In this embodiment, the patient may first be tested by stimulating visual, auditory, or somatosensory sense organs (e.g., the cervical cutaneous senses) and measuring the corresponding evoked potentials, over an extended period of time. The patients who do not exhibit significant habituation in their evoked potentials, in response to the sensory stimulation over a prolonged period of time, are then subjected to an acute stimulation of the vagus nerve. The patient is then retested by stimulating the sense organs and re-measuring the previously-measured evoked potentials. For some of the individuals (the "responders"), the effect of the intervening acute vagus nerve stimulation is to significantly reduce the magnitude of features of evoked potentials, thereby artificially effecting a form of evoked potential habituation. Those individuals are therefore candidates for chronic treatment of their disorder (e.g., migraine headaches), by performing the vagus nerve stimulation on a regular basis, with the objective of reducing the duration, frequency and severity of symptoms associated with the disorder.

The vagus nerve stimulation may also be useful for the treatment of patients irrespective of whether the patient exhibits a deficit in the habituation of evoked potentials. When evoked potential measurements are performed on populations of migraineurs and control normal individuals, before and after acute vagus nerve stimulation with different stimulation parameters, statistical methods are used to determine which features of the pre- and post-stimulation evoked potentials, as well as their differences, are most closely related to the acute reduction of pain in the patient. Similar statistical methods are used to determine which features of the initial pre- and post-stimulation evoked potentials, as well as their differences, are most closely related to reduction in the chronic frequency and severity of painful episodes. These data are then used to select patients as candidates for treatment and to set nerve stimulation parameters.

In another aspect of the invention, one or more of the above-mentioned sensors may be used to perform biofeedback, in which output from the sensor is used to generate a biofeedback signal that can be experienced by at least one of the patient's exteroceptive sense organs (time-varying audio signal, visual display, tactile signal, etc.). In an exemplary embodiment, the sensed property is a characteristic of an evoked potential, such as the amplitude of a peak or trough having a particular latency, e.g., the amplitude of a P300 peak. The biofeedback signal is generally constructed to be proportional to the sensor's output. The patient then voluntarily uses conscious awareness of that biofeedback signal to mentally control a bodily function or structure that modulates the amplitude of the neurophysiological property that is measured by the sensor, thereby completing the biofeedback loop.

In the present invention, one preferred method of providing a biofeedback signal to the patient is by electrically stimulating the cervical skin with a signal that varies according to the magnitude of the output of a physiological sensor. The electrodes that stimulate the skin are the same as the ones that may also be used to stimulate a vagus nerve that lies deeper under the electrodes and skin.

Treating the patients may also be implemented automatically (involuntarily) within the context of engineering control theory. Neurophysiological signals that are measured with sensors are presented as input to a controller. The controller, comprising for example, the disclosed nerve stimulator, a PID, and a feedback or feedforward model, then provides input to the patient via stimulation of a vagus nerve. The vagus nerve stimulation in turn modulates components of the patient's nervous system, such as the autonomic nervous system, which results in modulation of the physiological properties that are measured with sensors, thereby completing the automatic control loop. The modulated components of the patient's nervous system may include particular resting state networks, such as the default mode network.

In another aspect of the invention, interoceptive representation that is presented to—and is represented in—the brain's right anterior insula and related structures, may be derived in part from artificial or virtual signals that correspond to stimulation of fibers in the vagus nerve, rather from the ordinary signaling of bodily interoceptors. The patient may be conscious of the artificial interoception and may use it to mentally control a bodily function or structure that modulates the amplitude of the physiological property that is measured by the physiological sensor. Thus, the invention contemplates a voluntary, conscious response to the artificial interoception, even though it originates from vagus nerve stimulation rather than from stimulation of an exteroceptive sense as in biofeedback.

In the most general configuration of the disclosed devices and methods, the three above-mentioned mechanisms (biofeedback, direct stimulation of the vagus nerve to effect automatic control, and artificial interoceptive sensation) will collectively modulate the target neurophysiological system, interacting with one another to determine the value of the sensed physiological signal. Part of the interaction is determined by the manner in which the nerve stimulator/biofeedback device/neurophysiological controller is programmed. For example, direct stimulation of the neurophysiological system via the vagus nerve may be programmed to follow and amplify or enhance changes in the measured sensor values that occur as a result of biofeedback. In other embodiments, both biofeedback and vagus nerve stimulation are performed simultaneously, and mathematical modeling is used to infer the physiological effects that are due to the biofeedback, thereby allowing the device to infer the conscious intentions of the patient and apply the vagus nerve stimulation accordingly. For the subset of individuals who are unable to control their neurophysiological signals adequately using biofeedback, even after multiple training attempts, and even with amplification of biofeedback effects using vagus nerve stimulation as indicated above, the device may also be programmed to use vagus nerve stimulation alone to automatically perform the neurophysiological control.

In a preferred embodiment of the invention, an electrical stimulator housing comprises a source of electrical power and two or more remote electrodes that are configured to stimulate the vagus nerve. The stimulator may comprise two electrodes that lie side-by-side, wherein the electrodes are separated by electrically insulating material. Each electrode is in continuous contact with an electrically conducting medium that extends from the patient-interface element of the stimulator to the electrode. The interface element contacts the patient's skin when the device is in operation.

The system may also comprise a docking station that is used to charge a rechargeable battery within the stimulator housing. The docking station and stimulator housing may also transmit data to one another. They may also transmit data to, and receive data from, a computer program in a patient interface device, such as a mobile phone or nearby computer. Physiological sensors may transmit their signals to the stimulator, docking station, and/or interface device. Such data transmission is preferably wireless, but wired communication between devices is also contemplated.

For stimulation of a deep nerve, current passing through electrodes of the stimulator may be about 0 to 40 mA, with voltage across the electrodes of about 0 to 30 volts. The current is passed through the electrodes in bursts of pulses. There may be 1 to 20 pulses per burst, preferably five pulses. Each pulse within a burst has a duration of about 20 to 1000 microseconds, preferably 200 microseconds. A burst followed by a silent inter-burst interval repeats at 1 to 5000 bursts per second (bps, similar to Hz), preferably at 15-50 bps, and even more preferably at 25 bps. The preferred shape of each pulse is a full sinusoidal wave.

The preferred stimulator shapes an elongated electric field of effect that can be oriented parallel to a long nerve, such as a vagus. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, avoiding the stimulation of nerves in the skin that produce pain, but optionally stimulating receptors in the skin that may be used for biofeedback purposes.

In a minimally invasive embodiment of the invention, a stimulation device comprises one or more electrodes and a pulse generator and is configured for implantation at a target site adjacent to or near the cervical vagus nerve. The energy that is used to produce the impulses is received wirelessly by a dipole or other type of antenna that is also part of the stimulator. The received energy is preferably from far-field or approximately plane wave electromagnetic waves in the frequency range of about 0.3 to 10 GHz, more preferably about 800 MHz to 6 GHz and even more preferably about 800 MHz to 1.2 GHz. In an exemplary embodiment, the carrier signal is around 915 MHz. The electrical energy is transmitted from the antenna of an external energy source that is preferably a meter or more outside the patient, but that may also be situated closer or even be placed within the patient. In some embodiments, the transmitter may be worn around the neck as a pendant, placed in a pocket, attached to a belt or watch, or clipped to clothing.

The novel systems, devices and methods for treating medical conditions are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

This application refers to the following patents and patent applications, the entire disclosures of which are hereby incorporated by reference for all purposes: U.S. patent application Ser. No. 13/279,437 filed Oct. 24, 2011, U.S. patent application Ser. No. 13/222,087 filed Aug. 31, 2011, U.S. patent application Ser. No. 13/183,765 filed Jul. 15, 2011, U.S. patent application Ser. No. 13/183,721 filed Jul. 15, 2011, U.S. patent application Ser. No. 13/109,250 filed May 17, 2011, U.S. patent application Ser. No. 13/075,746 filed Mar. 30, 2011, U.S. patent application Ser. No. 13/005,005 filed Jan. 12, 2011, U.S. patent application Ser. No. 12/964,050 filed Dec. 9, 2010, U.S. patent application Ser. No. 12/859,568 filed Aug. 9, 2010, U.S. patent application Ser. No. 12/408,131 filed Mar. 20, 2009, U.S. patent application Ser. No. 12/612,177 filed Nov. 9, 2009 now U.S. Pat. No. 8,041,428 issued Oct. 18, 2011, U.S. patent application Ser. No. 12/859,568, filed Aug. 19, 2010, U.S. patent application Ser. No. 13/208,425, filed Aug. 12, 2011, U.S. patent application Ser. No. 12/964,050, filed Dec. 9, 2010, U.S. patent application Ser. No. 13/005,005, filed Jan. 12, 2011, U.S. application Ser. No. 13/024,727, filed Feb. 10, 2011, U.S. application Ser. No. 13/075,746, filed Mar. 30, 2011, U.S. application Ser. No. 13/109,250, filed May 17, 2011, U.S. application Ser. No. 13/183,721, filed Jul. 15, 2011, US application Ser. No. 13/222,087, filed Aug. 31, 2011, U.S. application Ser. No. 13/357,010, filed Jan. 24, 2012, U.S. application Ser. No. 13/736,096, filed Jan. 8, 2013, U.S. application Ser. No. 13/603,781, filed Sep. 5, 2012, U.S. application Ser. No. 13/671,859, filed Nov. 8, 2012, U.S. application Ser. No. 13/731,035, filed Dec. 30, 2012, U.S. application Ser. No. 13/858,114, filed Apr. 8, 2013, and U.S. application Ser. No. 14/071,577, filed Nov. 4, 2013.

BRIEF DESCRIPTION OF DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIGS. 1A-1B provide schematic diagrams for the operation of: (FIG. 1A) a conventional evoked potential measurement device and (FIG. 1B) a closed loop nerve stimulator, evoked potential measurement device and/or biofeedback, according to the present invention.

FIGS. 3A-3C illustrate front (FIG. 3A) and back (FIG. 3B) views of a dual-electrode stimulator according to an embodiment of the present invention, which is shown to attach to a docking station (FIG. 3C).

FIG. 7 illustrates the approximate position of the housing of the stimulator according one embodiment of the present invention, when used to stimulate the right vagus nerve in the neck of an adult patient.

FIG. 8 illustrates the approximate position of the housing of the stimulator according one embodiment of the present invention, when used to stimulate the right vagus nerve in the neck of a child.

FIGS. 9A-9C illustrate the vertebrae and major vessels of the neck, including vessels within the carotid sheath (FIG. 9A), as well as muscles that lie in the vicinity of those vessels, namely, the platysma muscle (FIG. 9B) and sternocleidomastoid muscle (FIG. 9C).

FIGS. 14A-14B show an evoked potential resulting from noninvasive stimulation of a patient's vagus nerve (FIG. 14A), and the corresponding evoked potential when the stimulator is repositioned slightly so as to avoid stimulation of the vagus nerve (FIG. 14B).

DETAILED DESCRIPTION OF PREFERRED EMBODIMENTS

In the present invention, electrodes applied to the skin of the patient generate electrical current or voltage impulses within tissue of the patient. One of the objectives of the invention is to apply the electrical impulses so as to interact with intrinsic signals of one or more nerves, in order to achieve a therapeutic result, with or without the simultaneous provision of a biofeedback signal to the patient. Much of the disclosure will be directed specifically to treatment of a patient by electrical stimulation in or around a vagus nerve, with devices positioned non-invasively on or near a patient's neck. As recognized by those having skill in the art, the methods should be carefully evaluated prior to use in patients known to have preexisting cardiac issues. It will also be appreciated that the devices and methods of the present invention can be applied to other tissues and nerves of the body, including but not limited to other parasympathetic nerves, sympathetic nerves, spinal or cranial nerves.

Figure 1A:
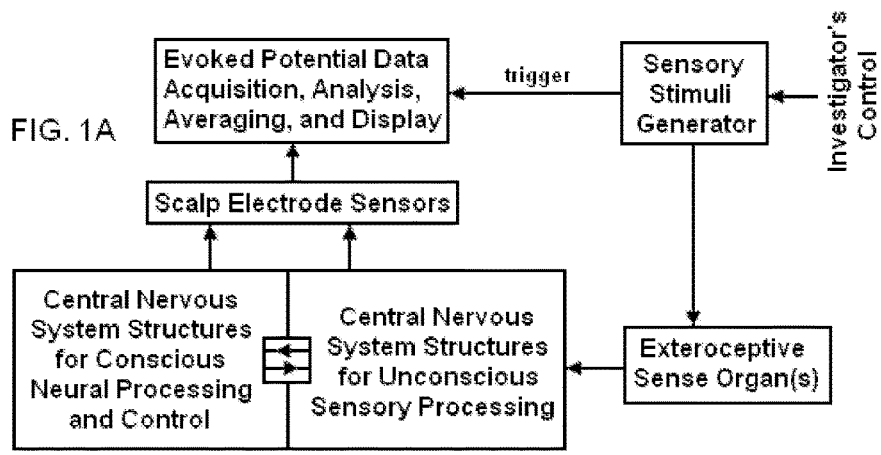

Prior art is shown in FIG. 1A, which illustrates components involved in a conventional evoked potential (EP) measurement. The investigator initiates the generation of one or more sensory stimuli from a stimulator generator, such as a flash of light, an audio click, or bipolar transcutaneous electrical stimulation applied on the skin over the median, ulnar, peroneal, or posterior tibial nerve [William R. GOFF. Human average evoked potentials: procedures for stimulating and recording. Chapter 3, pp. 101-156 in: Bioelectric Recording Techniques. Part B. Electroencephalography and Human Brain Potentials (Richard F. Thompson and Michale M. Patterson, eds). New York: Academic Press, 1974; David REGAN. Human Brain Electrophysiology. Evoked potentials and evoked magnetic fields in science and medicine. New York: Elsevier Science Publishing Co., 1989, pp. 1-672; Terence W. PICTON, Otavio G. Lins and Michael Scherg. The recording and analysis of event-related potentials. Chapter 1 (pp. 3-73) in Handbook of Neuropsychology, Vol. 10 (F. Boller and J. Grafman, eds). Amsterdam: Elsevier Science B.V., 1995; Monica FABIANI, Gabriele Gratton and Michael G. H. Coles. Event Related Potentials. Methods, Theory, and Applications. Chapter 3, pp. 53-84 In: John T. Cacioppo, Louis G. Tassinary and Gary G. Berntson (eds). Handbook of Psychophysiology, 2nd Ed. Cambridge: Cambridge University Press, 2000; Steven J. LUCK. An introduction to event-related potentials and their neural origins. Chapter 1 (pp. 1-50) in: Steven J. LUCK. An Introduction to the Event-Related Potential Technique. Cambridge, Mass.: MIT Press, 2005; Todd C. HANDY (ed). Event-related Potentials: A Methods Handbook. Camridge, Mass.: MIT Press, 2005, pp. 1-380; Steven J LUCK and Emily S Kappenman, eds. Oxford handbook of event-related potential components. Oxford: Oxford University Press, 2012, pp. 1-626]. A pain-associated evoked potential may also be initiated using a laser light pulse that is applied to the skin of the subject [TREEDE R D, Lorenz J, Baumgärtner U. Clinical usefulness of laser-evoked potentials. Neurophysiol Clin 33(6,2003):303-314; GARCIA-LARREA L, Frot M, Valeriani M. Brain generators of laser-evoked potentials: from dipoles to functional significance; Neurophysiol Clin 33(6,2003):279-292]. The stimulus then activates visual, auditory, somatosensory, or pain exteroceptive sense organ receptors, respectively, in the subject of the measurement. The neural responses of the sensory receptors are then transmitted to structures within the central nervous system, which initially process the sensory information without conscious participation of the subject. However, those structures are also in communication with structures in the central nervous system that make it possible for the subject to subsequently become conscious of the sensory information, for example, by recognizing the novelty or significance of the stimulus.

As also shown in FIG. 1A, electrode sensors placed at well-defined locations on the scalp of the subject make it possible to measure electrical potentials that are evoked as the underlying structures of the central nervous system processes the sensory information, both unconsciously and consciously. Such neural processing generates ionic current flows within a brain of the subject that can be measured on the scalp. Actual measurement of the potentials is triggered by the activity of the sensory stimulus generator, so that the measured potentials are time-locked relative to the onset of the stimulus. When a transient response EP is measured, the EP waveform ordinarily consists of a series of peaks and valleys relative to the baseline potential, which are characterized by their amplitudes (positive or negative), as well as their times of occurrence relative to the stimulus (their latencies). The potentials that are so-measured are a mixture of the neural activity of structures involved in both the unconscious and conscious processing of the sensory information, as may be inferred by performing the EP measurement when the subject is or is not anesthetized, or awake versus asleep. Transient response EP data acquisition equipment may also be capable of averaging multiple successive evoked potentials (so as to increase the signal-to-noise of the EP data) and also automatically locate peaks or other features in the evoked potential waveform, such as a P300 peak that corresponds to a conscious evaluation on the part of the patient that the stimulus is interesting [KNIGHT R T, Scabini D. Anatomic bases of event-related potentials and their relationship to novelty detection in humans. J Clin Neurophysiol 15(1,1998):3-13; KECECI H, Degirmenci Y, Atakay S. Habituation and dishabituation of P300. Cogn Behav Neurol 19(3,2006):130-134].

Peaks and troughs in the transient response EP may often be identified by comparing their properties with those found in normative databases. Artifacts that appear in the EP may also be identified and preferably eliminated. In the case of electrical stimulation this may include a shock or stimulus artifact that is due to conduction through the skin from the stimulus to the recording electrode. It may also be a myogenic artifact that originates in scalp muscles in the vicinity of recording electrodes, or other muscles, and may be identified, for example, by the use of chemical muscle relaxants that cause the artifact to disappear.

The transient EP is produced as a response to a single brief stimulus, and for purposes of signal-averaging, the response is not evoked again until the potential has returned to its value prior to the stimulus. In contrast, a steady state EP is produced in response to stimuli that are repeated periodically, even though the potential may not have had time to return to its baseline value between stimuli. Such a steady-state EP will also exhibit a reproducible waveform, but because the waveform is dependent on factors such as the frequency of stimulus repetition, it is conventionally characterized in terms of its Fourier spectrum. However, it may also be characterized in terms of the amplitude and latency of peaks and troughs corresponding to the temporal summation of synaptic potentials [David REGAN. Distinction between the transient and steady-state responses of a system. Section 1.3, pp. 34-43 in: David REGAN. Human Brain Electrophysiology. Evoked potentials and evoked magnetic fields in science and medicine. New York: Elsevier Science Publishing Co., 1989; ZAKHAROVA I, Kornhuber M E. Facilitation of late somatosensory evoked potentials by electrical train stimuli. Neurosci Lett 557(Pt B,2013):135-137].

Figure 1B:
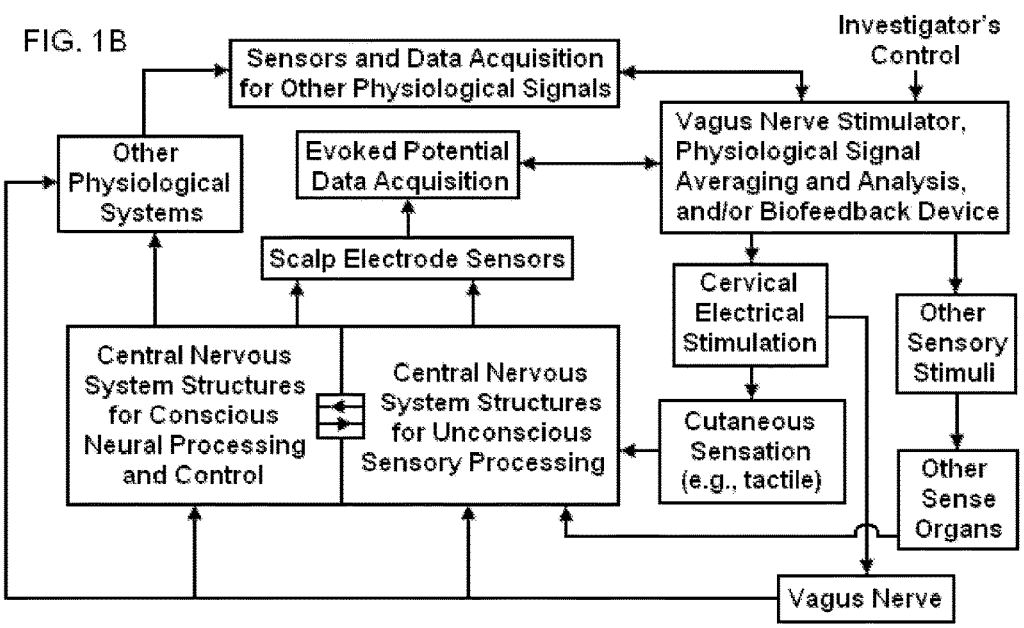

Embodiments of the present invention are shown in FIG. 1B, which are different from the prior art shown in FIG. 1A in several respects. First, in its non-invasive embodiment, it involves transcutaneous electrical stimulation applied to the skin over the vagus nerve in the neck, rather than the median, posterior tibial, or other nerves that are typically used in somatosensory evoked potential work. The vagus nerve at that cervical location comprises on the order of 100,000 axons that serve a large number of autonomic, sensory, and motor functions that are quantitatively and qualitatively greater than those served by the median, tibial, or other such nerves. Similarly, the vagus nerve axons at that cervical location serve many more functions than branches of the vagus nerve at other locations, such as auricular branch at the tragus of the ear. Therefore, the range of physiological effects that may be produced by the device shown in FIG. 1B is correspondingly greater than those that may be produced by the stimulation of other nerves or other vagal nerve branches.

As indicated in FIG. 1B the investigator initiates the operation of a vagus nerve stimulator, which generates cervical electrical stimulation through electrodes placed on the surface of the neck of the subject. The stimulation may involve the application of one or more superimposed stimulation waveforms, the parameters of which determine whether the stimulation preferably affects only receptors in the patient's skin, and/or whether the stimulation reaches the underlying vagus nerve. The somatosensory electrical stimulus used in FIG. 1A to stimulate nerves is ordinarily a monophasic square wave pulse having a duration of 100 microsecond to 1 second. In contrast, the devices shown in FIG. 1B use electrical stimulation waveforms that may be biphasic, bursting, sinusoidal and otherwise differ from monophasic square waves, in addition to the possibility that they involve the superposition of waveforms that are directed to the vagus nerve and cutaneous receptors. The stimulus waveforms produced by the devices shown in FIG. 1B may be either single-shot (to generate transient EP responses) or periodic (to generate steady-state EP responses).

FIG. 1B illustrates a closed-loop (feedback or biofeedback) system for acquiring evoked potential data. Unlike the system shown in FIG. 1A, the vagus nerve stimulator device may control and vary successive sensory stimuli, once the investigator has initiated its operation. Thus, in FIG. 1B, the vagus nerve stimulator may trigger the generation of the cervical sensory stimulus on its own, based upon its analysis of previous transient or steady-state evoked potentials that it had received from the scalp electrodes and/or from the analysis of other physiological data that it has received from other physiological sensors. Examples of such other physiological data are electrodermal voltages measured from sites such as the subject's hand or respiratory data that have been measured using impedance pneumography sensors.

The evoked potentials that are processed by such feedback methods may in some situations be generated primarily by the central nervous system structures for unconscious sensory processing. As an example of such feedback methods, the vagus nerve stimulator may vary a parameter of the stimulus waveform (e.g. amplitude, or frequency in the case of steady-state EP measurement), measure the resulting EP waveform, again vary the parameter based on that waveform measurement, and then repeat this procedure iteratively until it results in an EP waveform that exhibits preferred features that lie within some specified range. The use of such feedback would be particularly useful in establishing an initial set of stimulation parameter values for an individual, considering that different individuals may vary significantly with respect to the details of their preferred electrical stimulation waveforms. Furthermore, the plotting of some feature(s) of the EP waveform as a function of the varied parameters of the electrical stimulation waveform may be used to characterize the electrophysiology of the individual patient (stimulus/response gain, threshold, saturation, linearity or non-linearity, etc.). In fact, even the demonstrated ability to vary the EP waveform as a function of the parameters of the electrical stimulus waveform may be used to verify that the vagus nerve is in fact being stimulated, or that the position and/or orientation of the stimulation electrodes are optimal.

In other situations, the relevant features of the evoked potentials may be generated primarily by the central nervous system structures that are involved in conscious neural processing and control. As an example of that situation, the individual may consciously react to the sensations that result from the vagus nerve stimulation, as evidenced by the appearance of a P300 peak in his/her transient evoked potential. After detecting the P300 peak, the device can use that fact to vary the parameters of the next vagus nerve stimulation. For example, the P300 peak may appear once the stimulation amplitude reaches a sensory threshold that is recognized by the subject, or the properties of the P300 peak may change when the stimulation amplitude is so large that it produces pain. Because in that embodiment of the invention the individual is consciously controlling the operation of the device via the P300 peak, this evoked potential application is a type of biofeedback, rather than purely automatic feedback.

Note that the type of biofeedback that is described above is different from other types of biofeedback, known as neurofeedback, that also measure potentials with scalp electrodes. This is because neurofeedback measures spontaneous (EEG) potentials, rather than evoked potentials. Thus, in neurofeedback, subjects are typically presented with an audio tone whenever their EEG contains significant EEG waves of a particular type (e.g., alpha, beta, high beta, theta, or sensorimotor). Some individuals can concentrate on the tone and then learn to voluntarily suppress and/or enhance the time spent in that EEG state, as evidenced by their ability to voluntarily increase or decrease the amplitude of the tone [John N. DEMOS. Getting Started with Neurofeedback. New York: W.W. Norton & Co., 2005. pp. 1-281].

Another novel feature of the system shown in FIG. 1B is that it may be used to train an individual to consciously and voluntarily control the "other physiological system" that is labeled in the figure. In such a biofeedback application, the skin at the subject's neck is stimulated in proportion to a previous or concurrently measured property of the "other physiological system" (e.g., electrodermal voltage measured on the subject's hand), such that the subject is made consciously aware of the magnitude of the measured physiological property through the magnitude of the skin stimulation. Alternatively, the stimulation applied to the subject's neck is a function of the features of the measured evoked potential (e.g., amplitude or latency of one or more particular EP waveform peaks or troughs). The subject then attempts to mentally control the magnitude of the skin stimulation, and thereby consciously control the magnitude of the measured physiological property through thought alone. The electrical signals that simulate cutaneous nerves within the skin may be analog signals that vary in some continuous way relative to the physiological property that is being transduced. Alternatively, the biofeedback signals may be digital, comprising recognizable coded pulse trains, as has been suggested in connection with tactile communication devices for the blind. For example, electrocutaneous signals with three discrete intensity levels and three discrete long-pulse durations can be discriminated [R. H. GIBSON. Electrical stimulation of pain and touch. pp. 223-261. In: D. R. Kenshalo, ed. The Skin Senses. Springfield, Ill.: Charles C Thomas, 1968; Erich A. PFEIFFER. Electrical stimulation of sensory nerves with skin electrodes for research, diagnosis, communication and behavioral conditioning: A survey. Medical and Biological Engineering. 6(6,1968):637-651; Alejandro HERNANDEZ-ARIETA, Hiroshi Yokoi, Takashi Ohnishi, Tamio Arai. An f-MRI study of an EMG Prosthetic Hand Biofeedback System. In: T. Arai et al. (Eds.). IAS-9, Proceedings of the 9th International Conference on Intelligent Autonomous Systems, University of Tokyo, Tokyo, Japan, Mar. 7-9, 2006, Amsterdam: IOS Press, 2006, pp. 921-929; Kahori KITA, Kotaro Takeda, Rieko Osu, Sachiko Sakata, Yohei Otaka, Junichi Ushiba. A Sensory feedback system utilizing cutaneous electrical stimulation for stroke patients with sensory loss. Proc. 2011 IEEE International Conference on Rehabilitation Robotics, Zurich, Switzerland, Jun. 29-Jul. 1, 2011, 2011:5975489, pp 1-6].

It is understood that although the biofeedback component of FIG. 1B may be configured to use only electrical stimulation of the skin, the system may be configured to use additional sensory modalities as well, such as audio or visual biofeedback signals. However, for the present invention, the use of audio and visual sensory stimuli would ordinarily be used instead to evoke auditory or visual evoked potentials. Thus, FIG. 1B contains components "Other sensory stimuli" and "Other Sense Organs" that may refer to the stimulation of auditory or visual senses. In that situation, the vagus nerve stimulator/biofeedback device may also produce stimuli that stimulate vision or hearing (e.g., a flash of light or a click), thereby producing visual or auditory evoked potentials. Those "other sense organ" evoked potentials may then be measured via the scalp electrodes, and selected quantitative properties of the evoked potentials may then be automatically extracted by the vagus nerve stimulator/biofeedback device. Those properties may then be presented as a cutaneous sensation to the subject, via cervical electrical stimulation. In this embodiment, the subject becomes aware of the magnitude of the "other sense organ" evoked potential through the magnitude of the cutaneous sensation as biofeedback. It is understood that the cutaneous sensation itself may contribute to the evoked potential waveform, and preliminary experiments are used to distinguish which features of the EP waveform are due to the cutaneous stimulation and which are due to the "other sense organ", such that the EP waveform feature used for the biofeedback arises primarily from stimulation of the "other sense organ."

The subject may then endeavor, using thought alone, to consciously increase or decrease the magnitude of the measured evoked potential property that is produced by stimulation of the "other sense organ", as the magnitude of the property is supplied as a cutaneous biofeedback signal. The learned ability to control that property would be particularly valuable to individuals who suffer from migraine headaches, because they often suffer from what is known as a deficit of habituation. Whereas the evoked potentials from normal individuals generally decrease in magnitude as the corresponding stimulus is applied over an extended period of time (habituation), the evoked potentials from migraineurs often do not. Thus, if the migraineur is able to learn to consciously reduce the magnitude of features of the evoked potential (effectively, to habituate the EP), his or her EP electrophysiology will become more nearly like that of a normal individual, so that the likelihood of the subject's migraine headaches may thereby be reduced. [MEGELA A L, Teyler T J. Habituation and the human evoked potential. J Comp Physiol Psychol. 93(6,1979):1154-1170; AMBROSINI A, de Noordhout A M, Sándor P S, Schoenen J. Electrophysiological studies in migraine: a comprehensive review of their interest and limitations. Cephalalgia 23 (Suppl 1,2003): 13-31; AMBROSINI A, Schoenen J. Electrophysiological response patterns of primary sensory cortices in migraine. J Headache Pain 7(6,2006):377-388; COPPOLA G, Vandenheede M, Di Clemente L, Ambrosini A, Fumal A, De Pasqua V, Schoenen J. Somatosensory evoked high-frequency oscillations reflecting thalamo-cortical activity are decreased in migraine patients between attacks. Brain128(Pt 1,2005):98-103; COPPOLA G, Pierelli F, Schoenen J. Habituation and migraine. Neurobiol Learn Mem 92(2,2009):249-259; COPPOLA G, Iacovelli E, Bracaglia M, Serrao M, Di Lorenzo C, Pierelli F. Electrophysiological correlates of episodic migraine chronification: evidence for thalamic involvement. J Headache Pain 14(1,2013):76, pp. 1-8; de TOMMASO M, Lo Sito L, Di Fruscolo O, Sardaro M, Pia Prudenzano M, Lamberti P, Livrea P. Lack of habituation of nociceptive evoked responses and pain sensitivity during migraine attack. Clin Neurophysiol 116(6,2005):1254-1264; VALERIANI M, de Tommaso M, Restuccia D, Le Pera D, Guido M, Iannetti G D, Libro G, Truini A, Di Trapani G, Puca F, Tonali P, Cruccu G. Pain 105(1-2,2003):57-64. Reduced habituation to experimental pain in migraine patients: a CO(2) laser evoked potential study; Neelam VANEY, Abhinav Dixit, Tandra Ghosh, Ravi Gupta, M. S. Bhatia. Habituation of event related potentials: a tool for assessment of cognition in headache patients. Delhi Psychiatry Journal 1(1,2008):48-51].

Generally, the devices shown in FIG. 1B will also be used to directly stimulate the vagus nerve, in addition to, or instead of, stimulating sensory nerves within the skin. As described below and in co-pending, commonly assigned patent application U.S. Ser. No. 13/222,087, entitled Devices and methods for non-invasive capacitive electrical stimulation and their use for vagus nerve stimulation on the neck of a patient, to SIMON et al. (which is hereby incorporated by reference), Applicant has developed a stimulator device that can noninvasively stimulate a vagus nerve directly in the patient's neck, without producing cutaneous discomfort to a patient. When the vagus nerve is being stimulated by the device, the quality of sensation in the patient's skin above the vagus nerve depends strongly on the stimulation current and frequency, such that when the currents are not much greater than the perception threshold, the cutaneous sensations may be described as tingle, itch, vibration, buzz, touch, pressure, or pinch. For situations in which the skin is being stimulated with a constant current and with a particular type of stimulation waveform that is described below, any such cutaneous sensation may be ignored by the patient, and the stimulator does not serve as an exteroceptive biofeedback device. In that case, the device resembles instead a physiological control device that may be used to stimulate structures of the central nervous system and/or "Other physiological systems", via stimulation of the vagus nerve, as indicated in FIG. 1B. The particular structures of the central nervous system or other physiological systems that are affected by the vagus nerve stimulation depend on the parameters of the vagus nerve stimulation, which are selected to stimulate the particular system. Direct electrical stimulation of the vagus nerve will itself generate evoked potentials, as the resulting vagal action potentials and their sequelae propagate within the central nervous system.

In certain aspects of the invention, the measurement of an evoked potential as described above may be used to optimize non-invasive stimulation of the vagus nerve with, for example, one of the devices described below. Given that a particular evoked potential can be quantified that represents stimulation of the vagus nerve, the operator can use this measurement to confirm that the action potentials have been created in the vagus nerve during electrical stimulation. In this manner, the operator may, for example, vary a characteristic of the electrical impulses generator by the vagus nerve stimulator in order to ensure that such stimulation is effectively stimulating the vagus nerve at a therapeutic level. For example, if such stimulation does not initially generate the evoked potentials that would confirm the firing of the action potentials in the vagus nerve, the operator may vary aspects of the signal, such as the amplitude, frequency, pulse width and/or duty cycle until such an evoked potential is generated. In addition or alternatively, the operator may vary the placement or orientation of the device on the subject's neck to ensure proper stimulation of the vagus nerve. As another alternative, the operator may position the vagal nerve stimulator on the other side of the patient's neck (left to right or vice versa) in an attempt to optimize the stimulation.

One application of direct vagus nerve stimulation at the neck is to modulate neurotransmitter levels within the central nervous system of patients with certain medical disorders such as primary headache (e.g., migraine), or fibromyalgia, who have a demonstrable habituation deficit with regard to their evoked potentials. Thus, the patient may be tested (without feedback or biofeedback) by stimulating "other sense organs" or the cervical cutaneous senses in FIG. 1B, and measuring the corresponding evoked potentials, over an extended period of time (e.g., visual, auditory, or traditional somatosensory EPs, as reviewed in COPPOLA G, Pierelli F, Schoenen J. Habituation and migraine. Neurobiol Learn Mem 92(2,2009):249-259). The patients who do not exhibit significant habituation in their evoked potentials, in response to the sensory stimulation over a prolonged period of time, are then subjected to an acute direct stimulation of the vagus nerve. The patient is then retested (again without feedback or biofeedback) by stimulating "other sense organs" and re-measuring the previously-measured evoked potentials (visual, auditory, or traditional somatosensory EPs). For some of the individuals (the "responders"), the effect of the intervening acute vagus nerve stimulation is to significantly reduce the magnitude of features of evoked potentials, thereby artificially effecting a form of EP habituation. Those individuals are therefore candidates for chronic treatment of their migraine headaches, by performing the vagus nerve stimulation on a regular basis, with the objective of reducing the duration, frequency and severity of symptoms associated with the disorder (e.g., migraine attacks, pain associated with fibromyalgia, etc). Methods for doing so were disclosed in the co-pending, commonly assigned patent application U.S. Ser. No. 13/109,250, entitled Electrical and magnetic stimulators used to treat migraine/sinus headache and comorbid disorders, to SIMON et al, and U.S. Ser. No. 13/183,721 entitled Electrical and magnetic stimulators used to treat migraine/sinus headache, rhinitis, sinusitis, rhinosinusitis, and comorbid disorders, to SIMON et al. On the other hand, some individuals (the "non-responders") may exhibit no significant changes to the magnitude of features of their evoked potentials following acute stimulation of their vagus nerve. It may be decided on the basis of this outcome that the "non-responders" are candidates for treatment by methods other than performing vagus nerve stimulation on a regular basis [OZKUL Y, Bozlar S. Effects of fluoxetine on habituation of pattern reversal visually evoked potentials in migraine prophylaxis. Headache 42(7,2002):582-587].

Vagus nerve stimulation may also be useful for the treatment of patients irrespective of whether the patient exhibits a deficit in the habituation of evoked potentials, and irrespective of whether the vagus nerve stimulation promotes the normalization of habituation of evoked potentials. In migraineurs, for example, the likely usefulness of the vagus nerve stimulation may more generally be based primarily upon the baseline characteristics of an evoked potential, measured during one or more phases of the migraine headache, particularly during the interictal phase. In fact, it is preferable to perform the measurements during multiple times throughout the interictal phase, in view of the changes in the evoked potential that occur throughout that phase. A method for using previously measured values of characteristics of the baseline evoked potential, to infer the likelihood of therapeutic success, is as follows. If the migraine attack is in progress, noninvasive vagus nerve stimulation is administered, and its effect on the reduction of headache pain is measured. The pain measurement may be based on self-reporting of the patient, or it may be based on an objective physiological measurement of pain. The measurement of pain may also be made following stimulation with multiple sets of vagus nerve stimulation parameters, in order to evaluate the stimulation parameters that have the greatest effect on the reduction of pain. After vagus nerve stimulation, the evoked potential may be measured again, and the features of the baseline evoked potential may then be compared with features of the post-stimulation evoked potential. Changes in the evoked potential may involve differences in amplitudes and latencies of peaks and troughs, which are of potential predictive value. When such measurements are performed on populations of migraineurs and control normal individuals, statistical methods may then be used to determine which features of the pre- and post-stimulation evoked potentials, as well as their differences, are most closely related to the reduction of pain in the migraineur. The statistical methods may also be used to predict which parameters of the vagus nerve stimulation have the greatest effect on the reduction of pain and on the features of the pre- and post-stimulation evoked potentials. The vagus nerve stimulation may then be re-applied to the patient, with a different set of stimulation parameters, selected on the basis of the relation between those parameters and pain reduction, as well as on characteristics of the pre- and/or post-stimulation evoked potentials.

The vagus nerve stimulation may also be used as a prophylaxis to reduce the frequency or severity of migraine attacks. In that case, the vagus nerve stimulation is applied to the patient over a prolonged period of time, and its quantitative effects on the frequency and severity of the migraine attacks is measured. When such measurements are performed on populations of migraineurs and control normal individuals, statistical methods may then be used to determine which features of the initial pre- and post-stimulation evoked potentials, as well as their differences, are most closely related to reduction in the chronic frequency and severity of migraine attacks. Thereafter, the likelihood that vagus nerve stimulation will be successful in treating a migraineur chronically may be inferred from the measured features of his/her initial pre- and post-stimulation evoked potentials, as well as differences between the pre- and post-stimulation evoked potentials.

Although the electrical stimulation embodiment described in the previous paragraph does not make use of a cutaneous biofeedback signal, in other embodiments, the patient may nevertheless become conscious of direct stimulation of the vagus nerve, as an artificial interoceptive sensation. Interoceptive sensations from the body's interoceptors are conveyed to, and represented in, the brain's right anterior insula and related structures, at which locations the individual may be conscious of interoceptive activity. As described below, some of the neural pathways leading to the insula involve afferent fibers of the vagus nerve. Interoceptors within the body may convey naturally-occurring interoceptive signals via vagal afferent fibers, but in the present invention, electrical stimulation of the vagus nerve may also produce artificial interoceptive signals. Thus, the present invention contemplates the stimulation of vagal afferent fibers in such a way that the patient may sense the stimulation as an internal bodily signal, even though the signals are not produced by interoceptors. When the artificial interoceptive signals are varied by the nerve stimulator as a function of the output of a physiological sensor or some feature of an evoked potential waveform, the individual may consciously respond to the artificial interoceptive signals as though they were a biofeedback signal. This is despite the fact that the signals are not conventional biofeedback signals, because they are not presented to an exteroceptive sense.

In a commonly-assigned, co-pending application, (Ser. No. 14/071,577, entitled Nerve Stimulator System, filed Nov. 4, 2013) Applicants disclosed the implantation and use of minimally invasive cervical vagus nerve stimulators. For such stimulators, the cutaneous (e.g. tactile) stimulation shown in FIG. 1B is not feasible unless additional skin-surface electrodes were to be applied to the subject. Nevertheless, in such applications, the individual may also consciously respond to the artificial interoceptive signals that are applied through the minimally invasive vagus nerve stimulator, as though they were a biofeedback signal. Otherwise, the biofeedback methods that are disclosed herein would have to be performed using sensory modalities that do not involve cervical electrical stimulation, for example, by using auditory or visual biofeedback that is produced through the "Other Sensory Stimuli" component of FIG. 1B.

In a more general embodiment of the system shown in FIG. 1B, a cutaneous biofeedback signal may be superimposed upon the electrical stimulation waveform that preferentially stimulates the vagus nerve directly. Thus, in addition to the mechanisms described in the previous two paragraphs, the stimulation waveform may also contain a time-varying signal with frequency components that are designed specifically to stimulate cutaneous nerves. The biofeedback signal will vary as a function of the physiological parameter that is being sensed by the physiological sensor (e.g., evoked potential feature or skin conductance level). The biofeedback signal may be a continuous analog signal, or it may be a digital signal, e.g., with three discrete intensity levels and three discrete long-pulse durations that can be discriminated.

The patient may then consciously respond to the biofeedback signal, for example, by relaxing or tensing skeletal muscles or by eliciting a relaxing or agitated emotional response, thereby modulating the tone of the sympathetic nervous system [COSTA F, Biaggioni I. Role of adenosine in the sympathetic activation produced by isometric exercise in humans. J Clin Invest. 93(1994):1654-1660; KREIBIG S D. Autonomic nervous system activity in emotion: a review. Biol Psychol 84 (3,2010):394-421].

The three mechanisms illustrated in FIG. 1B (biofeedback, artificial interoceptive sensation, and direct stimulation via the vagus nerve) will collectively modulate the central nervous system or other physiological systems, interacting with one another to determine the value of the sensed physiological signal or feature of the evoked potential. Part of the interaction is determined by the manner in which the vagus nerve stimulator/biofeedback device/feedback controller is programmed. For example, direct stimulation of the physiological system via the vagus nerve may be programmed to follow and amplify or enhance changes that occur as a result of biofeedback. An embodiment of that example would occur when the individual uses galvanic skin response biofeedback alone to consciously reduce sympathetic tone through muscular and emotional modulation, whereupon the device in FIG. 1B senses that reduction through its programming and then amplifies the effect by increasing parasympathetic tone after a brief time delay, by directly stimulating vagal parasympathetic efferent nerve fibers.

In this example, it is clear what the biofeedback effect is initially (reduction of sympathetic tone), and the vagus stimulation is only applied thereafter to amplify it (stimulation of vagal parasympathetic fibers). In other embodiments that are disclosed herein, both biofeedback and vagus nerve stimulation are performed simultaneously, and mathematical modeling is used to infer the effects that are due to the biofeedback, thereby allowing the device to also infer the intentions of the individual and apply the vagus nerve stimulation accordingly. Consequently, the whole device shown in FIG. 1B has more functionality than its individual parts simply added together.

In certain embodiments, the system comprises software and hardware components to fix the parameters of the electrical impulses after they have been optimized. In one aspect, feedback provided by the physiological sensor optimizes the signal applied to the nerve. Once the signal has been optimized, the software and hardware components of the system fix the electrical impulse based on the parameters that have been sensed by the physiological sensor. The signal generator will then apply the fixed electrical impulse to the patient. For example, the physician may be able to optimize the electrical impulse in the hospital or office setting by applying electrical impulses and measuring their effect on certain body parameters. The impulses can then be varied either manually or automatically until the effect is optimized. If the stimulator is implanted, the signal generator may automatically apply the optimized electrical impulse to the patient at certain times throughout the day, or it may be designed to only apply the electrical impulses when activated by the patient. If the stimulator is a non-invasive device, the patient self-treats and applies the optimized electrical impulses according to the treatment algorithm set up by the physician.

There is little prior art involving both vagus nerve stimulation and biofeedback devices, where the term "biofeedback device" means here essentially what is defined in 21 CFR 882.5050: "a biofeedback device is an instrument that provides a visual or auditory signal [or other such exteroceptive signal] corresponding to the status of one or more of a patient's physiological parameters (e.g., brain alpha wave activity, muscle activity, skin temperature, etc.) so that the patient can control voluntarily these physiological parameters . . . ." The term biofeedback appears in the text of some patents or patent applications, but often with a different meaning than what is meant here. Examples of such different usages of the term are as follows. U.S. Pat. No. 7,657,310, entitled Treatment of reproductive endocrine disorders by vagus nerve stimulation, to BURAS, uses the term biofeedback to refer to feedback of a signal that has been transduced from a patient's body, but not voluntary mental control over such a signal. U.S. Pat. No. 8,509,902, entitled Medical device to provide breathing therapy, to CHO et al., discloses devices and methods that are said to involve biofeedback, but in fact, their invention is not concerned with voluntary control over a biofeedback signal because it "relates generally to the use of diaphragm contraction prolongation during breathing therapy sessions (e.g., when a patient is not cognitive of respiratory control, such as when they are sleeping) . . . " U.S. Pat. No. 7,946,976, entitled Methods and devices for the surgical creation of satiety and biofeedback pathways, to GERTNER, uses the term biofeedback to mean an internal bodily control signal, not the voluntary control over a biofeedback signal derived from a physiological measurement. Patent application US20050149142, entitled Gastric stimulation responsive to sensing feedback, to STARKEBAUM, uses the term biofeedback to mean artificially-produced symptoms of gastroparesis that are caused by electrical stimulation of the stomach.

However, some patents or patent applications do use the term biofeedback in the sense that is intended here and also mention vagus nerve stimulation. Application US 20120071731, entitled System and method for physiological monitoring, to GOTTESMAN, describes the use of a physiological sensor that can be used in a biofeedback application and that can also be used to determine when to stimulate a vagus nerve. However, the biofeedback and vagus nerve stimulation uses of the sensor are described as being different applications. Similarly, U.S. Pat. No. 8,036,736, entitled Implantable systems and methods for identifying a contraictal condition in a subject, to SNYDER et al., is concerned with the analysis of physiological signals for purposes of automatic identification of circumstances under when an epilepsy patient should undertake therapy. SNYDER mentions vagus nerve stimulation and biofeedback techniques as two such alternative therapies, but not as methods that should be performed together.

Patent application US 20100004705, entitled Systems, Methods and devices for treating tinnitus, to KILGARD et al. and US 20100003656, entitled Systems, methods and devices for paired plasticity, to KILGARD et al, also apparently use the term biofeedback in the sense that is intended here. They describe the simultaneous use of electrical neural stimulation with biofeedback therapy (among other therapies), including the use of invasive vagus nerve stimulation. However, according to KILGARD et al., the disclosed relation between the biofeedback therapy and neural stimulation relates only to their mutual timing. There is nothing in their application to suggest that the actual parameters of the nerve stimulation are to be modulated in conjunction with the strength of the biofeedback signal itself or of the physiological signal that serves as the basis of the biofeedback signal. Furthermore, in that patent application, the electrical stimulation and biofeedback signals are described as being distinct entities, wherein the electrical stimulation is shown in the figures there to be an invasive procedure, and biofeedback is generally understood to be a noninvasive procedure. This is in contrast to the present invention, in which the electrical stimulation itself may comprise the biofeedback signal, and in which both the electrical nerve stimulation and biofeedback methods are noninvasive procedures. Also, according to KILGARD et al, the electrical stimulation is said to induce plasticity in the brain, e.g., via activation of the nucleus basalis, locus coeruleus, or amygdala, thereby enhancing efficacy of the biofeedback therapy. However, the present invention does not necessarily involve neuronal plasticity, and the present invention may also produce stimulation of the nucleus basalis, locus coeruleus, amygdala, and many other brain components, without inducing plasticity. Furthermore, the present invention is different from all of the above-mentioned patents concerning biofeedback involving the vagus nerve in that the present biofeedback methods and devices involve the measurement of evoked potentials.

Description of the Noninvasive Nerve Stimulating/Modulating Devices

Figure 2:
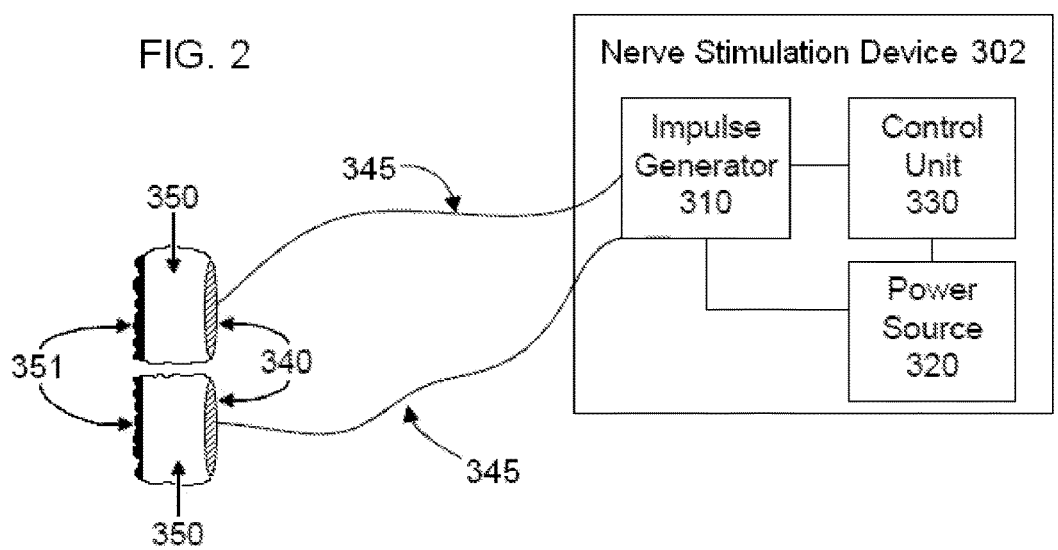
FIG. 2 shows a schematic view of nerve modulating devices according to the present invention, which supply controlled pulses of electrical current to body-surface electrodes.

Devices of the present invention are able to stimulate a vagus nerve, as well as the skin above the nerve, as now described. An embodiment of the present invention is shown in FIG. 2, which is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to the impulse generator 310. In a preferred embodiment, the same impulse generator 310, power source 320, and control unit 330 may be used for either a magnetic stimulator or the electrode-based stimulator 302, allowing the user to change parameter settings depending on whether magnetic coils or the electrodes 340 are attached, either of which may be used for the therapeutic stimulation applications that are describe herein [application Ser. No. 13/183,765 and Publication US2011/0276112, entitled Devices and methods for non-invasive capacitive electrical stimulation and their use for vagus nerve stimulation on the neck of a patient, to SIMON et al.; application Ser. No. 12/964,050 and Publication US2011/0125203, entitled Magnetic Stimulation Devices and Methods of Therapy, to SIMON et al, which are hereby incorporated by reference].

Although a pair of electrodes 340 is shown in FIG. 2, in practice the electrodes may also comprise three or more distinct electrode elements, each of which is connected in series or in parallel to the impulse generator 310. Thus, the electrodes 340 that are shown in FIG. 2 represent all electrodes of the device collectively.

The item labeled in FIG. 2 as 350 is a volume, contiguous with an electrode 340, that is filled with electrically conducting medium. The conducting medium in which the electrode 340 is embedded need not completely surround an electrode. The volume 350 is electrically connected to the patient at a target skin surface in order to shape the current density passed through an electrode 340 that is needed to accomplish stimulation of the patient's nerve or tissue such as the skin. The electrical connection to the patient's skin surface is through an interface 351. In one embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, or an electrically conducting or permeable membrane. In that case, electrical coupling of the stimulator to the patient is ohmic. As shown, the interface may be deformable such that it is form-fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous. The control unit 330 controls the impulse generator 310 to generate a signal for each of the device's electrodes (or magnetic coils). The signals are selected to be suitable for amelioration of a particular medical condition, when the signals are applied non-invasively to a target nerve or tissue via the electrodes 340. It is noted that nerve stimulating/modulating device 302 may be referred to by its function as a pulse generator. Patent application publications US2005/0075701 and US2005/0075702, both to SHAFER, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard, computer mouse, and touchscreen, as well as any externally supplied physiological signals (see FIG. 1B), analog-to-digital converters for digitizing externally supplied analog signals such as evoked potentials and physiological signals (see FIG. 1B), communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback, including biofeedback, measured from externally supplied physiological or environmental signals (see FIG. 1B). Alternatively, the control unit 330 may have a compact and simple structure, for example, wherein the user may operate the system using only an on/off switch and power control wheel or knob. In a section below, a preferred embodiment is described wherein the stimulator housing has a simple structure, but other components of the control unit 330 are distributed into other discrete devices (see FIG. 6).

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes, as well as the spatial distribution of the electric field that is produced by the electrodes. The rise time and peak energy are governed by the electrical characteristics of the stimulator and electrodes, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurlo, Przemyslaw Plonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied. The preferred pulse parameters are described in a later section of this application.

Preferred Embodiments of the Electrode-Based Stimulator

The electrodes of the invention are applied to the surface of the neck, or to some other surface of the body, and are used to deliver electrical energy non-invasively to a nerve. The vagus nerve has previously been stimulated non-invasively, using electrodes applied via leads to the surface of the skin. It has also been stimulated non-electrically through the use of mechanical vibration [HUSTON J M, Gallowitsch-Puerta M, Ochani M, Ochani K, Yuan R, Rosas-Ballina M et al (2007). Transcutaneous vagus nerve stimulation reduces serum highmobility group box 1 levels and improves survival in murine sepsis. Crit Care Med 35: 2762-2768; GEORGE M S, Aston-Jones G. Noninvasive techniques for probing neurocircuitry and treating illness: vagus nerve stimulation (VNS), transcranial magnetic stimulation (TMS) and transcranial direct current stimulation (tDCS). Neuropsychopharmacology 35(1,2010):301-316]. However, no such reported uses of noninvasive vagus nerve stimulation were directed to biofeedback applications. Patent No. U.S. Pat. No. 7,340,299, entitled Methods of indirectly stimulating the vagus nerve to achieve controlled asystole, to John D. PUSKAS, discloses the stimulation of the vagus nerve using electrodes placed on the neck of the patient, but that patent is unrelated to biofeedback. Non-invasive electrical stimulation of the vagus nerve has also been described in Japanese patent application JP2009233024A with a filing date of Mar. 26, 2008, entitled Vagus Nerve Stimulation System, to Fukui YOSHIHOTO, in which a body surface electrode is applied to the neck to stimulate the vagus nerve electrically. However, that application is also unrelated to biofeedback. In patent publication US20080208266, entitled System and method for treating nausea and vomiting by vagus nerve stimulation, to LESSER et al., electrodes are used to stimulate the vagus nerve in the neck to reduce nausea and vomiting, but this too is unrelated to biofeedback.

Patent application US2010/0057154, entitled Device and method for the transdermal stimulation of a nerve of the human body, to DIETRICH et al., discloses a non-invasive transcutaneous/transdermal method for stimulating the vagus nerve, at an anatomical location where the vagus nerve has paths in the skin of the external auditory canal. Their non-invasive method involves performing electrical stimulation at that location, using surface stimulators that are similar to those used for peripheral nerve and muscle stimulation for treatment of pain (transdermal electrical nerve stimulation), muscle training (electrical muscle stimulation) and electroacupuncture of defined meridian points. The method used in that application is similar to the ones used in U.S. Pat. No. 4,319,584, entitled Electrical pulse acupressure system, to McCALL, for electroacupuncture; U.S. Pat. No. 5,514,175 entitled Auricular electrical stimulator, to KIM et al., for the treatment of pain; and U.S. Pat. No. 4,966,164, entitled Combined sound generating device and electrical acupuncture device and method for using the same, to COLSEN et al., for combined continuous and monotonous sound/electroacupuncture. A related application is US2006/0122675, entitled Stimulator for auricular branch of vagus nerve, to LIBBUS et al. Similarly, U.S. Pat. No. 7,386,347, entitled Electric stimulator for alpha-wave derivation, to CHUNG et al., described electrical stimulation of the vagus nerve at the ear. Patent application US2008/0288016, entitled Systems and Methods for Stimulating Neural Targets, to AMURTHUR et al., also discloses electrical stimulation of the vagus nerve at the ear. U.S. Pat. No. 4,865,048, entitled Method and apparatus for drug free neurostimulation, to ECKERSON, teaches electrical stimulation of a branch of the vagus nerve behind the ear on the mastoid processes, in order to treat symptoms of drug withdrawal. KRAUS et al described similar methods of stimulation at the ear [KRAUS T, Hosl K, Kiess O, Schanze A, Kornhuber J, Forster C (2007). BOLD fMRI deactivation of limbic and temporal brain structures and mood enhancing effect by transcutaneous vagus nerve stimulation. J Neural Transm 114: 1485-1493]. However, none of the disclosures in these patents or patent applications for electrical stimulation of the vagus nerve near the ear are used to in connection with biofeedback.

Embodiments of the present invention may differ with regard to the number of electrodes that are used, the distance between electrodes, and whether disk or ring electrodes are used. In preferred embodiments of the method, one selects the electrode configuration for individual patients, in such a way as to optimally focus electric fields and currents onto the selected nerve, without generating excessive currents on the surface of the skin. This tradeoff between focality and surface currents is described by DATTA et al. [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174]. Although DATTA et al. are addressing the selection of electrode configuration specifically for transcranial current stimulation, the principles that they describe are applicable to peripheral nerves as well [RATTAY F. Analysis of models for extracellular fiber stimulation. IEEE Trans. Biomed. Eng. 36 (1989): 676-682].

A preferred embodiment of an electrode-based stimulator is shown in FIG. 3. As shown, the stimulator (30) comprises two heads (31) and a connecting part that joins them. Each head (31) contains a stimulating electrode. The connecting part of the stimulator contains the electronic components and a battery (not shown) that are used to generate the signals that drive the electrodes. However, in other embodiments of the invention, the electronic components that generate the signals that are applied to the electrodes may be separate, but connected to the electrode head (31) using wires or wireless communication with the heads. Furthermore, other embodiments of the invention may contain a single such head or more than two heads.

Heads of the stimulator (31) are applied to a surface of the patient's body, during which time the stimulator may be held in place by straps or frames or collars, or the stimulator may be held against the patient's body by hand. In either case, the level of stimulation power may be adjusted with a wheel (34) that also serves as an on/off switch. A light (35) is illuminated when power is being supplied to the stimulator. An optional cap may be provided to cover each of the stimulator heads (31), to protect the device when not in use, to avoid accidental stimulation, and to prevent material within the head from leaking or drying. Thus, in this embodiment of the invention, mechanical and electronic components of the stimulator (impulse generator, control unit, and power source) are compact, portable, and simple to operate.

Figure 4A:
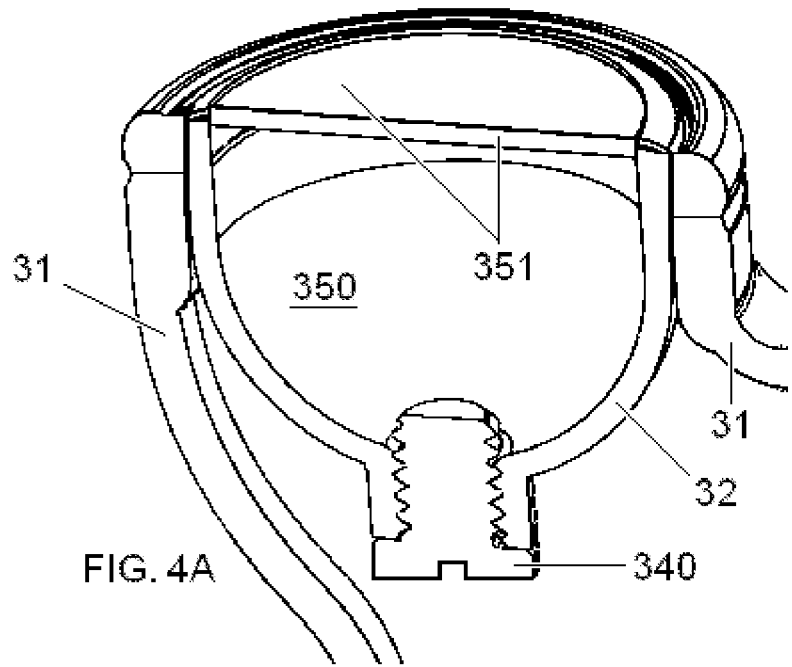
FIGS. 4A-4B show an assembled (FIG. 4A) and expanded (FIG. 4B) view of one of the stimulator heads that were shown in FIGS. 3A-3C.
Figure 4B:
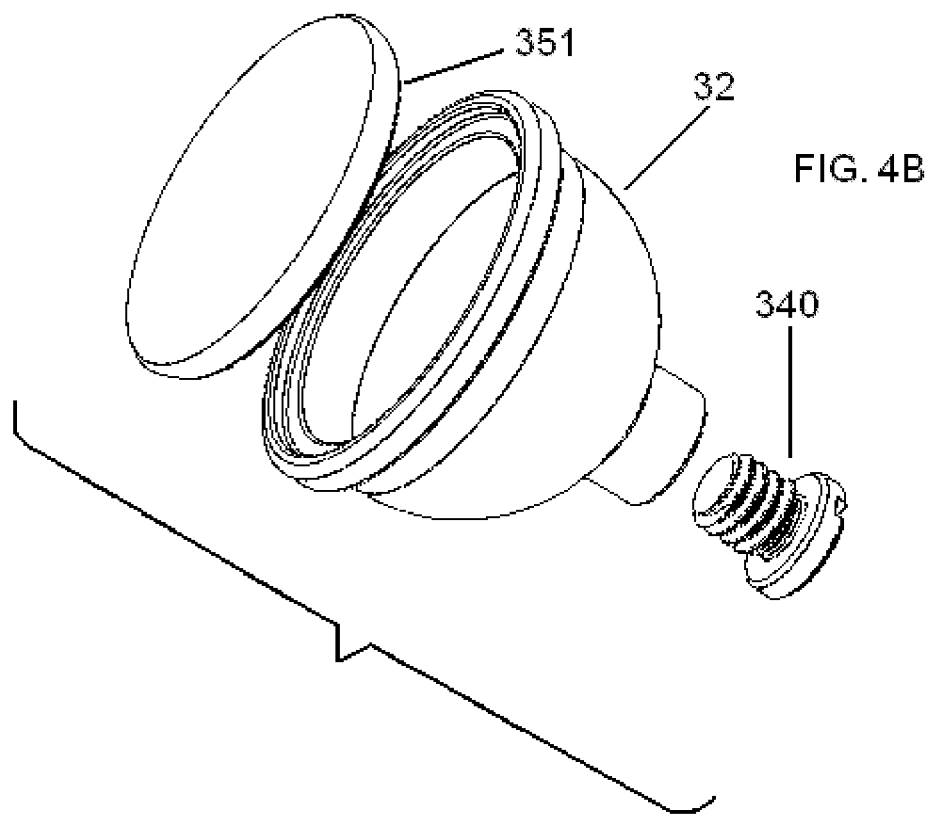
Figure 5A:
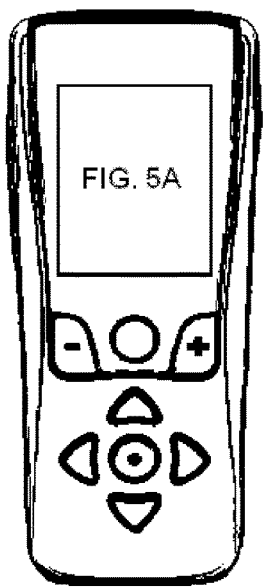
FIGS. 5A-5D show some types of devices that may communicate with the docking station and/or stimulator shown in FIG. 3, comprising a remote control (FIG. 5A), a mobile phone (FIG. 5B), a touchscreen device (FIG. 5C), and a laptop computer (FIG. 5D).
Figure 5C:
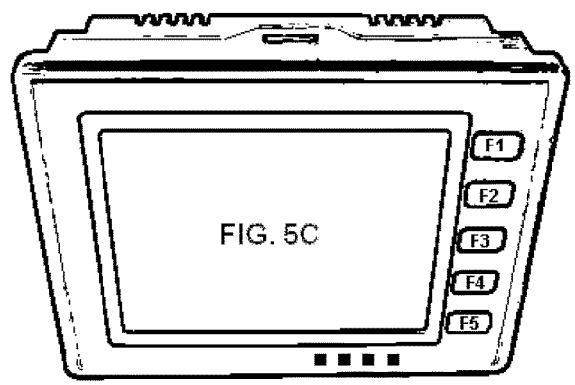
Figure 5B:
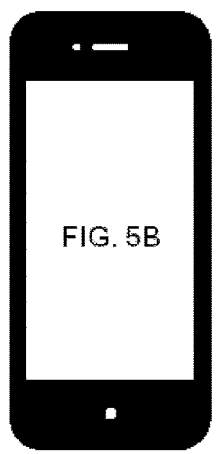
Figure 5D:
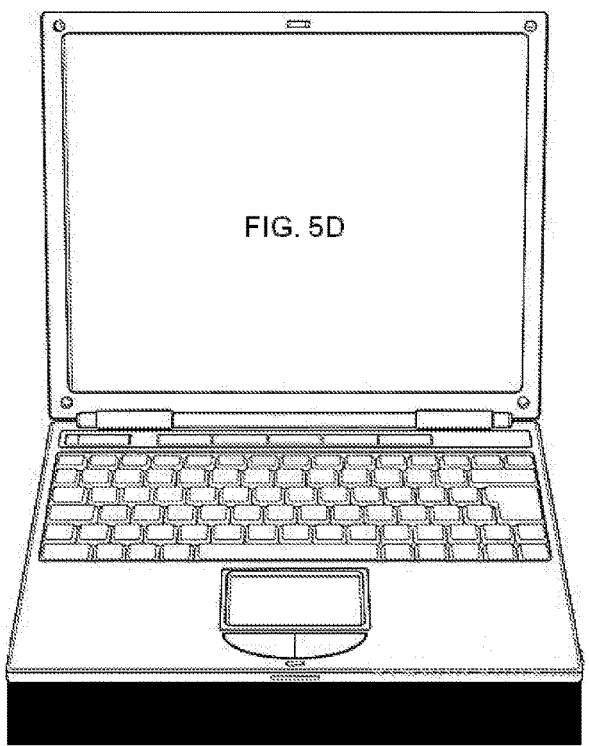

Details of preferred embodiments of the stimulator heads are described in co-pending, commonly assigned applications that were cited in the section Cross Reference to Related Applications. As described in those applications, the stimulator designs situate the electrodes of the stimulator (340 in FIG. 2) remotely from the surface of the skin, within a chamber that is filled with conducting material (350 in FIG. 2). Thus, the conducting material is placed in a chamber between the electrode and the exterior component of the stimulator head that contacts the skin (351 in FIG. 2), thereby allowing for current to pass from the electrode to the skin. An embodiment of a stimulator head 31 is shown in FIG. 4. FIG. 4A shows a section through one of the two stimulator heads 31 that are shown in FIG. 3. The outer structure of the stimulator head 31 supports the chamber 32 that is filled with conducting material 350. The electrode 340 is shown in FIG. 4A to be a conducting metal screw, to which a wire (345 in FIG. 2) from the stimulator's impulse generator (310 in FIG. 2) is attached. The interface 351 of the stimulator head, which contacts the surface of the skin, is shown in FIG. 4A to comprise a disc that is made of a conducting metal, such as stainless steel. Assembly of the interface 351, chamber 32, and electrode 340 is illustrated in FIG. 4B with an exploded view. The conducting material 350 may be added to the chamber 32 before the electrode 340 is screwed into the chamber 32.

One of the novelties of such a design is that the stimulator, along with a correspondingly suitable stimulation waveform (see below), shapes the electric field, producing a selective physiological response by stimulating that nerve, but avoiding substantial stimulation of nerves and tissue other than the target nerve, particularly avoiding the stimulation of nerves that produce pain. The design may, however, stimulate tactile nerves of the skin by superimposing stimulation waveforms that are directed individually to the deep nerve and to the skin nerves. The shaping of the electric field is described in terms of the corresponding electromagnetic field equations in co-pending, commonly assigned application US20110230938 (application Ser. No. 13/075,746), entitled Devices and methods for non-invasive electrical stimulation and their use for vagal nerve stimulation on the neck of a patient, to SIMON et al., which is hereby incorporated by reference.

Significant portions of the control unit (330 in FIG. 2) of the vagus nerve stimulator may reside in controller components that are physically separate from the housing of the stimulator (30 in FIG. 3). In such embodiments, separate components of the controller and stimulator housing may generally communicate with one another wirelessly. Thus, the use of wireless technology avoids the inconvenience, size constraints, and distance limitations of interconnecting cables. A more complete rationale for physically separating components of the control unit is provided in a commonly assigned, co-pending application entitled MEDICAL SELF-TREATMENT USING NON-INVASIVE VAGUS NERVE STIMULATION, to SIMON et al., which is hereby incorporated by reference.

Accordingly, an embodiment of the invention includes a docking station (40 in FIG. 3C) that may also be used as a recharging power supply for the stimulator housing (30 in FIG. 3). The docking station may send/receive data to/from the stimulator housing, and may send/receive data to/from databases and other components of the system, including those that are accessible via the internet. Thus, prior to any particular stimulation session, the docking station may load into the stimulator parameters of the session, including stimulation waveform parameters.

In a preferred embodiment, the docking station also limits the amount of stimulation energy that may be consumed by the patient in the stimulation session, by charging the stimulator's rechargable battery with only a specified amount of releasable electrical energy. Note that this is generally different than setting a parameter to restrict the duration of a stimulation session. As a practical matter, the stimulator may therefore use two batteries, one for stimulating the patient (the charge of which may be limited by the docking station) and the other for performing other functions such as data transmission. Methods for evaluating a battery's charge or releasable energy are known in the art, for example, in U.S. Pat. No. 7,751,891, entitled Power supply monitoring for an implantable device, to ARMSTRONG et al. Alternatively, control components within the stimulator housing may monitor the amount of stimulation energy that has been consumed during a stimulation session and stop the stimulation session when a limit has been reached, irrespective of the time when the limit has been reached.

Refer now to the docking station that is shown as item 40 in FIG. 3C. The stimulator housing 30 and docking station 40 can be connected to one another by inserting the connector 36 near the center of the base 38 of the stimulator housing 30 into a mated connector 42 of the docking station 40. As shown in FIG. 3, the docking station 30 has an indentation or aperture 41 that allows the base 38 of the stimulator housing 30 to be seated securely into the docking station. The connector 36 of the stimulator housing is recessed in an aperture 37 of the base of the stimulator housing 30 that may be covered by a detachable or hinged cover when the stimulator housing is not attached to the docking station (not shown).

The mated connectors 36 and 42 have a set of contacts that have specific functions for the transfer of power to charge a rechargable battery in the stimulator housing 30 and to transfer data bidirectionally between the stimulator housing and docking station. As a safety feature, the contacts at the two ends of the mated connector are connected to one another within the stimulator housing and within the docking station, such that if physical connection is not made at those end contacts, all the other contacts are disabled via active switches. Also, the connectors 36 and 42 are offset from the center of the base 38 of the stimulator housing 30 and from the center of the indentation or aperture 41 of the docking station 40, so that the stimulator housing can be inserted in only one way into the docking station. That is to say, when the stimulator housing 30 is attached to the docking station 40, the front of the stimulator housing 30 must be on the front side of the docking station 40. As shown, the back side of the docking station has an on/off switch 44 and a power cord 43 that attaches to a wall outlet. The docking station 40 also has ports (e.g., USB ports) for connecting to other devices, one of which 45 is shown on the side of the station, and others of which are located on the front of the station (not shown). The front of the docking station has colored lights to indicatate whether the docking station has not (red) or has (green) charged the stimulator so as to be ready for a stimulation session.

Through cables to the communication port 45, the docking station 40 can communicate with the different types of devices, such as those illustrated in FIG. 5. Handheld devices may resemble conventional remote controls with a display screen (FIG. 5A) or mobile phones (FIG. 5B). Other type of devices with which the docking station may communicate are touchscreen devices (FIG. 5C) and laptop computers (FIG. 5D). As described below, such communication may also be performed wirelessly.

Figure 6:
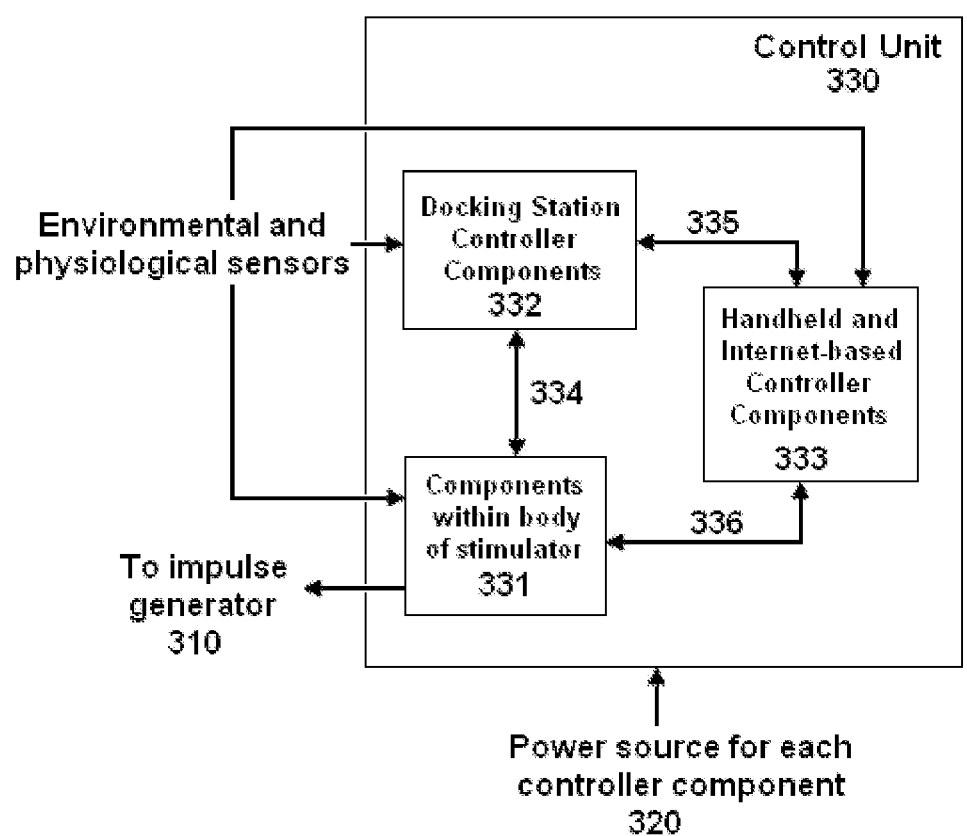
FIG. 6 shows an expanded diagram of the control unit shown in FIG. 2, separating components of the control unit into those within the body of the stimulator, those within the docking station, and those within hand-held and internet-based devices, also showing communication paths between such components.

The communication connections between different components of the stimulator's controller are shown in FIG. 6, which is an expanded representation of the control unit 330 in FIG. 2. Connection between the docking station controller components 332 and components within the stimulator housing 331 is denoted in FIG. 6 as 334. For example, that connection is made when the stimulator housing is connected to the docking station as described above. Connection between the docking station controller components 332 and devices 333 such as those shown in FIG. 5 (generally internet-based components) is denoted as 335. Connection between the components within the stimulator housing 331 and devices 333 such as those shown in FIG. 5 (generally internet-based components) is denoted as 336. Different embodiments of the invention may lack one or more of the connections. For example, if the connection between the stimulator housing and the devices 333 is only through the docking station controller components, then in that embodiment of the invention, only connections 334 and 335 would be present.

The connections 334, 335 and 336 in FIG. 6 may be wired or wireless. For example, if the controller component 333 is the mobile phone shown in FIG. 5B, the connection 335 to a docking stationport (45 in FIG. 3) could be made with a cable to the phone's own docking port. Similarly, if the controller component 333 is the laptop computer shown in FIG. 5D, the connection 335 to a docking stationport (45 in FIG. 3) could be made with a cable to a USB port on the computer. However, the preferred connections 334, 335, and 336 will be wireless.

Although infrared or ultrasound wireless control might be used to communicate between components of the controller, they are not preferred because of line-of-sight limitations. Instead, in the present disclosure, the communication between devices preferably makes use of radio communication within unlicensed ISM frequency bands (260-470 MHz, 902-928 MHz, 2400-2.4835 GHz). Components of a radio frequency system in devices 331, 332, and 333 typically comprise a system-on-chip transciever with an integrated microcontroller; a crystal; associated balun & matching circuitry, and an antenna [Dag GRINI. R F Basics, R F for Non-RF Engineers. Texas Instruments, Post Office Box 655303, Dallas, Tex. 75265, 2006].

Transceivers based on 2.4 GHz offer high data rates (greater than 1 Mbps) and a smaller antenna than those operating at lower frequencies, which makes them suitable for with short-range devices. Furthermore, a 2.4 GHz wireless standard (Bluetooth, Wi-Fi, and ZigBee) may be used as the protocol for transmission between devices. Although the ZigBee wireless standard operates at 2.4 GHz in most jurisdictions worldwide, it also operates in the ISM frequencies 868 MHz in Europe, and 915 MHz in the USA and Australia. Data transmission rates vary from 20 to 250 kilobits/second with that standard.

FIG. 6 also shows that sensor devices that measure physiological and environmental signals may connect to the control unit 330 via any of its subsystems (stimulator body 331, docking station 332, and handheld or internet-based devices 333). Because many commercially available health-related sensors may operate using ZigBee, its use may be recommended for applications in which the controller adjusts the patient's vagus nerve stimulation based on the physiological sensors' values, as described in connection with FIG. 1 [ZigBee Wireless Sensor Applications for Health, Wellness and Fitness. ZigBee Alliance 2400 Camino Ramon Suite 375 San Ramon, Calif. 94583]. Systems for connecting smartphones to physiologial sensors using Bluetooth may also be used. For example, BioZen, which is designed specifically for biofeedback applications, is based on the open source framework Bluetooth Sensor Processing for Android smartphones and is freely available. It may connect wirelessly to many commercially available physiological sensor devices [Anonymous. BIOZEN User's Manual. United States Defense Department National Center for Telehealth and Technology. 9933 West Hayes Street, Joint Base Lewis-McChord, Wash. 98431, pp. 1-16, 2013]. Commercially available wired and wireless physiological sensor measurement devices using the e-Health Sensor Platform for Arduino and Raspberry Pi are also suitable for incorporation into, or connection with, the stimulator housing 30 or the docking station 40 in FIG. 3 [Anonymous. e-Health Sensor Platform for Arduino and Raspberry Pi (Biometric/MedicalApplications). Technical literature from Cooking Hacks (the open hardware division of Libelium). Libelium Comunicaciones Distribuidas S. L., C/Maria de Luna 11, nave 17, C. P. 50018, Zaragoza, Spain. pp. 1-159, 2013]. Other such methods for incorporating physiological sensors into biofeedback systems have also been described [Guan-Zheng L I U, Bang-Yu Huang and Lei Wang. A Wearable Respiratory Biofeedback System Based on Generalized Body Sensor Network. TELEMEDICINE and e-HEALTH 17(5,2011):348-357]. Use of such sensors is described more completely below in a section on the use of biofeedback and automatic control theory methods to improve treatment of individual patients.

Application of the Stimulator to the Neck of the Patient

In different methodological embodiments of the present invention, selected nerve fibers are stimulated by the disclosed electrical stimulation devices. These methods include noninvasive stimulation at a particular location on the patient's neck. Nerves stimulated at that location comprise the vagus nerve, and in some embodiments, cutaneous nerve endings. At that location in the neck, the vagus nerve is situated within the carotid sheath. The left vagus nerve is sometimes selected for stimulation, because stimulation of the right vagus nerve may produce undesired effects on the heart. However, depending on the application, the right vagus nerve or both right and left vagus nerves may be stimulated instead.

To find the appropriate location to stimulate on the neck, the location of the carotid sheath will first be ascertained by any method known in the art, e.g., by feel and anatomical inference, or preferably by ultrasound imaging [KNAPPERTZ V A, Tegeler C H, Hardin S J, McKinney W M. Vagus nerve imaging with ultrasound: anatomic and in vivo validation. Otolaryngol Head Neck Surg 118(1,1998):82-85; GIOVAGNORIO F and Martinoli C. Sonography of the cervical vagus nerve: normal appearance and abnormal findings. AJR Am J Roentgenol 176(3,2001):745-749]. The stimulator is then positioned at the level of about the fifth to sixth cervical vertebra.

FIG. 7 illustrates application of the device 30 shown in FIG. 3 to the patient's neck, in order to stimulate the cervical vagus nerve on that side of the neck. For reference, FIG. 7 shows the locations of the following vertebrae: first cervical vertebra 71, the fifth cervical vertebra 75, the sixth cervical vertebra 76, and the seventh cervical vertebra 77.

FIG. 8 shows the stimulator 30 applied to the neck of a child, which is partially immobilized with a foam cervical collar 78 that is similar to ones used for neck injuries and neck pain. The collar is tightened with a strap 79, and the stimulator is inserted through a hole in the collar to reach the child's neck surface. As shown, the stimulator is turned on and off with a control knob, and the amplitude of stimulation may also be adjusted with the control knob that is located on the stimulator. In other models, the control knob is absent or disabled, and the stimulator may be turned on and off remotely, using a wireless controller (see FIG. 5A) that may be used to adjust the stimulation parameters of the controller (e.g., on/off, stimulation amplitude, stimulation waveform frequency, etc.).

Figure 10:
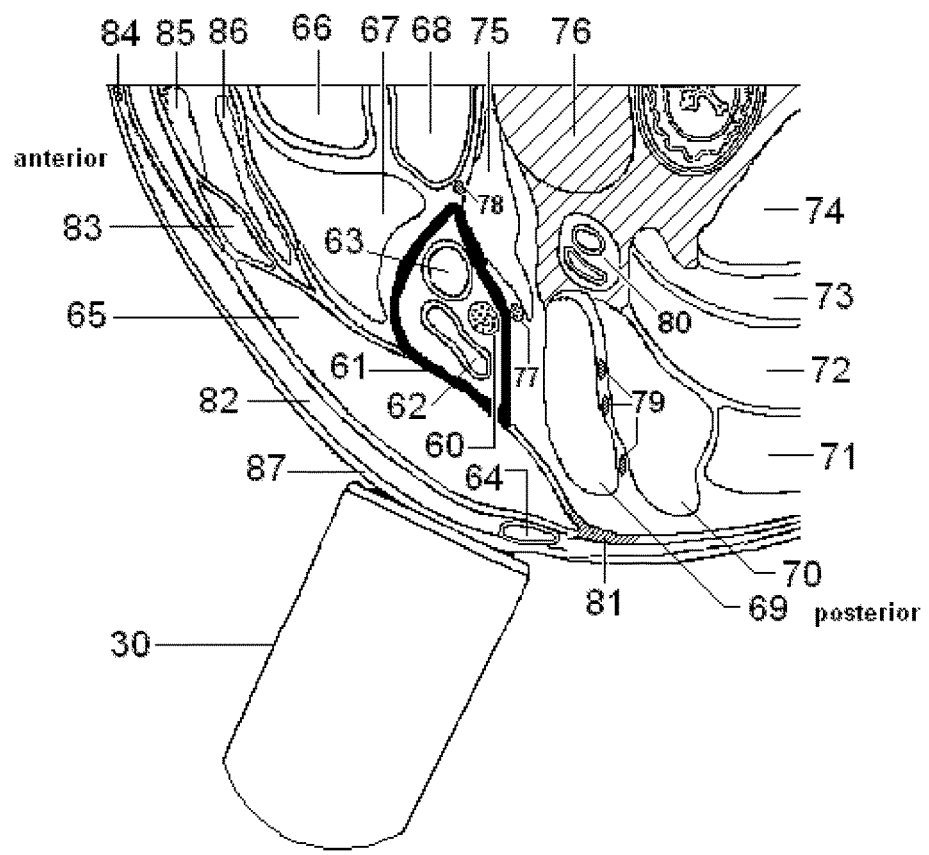
FIG. 10 illustrates the housing of the stimulator according one embodiment of the present invention, when positioned to stimulate a vagus nerve in the patient's neck, wherein the stimulator is applied to the surface of the neck in the vicinity of the identified anatomical structures.

FIGS. 9 and 10 illustrate some of the major structures of the neck, in order to point out structures that could potentially be stimulated electrically, when the stimulator is positioned as in FIGS. 7 and 8. For comparison with FIG. 7, FIG. 9A illustrates the approximate locations of the cervical vertebrae C1 through C7. The thyroid cartilage, the largest of the cartilages that make up the cartilage structure in and around the trachea that contains the larynx, lies at the vertebral levels of C4 and C5. The laryngeal prominence 111 (Adam's apple) in the middle of the neck is formed by the thyroid cartilage at approximately vertebral level C4.

As shown in FIG. 9A, the common carotid artery 100 extends from the base of the skull 102 through the neck 104 to the first rib and sternum (not shown). Carotid artery 100 includes an external carotid artery 106 and an internal carotid artery 108 and is protected by fibrous connective tissue, namely, the carotid sheath. The three major structures within the carotid sheath are the common carotid artery 100, the internal jugular vein 110 and the vagus nerve (not shown).

Proceeding from the skin and fat of the neck to the carotid sheath, the shortest line from the stimulator 30 to the vagus nerve may pass successively through the platysma muscle 82, the sternocleidomastoid muscle 65, and the carotid sheath (see FIGS. 9B and 9C). The anatomy along this line is shown in more detail in FIG. 10, which is a cross-section of half of the neck at vertebra level C6. The vagus nerve 60 is identified in FIG. 10, along with the carotid sheath 61 that is identified there in bold peripheral outline. The carotid sheath encloses not only the vagus nerve, but also the internal jugular vein 62 and the common carotid artery 63. Structures that may be identified near the surface of the neck include the external jugular vein 64 and the sternocleidomastoid muscle 65, which protrudes when the patient turns his or her head. Additional organs in the vicinity of the vagus nerve include the trachea 66, thyroid gland 67, esophagus 68, scalenus anterior muscle 69, scalenus medius muscle 70, levator scapulae muscle 71, splenius colli muscle 72, semispinalis capitis muscle 73, semispinalis colli muscle 74, longus colli muscle and longus capitis muscle 75. The sixth cervical vertebra 76 is shown with bony structure indicated by hatching marks. Additional structures shown in the figure are the phrenic nerve 77, sympathetic ganglion 78, brachial plexus 79, vertebral artery and vein 80, prevertebral fascia 81, platysma muscle 82, omohyoid muscle 83, anterior jugular vein 84, sternohyoid muscle 85, sternothyroid muscle 86, and skin with associated fat 87.

The skin 87 at this location has innervation that is associated with particular dermatomes, although the dermatome extent varies from individual to individual [LADAK A, Tubbs R S, Spinner R J. Mapping sensory nerve communications between peripheral nerve territories. Clin Anat. 2013 Jul. 3. doi: 10.1002/ca.22285, pp. 1-10; C. E. POLETTI. C2 and C3 pain dermatomes in man. Cephalalgia 11(3,1991):155-159]. Men and women also have a different skin anatomy there because the skin of men may contain a significantly greater number of hair follicles.

It is also understood that there may be significant individual variation in internal neck anatomy, and this should be taken into account when positioning the stimulator 30 [commonly assigned and co-pending patent application entitled IMPLANTATION OF WIRELESS VAGUS NERVE STIMULATORS, to SIMON et al., which is hereby incorporated by reference]. In addition, for patients having necks that are unusually wrinkled or that contain large amounts of fatty tissue, the skin may have to be first taped or otherwise made to conform to a flattened or smooth configuration in order for the methods of the invention to be applied successfully.

Once the stimulator has been preliminarily positioned, testing may be performed in order to ascertain that the position is correct. After testing, the correct position may be marked on the patient's skin, for example with fluorescent dyes that are excited with infrared or ultraviolet light, to facilitate subsequent placement of the stimulator [commonly assigned and co-pending patent application U.S. Ser. No. 13/872,116, entitled DEVICES AND METHODS FOR MONITORING NON-INVASIVE VAGUS NERVE STIMULATION, to SIMON et al., which is hereby incorporated by reference].

In certain aspects of the invention, the measurement of an evoked potential may be used to optimize non-invasive stimulation of the vagus nerve with, for example, one of the devices described here. Given that a particular evoked potential can be quantified that represents stimulation of the vagus nerve, the operator can use this measurement to confirm that the action potentials have been created in the vagus nerve during electrical stimulation. In this manner, the operator may, for example, vary a characteristic of the electrical impulses generator by the vagus nerve stimulator in order to ensure that such stimulation is effectively stimulating the vagus nerve at a therapeutic level. For example, if such stimulation does not initially generate the evoked potentials that would confirm the firing of the action potentials in the vagus nerve, the operator may vary aspects of the signal, such as the amplitude, frequency, pulse width and/or duty cycle until such an evoked potential is generated. In addition or alternatively, the operator may vary the placement or orientation of the device on the subject's neck to ensure proper stimulation of the vagus nerve. As another alternative, the operator may position the vagal nerve stimulator on the other side of the patient's neck (left to right or vice versa) in an attempt to optimize the stimulation.

Use of Feedback and Automatic Control Theory Methods to Treat Patients

When vagus nerve stimulation is being performed, the disclosed system generally also uses feedback methods, as defined in the engineering control theory of automatic control. For example, irrespective of the use of biofeedback, feedback may be used in an attempt to compensate for motion of the stimulator relative to the vagus nerve and to avoid potentially dangerous situations, such as excessive heart rate. It may also be used in a form of automatic gain control, in which the parameters of the vagus nerve stimulation are varied automatically until a responsive property, such as a characteristic of the evoked potential, lies within a preferred range.

Generally, the devices shown in FIG. 1B will be used to directly stimulate the vagus nerve, in addition to, or instead of, stimulating sensory nerves within the skin. As described herein and in co-pending, commonly assigned patent application U.S. Ser. No. 13/222,087, entitled Devices and methods for non-invasive capacitive electrical stimulation and their use for vagus nerve stimulation on the neck of a patient, to SIMON et al. (which is hereby incorporated by reference), Applicant has developed a stimulator device that can noninvasively stimulate a vagus nerve directly in the patient's neck, without producing cutaneous discomfort to a patient. When the vagus nerve is being stimulated by the device, the quality of sensation in the patient's skin above the vagus nerve depends strongly on the stimulation current and frequency, such that when the currents are not much greater than the perception threshold, the cutaneous sensations may be described as tingle, itch, vibration, buzz, touch, pressure, or pinch. For situations in which the skin is being stimulated with a constant current and with a particular type of stimulation waveform that is described below, any such cutaneous sensation may be ignored by the patient, and the stimulator does not serve as an exteroceptive biofeedback device. In that case, the device resembles instead a physiological control device that may be used to stimulate structures of the central nervous system and/or "Other physiological systems", via stimulation of the vagus nerve, as indicated in FIG. 1B. The particular structures of the central nervous system or other physiological systems that are affected by the vagus nerve stimulation depend on the parameters of the vagus nerve stimulation, which are selected to stimulate the particular system. Direct electrical stimulation of the vagus nerve will itself generate evoked potentials, as the resulting vagal action potentials and their sequelae propagate within the central nervous system.

FIG. 1B illustrates a closed-loop (feedback) system for producing (via sensory stimuli) and acquiring (via scalp electrodes) evoked potential data. As an example of such feedback methods, the vagus nerve stimulator may vary a parameter of the nerve stimulus waveform (e.g. amplitude, or frequency in the case of steady-state EP measurement), measure the resulting EP waveform, again vary the parameter based on that waveform measurement, and then repeat this procedure iteratively until it results in an EP waveform that exhibits preferred features that lie within some specified range. As now described, with control theory methods, the parameters of the vagus nerve stimulation may be changed automatically, depending on the values on physiological measurements that are made (or on values of environmental signals such as ambient light and sound), in attempt to maintain the values of the physiological signals within predetermined ranges.

When stimulating the vagus nerve noninvasively, motion artifact variability may often be attributable to the patient's breathing, which involves contraction and associated change in geometry of the sternocleidomastoid muscle that is situated close to the vagus nerve (identified as 65 in FIGS. 9C and 10). Modulation of the stimulator amplitude to compensate for this variability may be accomplished by measuring the patient's respiratory phase, or more directly by measuring movement of the stimulator, then using controllers (e.g., PID controllers) that are known in the art of control theory, as now described.

As shown in FIG. 1B, the central nervous system and physiological systems receive input via a vagus nerve from the vagus nerve stimulation device, including the device's controlling electronic components that may be used to select or set parameters for the stimulation protocol (amplitude, frequency, pulse width, burst number, etc.) or alert the patient as to the need to use or adjust the stimulator (i.e., an alarm). For example, the controller may comprise the control unit 330 in FIG. 2. Feedback to the controller in the schema shown in FIG. 1B is possible because physiological measurements are made using sensors.

The physiological sensors used in the invention will ordinarily include more sensors than those needed simply to construct a biofeedback signal for a particular clinical application. This is because the extra sensors may be needed for purposes such as compensating for motion artifacts, or they may be needed in order to properly model the time-course of the physiological signal that is to be controlled, as described below.

The preferred sensors will include ones ordinarily used for ambulatory monitoring. For example, the sensors may comprise those used in conventional Holter and bedside monitoring applications, for monitoring heart rate and variability, ECG, respiration depth and rate, core temperature, hydration, blood pressure, brain function, oxygenation, skin impedance, and skin temperature. The sensors may be embedded in garments or placed in sports wristwatches, as currently used in programs that monitor the physiological status of soldiers [G. A. SHAW, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141]. The ECG sensors should be adapted to the automatic extraction and analysis of particular features of the ECG, for example, indices of P-wave morphology, as well as heart rate variability indices of parasympathetic and sympathetic tone. Measurement of respiration using noninvasive inductive plethysmography, mercury in silastic strain gauges or impedance pneumography is particularly advised, in order to account for the effects of respiration on the heart. A noninvasive accelerometer may also be included among the ambulatory sensors, in order to identify motion artifacts. An event marker may also be included in order for the patient to mark relevant circumstances and sensations.

For brain monitoring, the sensors may comprise ambulatory EEG sensors that may also be used for measurement of evoked potentials [CASSON A, Yates D, Smith S, Duncan J, Rodriguez-Villegas E. Wearable electroencephalography. What is it, why is it needed, and what does it entail? IEEE Eng Med Biol Mag. 29(3,2010):44-56] or optical topography systems for mapping prefrontal cortex activation [ATSUMORI H, Kiguchi M, Obata A, Sato H, Katura T, Funane T, Maki A. Development of wearable optical topography system for mapping the prefrontal cortex activation. Rev Sci Instrum. 2009 April; 80(4):043704, pp. 1-6]. Signal processing methods, comprising not only the application of conventional linear filters to the raw EEG data, but also the nearly real-time extraction of non-linear signal features from the data, may be considered to be a part of the EEG monitoring [D. Puthankattil SUBHA, Paul K. Joseph, Rajendra Acharya U, and Choo Min Lim. EEG signal analysis: A survey. J Med Syst 34(2010):195-212]. Such features would include EEG bands (e.g., delta, theta, alpha, beta).

Detection of the phase of respiration may be performed non-invasively by adhering a thermistor or thermocouple probe to the patient's cheek so as to position the probe at the nasal orifice. Strain gauge signals from belts strapped around the chest, as well as inductive plethysmography and impedance pneumography, are also used traditionally to generate a signal non-invasively that rises and falls as a function of the phase of respiration. Respiratory phase may also be inferred from movement of the sternocleidomastoid muscle that also causes movement of the vagus nerve stimulator during breathing, measured using accelerometers attached to the vagus nerve stimulator, as described below. After digitizing such signals, the phase of respiration may be determined using software such as "puka", which is part of PhysioToolkit, a large published library of open source software and user manuals that are used to process and display a wide range of physiological signals [GOLDBERGER A L, Amaral LAN, Glass L, Hausdorff J M, Ivanov P Ch, Mark R G, Mietus J E, Moody G B, Peng C K, Stanley H E. PhysioBank, PhysioToolkit, and PhysioNet: Components of a New Research Resource for Complex Physiologic Signals. Circulation 101(23,2000):e215-e220] available from PhysioNet, M.I.T. Room E25-505A, 77 Massachusetts Avenue, Cambridge, Mass. 02139]. In one embodiment of the present invention, the control unit 330 in FIG. 2 contains an analog-to-digital converter to receive such analog respiratory signals, and software for the analysis of the digitized respiratory waveform resides within the control unit 330. That software extracts turning points within the respiratory waveform, such as end-expiration and end-inspiration, and forecasts future turning-points, based upon the frequency with which waveforms from previous breaths match a partial waveform for the current breath. The control unit 330 then controls the impulse generator 310 in FIG. 2, for example, to stimulate the selected nerve only during a selected phase of respiration, such as all of inspiration or only the first second of inspiration, or only the expected middle half of inspiration. In other embodiments of the invention, the physiological or environmental signals are transmitted wirelessly to the controller, as shown in FIG. 6. Some such signals may be received by the docking station (e.g., ambient sound signals) and other may be received within the stimulator housing (e.g., motion signals).

It may be therapeutically advantageous to program the control unit 330 in FIG. 2 to control the impulse generator 310 in such a way as to temporally modulate stimulation by the electrodes, depending on the phase of the patient's respiration. In patent application JP2008/081479A, entitled Vagus nerve stimulation system, to YOSHIHOTO, a system is also described for keeping the heart rate within safe limits. When the heart rate is too high, that system stimulates a patient's vagus nerve, and when the heart rate is too low, that system tries to achieve stabilization of the heart rate by stimulating the heart itself, rather than use different parameters to stimulate the vagus nerve. In that disclosure, vagal stimulation uses an electrode, which is described as either a surface electrode applied to the body surface or an electrode introduced to the vicinity of the vagus nerve via a hypodermic needle. That disclosure is unrelated to the biofeedback problems that are addressed here, but it does consider stimulation during particular phases of the respiratory cycle, for the following reason. Because the vagus nerve is near the phrenic nerve (77 in FIG. 10), Yoshihoto indicates that the phrenic nerve will sometimes be electrically stimulated along with the vagus nerve. The present applicants have not experienced this problem, so the problem may be one of a misplaced electrode. In any case, the phrenic nerve controls muscular movement of the diaphragm, so consequently, stimulation of the phrenic nerve causes the patient to hiccup or experience irregular movement of the diaphragm, or otherwise experience discomfort. To minimize the effects of irregular diaphragm movement, Yoshihoto's system is designed to stimulate the phrenic nerve (and possibly co-stimulate the vagus nerve) only during the inspiration phase of the respiratory cycle and not during expiration. Furthermore, the system is designed to gradually increase and then decrease the magnitude of the electrical stimulation during inspiration (notably amplitude and stimulus rate) so as to make stimulation of the phrenic nerve and diaphragm gradual.

Furthermore, as an option in the present invention, parameters of the stimulation may be modulated by the control unit 330 to control the impulse generator 310 in such a way as to temporally modulate stimulation by the electrodes, so as to achieve and maintain the heart rate within safe or desired limits. In that case, the parameters of the stimulation are individually raised or lowered in increments (power, frequency, etc.), and the effect as an increased, unchanged, or decreased heart rate is stored in the memory of the control unit 330. When the heart rate changes to a value outside the specified range, the control unit 330 automatically resets the parameters to values that had been recorded to produce a heart rate within that range, or if no heart rate within that range has yet been achieved, it increases or decreases parameter values in the direction that previously acquired data indicate would change the heart rate in the direction towards a heart rate in the desired range. Similarly, the arterial blood pressure is also recorded non-invasively in an embodiment of the invention (e.g., with a wrist tonometer), and the control unit 330 extracts the systolic, diastolic, and mean arterial blood pressure from the blood pressure waveform. The control unit 330 will then control the impulse generator 310 in such a way as to temporally modulate nerve stimulation by the electrodes, in such a way as to achieve and maintain the blood pressure within predetermined safe or desired limits, by the same method that was indicated above for the heart rate.

Let the measured output variables from physiological sensors of the system in FIG. 1B be denoted by $y_i$ (i=1 to Q); let the desired (reference or setpoint) values of $y_i$ be denoted by $r_i$ and let the controller's output via the stimulator consist of variables $u_j$ (j=1 to P), which are also the input to the vagus nerve and other biological entities. The objective is for a controller to select the output from the stimulator, i.e. input to the body, ($u_j$) in such a way that the physiological signal output variables (or a subset of them) closely follows the reference signals $r_i$. Thus, it is intended that the control error $e_i=r_i-y_i$ be small, even if there is environmental input or noise to the system. In what follows, consider the error function $e_i=r_i-y_i$ to be the sensed physiological input to the control unit 330 in FIG. 2 (i.e., the reference signals are integral to the controller, which subtracts the measured system values from them to construct the control error signal). The controller will also receive a set of measured environmental signals $v_k$ (k=1 to R), which also act upon the system as shown in FIG. 1B. The patient's response to biofeedback may be considered to be a type of environmental input. During the initial, preliminary measurements, biofeedback is not performed, but it may also be included during subsequent attempts to tune and model the entire system.

As a first example of the use of feedback to control the system, consider the problem of adjusting the input u(t) to the body (i.e., output from the controller as applied to the body via the impulse generator) in order to compensate for motion artifacts. Nerve activation is generally a function of the second spatial derivative of the extracellular potential along the nerve's axon, which would be changing as the position of the stimulator varies relative to the axon [F. RATTAY. The basic mechanism for the electrical stimulation of the nervous system. Neuroscience 89 (2, 1999):335-346]. Such motion artifact can be due to movement by the patient (e.g., neck movement) or movement within the patient (e.g. sternocleidomastoid muscle contraction associated with respiration), or it can be due to movement of the stimulator relative to the body (slippage or drift). Thus, one expects that because of such undesired or unavoidable motion, there will usually be some error (e=r−y) in the intended (r) versus actual (y) sensor values that needs continuous adjustment.

Accelerometers can be used to detect all these types of movement, using for example, Model LSM330DL from STMicroelectronics, 750 Canyon Dr #300 Coppell, Tex. 75019. In one embodiment, one or more accelerometer is attached to the patient's neck, and one or more accelerometer is attached to the head(s) of the stimulator in the vicinity of where the stimulator contacts the patient. Because the temporally integrated outputs of the accelerometers provide a measurement of the current position of each accelerometer, the combined accelerometer outputs make it possible to measure any movement of the stimulator relative to the underlying tissue.

The location of the vagus nerve underlying the stimulator may be determined preliminarily by placing an ultrasound probe at the location where the center of the stimulator will be placed [KNAPPERTZ V A, Tegeler C H, Hardin S J, McKinney W M. Vagus nerve imaging with ultrasound: anatomic and in vivo validation. Otolaryngol Head Neck Surg 118(1,1998):82-5]. The ultrasound probe is configured to have the same shape as the stimulator, including the attachment of one or more accelerometer. As part of the preliminary protocol, the patient with accelerometers attached is then instructed or helped to perform neck movements, breathe deeply so as to contract the sternocleidomastoid muscle, and generally simulate possible motion that may accompany prolonged stimulation with the stimulator. This would include possible slippage or movement of the stimulator relative to an initial position on the patient's neck. While these movements are being performed, the accelerometers are acquiring position information, and the corresponding location of the vagus nerve is determined from the ultrasound image. With these preliminary data, it is then possible to infer the location of the vagus nerve relative to the stimulator, given only the accelerometer data during a stimulation session, by interpolating between the previously acquired vagus nerve positional data as a function of accelerometer position data.

For any given position of the stimulator relative to the vagus nerve, it is also possible to infer the amplitude of the electric field that it produces in the vicinity of the vagus nerve. This is done by calculation or by measuring the electric field that is produced by the stimulator as a function of depth and position within a phantom that simulates the relevant bodily tissue [Francis Marion MOORE. Electrical Stimulation for pain suppression: mathematical and physical models. Thesis, School of Engineering, Cornell University, 2007; Bartosz SAWICKI, Robert Szmurlo, Przemyslaw Plonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Thus, in order to compensate for movement, the controller may increase or decrease the amplitude of the output from the stimulator (u) in proportion to the inferred deviation of the amplitude of the electric field in the vicinity of the vagus nerve, relative to its desired value.

A state-space representation, or model, of the entire system consists of a set of first order differential equations of the form $dy_i/dt = F_i(t, \{y_i\}, \{u_j\}, \{v_k\}; \{r_j\})$, where t is time and where in general, the rate of change of each variable $y_i$ is a function ($F_i$) of many other output variables as well as the input and environmental signals. Classical control theory is concerned with situations in which the functional form of $F_i$ is as a linear combination of the state (y) and bodily input (u and v) variables, but in which coefficients of the linear terms are not necessarily known in advance. In this linear case, the differential equations may be solved with linear transform (e.g., Laplace transform) methods, which convert the differential equations into algebraic equations for straightforward solution. Thus, for example, a single-input single-output system (dropping the subscripts on variables) may have input from a controller of the form: $u(t)=K_p e(t) + K_i \int_0^t e(\tau)d\tau + K_d dr/de$ where the parameters for the controller are the proportional gain ($K_p$), the integral gain ($K_i$) and the derivative gain ($K_d$). This type of controller, which forms a controlling input signal with feedback using the error e=r−y, is known as a PID controller (proportional-integral-derivative). Commercial versions of PID controllers are available, and they are used in 90% of all control applications.

Optimal selection of the parameters of the controller could be through calculation, if the coefficients of the corresponding state differential equation were known in advance. However, they are ordinarily not known, so selection of the controller parameters (tuning) is accomplished by experiments in which the error e either is or is not used to form the system input (respectively, closed loop or open loop experiments). In an open loop experiment, the input is increased in a step (or random binary sequence of steps), and the system response is measured. In a closed loop experiment, the integral and derivative gains are set to zero, the proportional gain is increased until the system starts to oscillate, and the period of oscillation is measured. Depending on whether the experiment is open or closed loop, the selection of PID parameter values may then be selected according to rules that were described initially by Ziegler and Nichols. There are also many improved versions of tuning rules, including some that can be implemented automatically by the controller [LI, Y., Ang, K. H. and Chong, G. C. Y. Patents, software and hardware for PID control: an overview and analysis of the current art. IEEE Control Systems Magazine, 26 (1,2006): 42-54; Karl Johan Åström & Richard M. Murray. Feedback Systems: An Introduction for Scientists and Engineers. Princeton N.J.: Princeton University Press, 2008; Finn HAUGEN. Tuning of PID controllers (Chapter 10) In: Basic Dynamics and Control. 2009. ISBN 978-82-91748-13-9. TechTeach, Enggravhøgda 45, N-3711 Skien, Norway. http://techteach.no., pp. 129-155; Dingyu XUE, YangQuan Chen, Derek P. Atherton. PID controller design (Chapter 6), In: Linear Feedback Control: Analysis and Design with MATLAB. Society for Industrial and Applied Mathematics (SIAM). 3600 Market Street, 6th Floor, Philadelphia, Pa. (2007), pp. 183-235; Jan JANTZEN, Tuning Of Fuzzy PID Controllers, Technical University of Denmark, report 98-H 871, Sep. 30, 1998].

Although classical control theory works well for linear systems having one or only a few system variables, special methods have been developed for systems in which the system is nonlinear (i.e., the state-space representation contains nonlinear differential equations), or multiple input/output variables. Such methods are important for the present invention because the physiological system to be controlled will be generally nonlinear, and there will generally be multiple output physiological signals. It is understood that those methods may also be implemented in the control unit 330 shown in FIG. 2 [Torkel GLAD and Lennart Ljung. Control Theory. Multivariable and Nonlinear Methods. New York: Taylor and Francis, 2000; Zdzislaw BUBNICKI. Modern Control Theory. Berlin: Springer, 2005].

The control unit 330 shown in FIG. 2 may also make use of feed-forward methods [Coleman BROSILOW, Babu Joseph. Feedforward Control (Chapter 9) In: Techniques of Model-Based Control. Upper Saddle River, N.J.: Prentice Hall PTR, 2002. pp, 221-240]. Thus, the controller in FIG. 2 may be a type of predictive controller, methods for which have been developed in other contexts as well, such as when a model of the system is used to calculate future outputs of the system, with the objective of choosing among possible inputs so as to optimize a criterion that is based on future values of the system's output variables.

A mathematical model of the system is needed in order to perform the predictions of system behavior, for purposes of including the predictions in a feedforward control device. If the mechanisms of the systems are not sufficiently understood in order to construct a physiologically-based model, a black-box model may be used instead. Such models comprise autoregressive models [Tim BOLLERSLEV. Generalized autoregressive conditional heteroskedasticity. Journal of Econometrics 31(1986):307-327], or those that make use of principal components [James H. STOCK, Mark W. Watson. Forecasting with Many Predictors, In: Handbook of Economic Forecasting. Volume 1, G. Elliott, C. W. J. Granger and A. Timmermann, eds (2006) Amsterdam: Elsevier B. V, pp 515-554], Kalman filters [Eric A. WAN and Rudolph van der Merwe. The unscented Kalman filter for nonlinear estimation, In: Proceedings of Symposium 2000 on Adaptive Systems for Signal Processing, Communication and Control (AS-SPCC), IEEE, Lake Louise, Alberta, Canada, October, 2000, pp 153-158], wavelet transforms [O. RENAUD, J.-L. Stark, F. Murtagh. Wavelet-based forecasting of short and long memory time series. Signal Processing 48(1996):51-65], hidden Markov models [Sam ROWEIS and Zoubin Ghahramani. A Unifying Review of Linear Gaussian Models. Neural Computation 11(2,1999): 305-345], or artificial neural networks [Guoqiang ZHANG, B. Eddy Patuwo, Michael Y. Hu. Forecasting with artificial neural networks: the state of the art. International Journal of Forecasting 14(1998): 35-62].

For the present invention, the preferred black box model will be one that makes use of support vector machines. A support vector machine (SVM) is an algorithmic approach to the problem of classification within the larger context of supervised learning. A number of classification problems whose solutions in the past have been solved by multi-layer back-propagation neural networks, or more complicated methods, have been found to be more easily solvable by SVMs. In the present context, a training set of physiological data will have been acquired that includes whether or not a physiological variable is outside of its desired range. Ordinarily, the variable will be one that is associated with the patient's condition (e.g., blood pressure for a hypertensive individual, or when biofeedback is being performed it may be the physiological signal used to construct the biofeedback signal).

Thus, the classification of the patient's state is whether or not the variable is out of range, and the data used to make the classification consist of the remaining acquired physiological data, evaluated at A time units prior to the time at which a forecast of the patient's status is to be made. Accordingly, the SVM is trained to forecast Δ time units into the future, where the time of the future forecast Δ is selected by the user. The forecast consists of whether the variable is out of range, and optionally the predicted values of any or all of the physiological variables that are being sensed. After training the SVM, it is implemented as part of the controller. If Δ=0 and the signal being forecast is the one use to construct a biofeedback signal, then the signal is simply the ordinary biofeedback signal. However, when Δ>0, the signal presented exteroceptively to the patient can correspond to a predicted, future value of the physiological variable. In that case, the system is effectively used for biofeedforward control, rather than for biofeedback control. Then, the patient can learn to respond consciously to what the signal is predicted to become, rather than to what it currently is. Just as an anticipatory response is useful for muscular systems such as when attempting to grasp a moving rather than stationary object, then so too, the biofeedforward control is useful for control of the autonomic nervous system when it is experiencing significant time-varying fluctuations [Christopher J. C. BURGES. A tutorial on support vector machines for pattern recognition. Data Mining and Knowledge Discovery 2(1998), 121-167; J. A. K. Suykens, J. Vandewalle, B. De Moor. Optimal Control by Least Squares Support Vector Machines. Neural Networks 14 (2001):23-35; Sapankevych, N. and Sankar, R. Time Series Prediction Using Support Vector Machines: A Survey. IEEE Computational Intelligence Magazine 4(2,2009): 24-38; Press, W H; Teukolsky, S A; Vetterling, W T; Flannery, B P (2007). Section 16.5. Support Vector Machines. In: Numerical Recipes: The Art of Scientific Computing (3rd ed.). New York: Cambridge University Press].

A disclosure of the use of such feedback and feedforward methods to forecast and avert the onset of many types of medical crises was made in the co-pending, commonly assigned patent application U.S. Ser. No. 13/655,716 (publication US20130066395), entitled Nerve stimulation methods for averting imminent onset or episode of a disease, to SIMON et al, which is hereby incorporated by reference. The medical crises comprise attacks of migraine headache, as well as an asthma attack, epileptic seizure, transient ischemic attack or stroke, onset of atrial fibrillation, myocardial infarction, onset of ventricular fibrillation or tachycardia, panic attack, and attacks of acute depression. The present invention extends that disclosure to allow the additional use of biofeedback, as shown in FIG. 1B.

An application of that previous disclosure, in the context of the present invention, is as follows. When the physiological system has been mathematically modeled first without the use of biofeedback, the model provides an estimate of the temporal behavior of the system when it is free from conscious control by the individual whose physiological properties are being measured. When biofeedback is subsequently incorporated into the methods as shown in FIG. 1B, then to the extent that the forecasted behavior of the physiological system deviates from what the model predicts, that quantitative deviation may be attributed in part to how the individual is consciously trying to modulate the physiological system. In the previous discussion surrounding FIG. 1B, it was described how vagus nerve stimulation can be used to amplify or enhance the conscious control of the system, by first allowing the individual to attempt biofeedback by itself, then using the device to sense the direction that the individual is trying to move the physiological variable and amplify that effect by stimulating the vagus nerve to move the variable even more. The mathematical model of the system described above may be used for other situations, in which both biofeedback and automatic control are being performed simultaneously. In those cases, the intentions of the individual may be inferred from the disclosed device as corresponding to the deviation of the physiological variable from what the model predicts, taking into account the standard deviation of the model's forecasting capabilities. The stimulator may then be programmed to stimulate the vagus nerve in such a way as to amplify or enhance the inferred intentions of the individual, when biofeedback and automatic control are used simultaneously.

Selection of the Electrical Stimulation Waveform

In the present invention, electrical stimulation of the vagus nerve and/or the skin results secondarily in the stimulation of regions of the brain that are involved in sensory processing, autonomic regulation and conscious action. Selection of stimulation waveform parameters to preferentially modulate particular regions of the brain may be done empirically, wherein a set of electrical stimulation waveform parameters is chosen (amplitude, frequency, pulse width, etc.), and the responsive region of the brain is measured using fMRI or a related imaging method [CHAE J H, Nahas Z, Lomarev M, Denslow S, Lorberbaum J P, Bohning D E, George M S. A review of functional neuroimaging studies of vagus nerve stimulation (VNS). J Psychiatr Res. 37(6,2003):443-455; CONWAY C R, Sheline Y I, Chibnall J T, George M S, Fletcher J W, Mintun M A. Cerebral blood flow changes during vagus nerve stimulation for depression. Psychiatry Res. 146(2,2006):179-84]. Thus, by performing the imaging with different sets of stimulation parameters, a database may be constructed, such that the inverse problem of selecting parameters to match a particular selected brain region may be solved by consulting the database.

However, there may be significant variation between individuals in regards to the correspondence between stimulation parameters and the associated brain structures that are activated. Furthermore, it may be impractical to perform fMRI imaging on each individual who is to be trained or treated by the disclosed invention. The individualized selection of parameters for the nerve stimulation protocol will in any case involve some trial and error, in order to obtain a beneficial response without the sensation of skin pain or muscle twitches. The parameters may also have to be updated periodically to compensate for any adaptation on the part of the patient's nervous system to the electrical stimulation. In addition, the selection of parameter values may involve tuning and modeling as understood in control theory, as described in the previous section. It is also understood that to some extent, parameters may also be varied randomly in order to simulate normal physiological variability, thereby possibly inducing a beneficial response in the patient [BUCHMAN T G. Nonlinear dynamics, complex systems, and the pathobiology of critical illness. Curr Opin Crit Care 10(5,2004):378-82].

With regard to stimulating the patient's skin to construct a biofeedback signal, many stimulation waveforms that have been tried in connection with electro-tactile communication devices may also be used for the present invention [R. H. GIBSON. Electrical stimulation of pain and touch. pp. 223-261. In: D. R. Kenshalo, ed. The Skin Senses. Springfield, Ill.: Charles C Thomas, 1968; Erich A. PFEIFFER. Electrical stimulation of sensory nerves with skin electrodes for research, diagnosis, communication and behavioral conditioning: A survey. Medical and Biological Engineering. 6(6,1968):637-651; Kahori KITA, Kotaro Takeda, Rieko Osu, Sachiko Sakata, Yohei Otaka, Junichi Ushiba. A Sensory feedback system utilizing cutaneous electrical stimulation for stroke patients with sensory loss. Proc. 2011 IEEE International Conference on Rehabilitation Robotics, Zurich, Switzerland, Jun. 29-Jul. 1, 2011, 2011:5975489, pp 1-6; Mark R. PRAUSNITZ. The effects of electric current applied to skin: A review for transdermal drug delivery. Advanced Drug Delivery Reviews 18 (1996) 395-425].

For example, let stimL be the lower threshold of the skin stimulation current, defined for each patient as the lowest current at which he or she can feel stimulation to the skin. Let stimU be the upper threshold of the skin stimulation current, defined as a fixed percentage (e.g. 95%) of the magnitude of current to the skin that first begins to materially stimulate the vagus nerve, as evidenced by any of the methods described in commonly assigned and co-pending patent application U.S. Ser. No. 13/872,116, entitled DEVICES AND METHODS FOR MONITORING NON-INVASIVE VAGUS NERVE STIMULATION, to SIMON et al., which is hereby incorporated by reference. StimU may be measured when the waveform used to stimulate the vagus nerve itself is simultaneously applied as a superimposed signal (see below), but in which the vagus stimulation waveform has an amplitude that is also set just under the one at which the vagus nerve is first materially stimulated.

Let ipL and ipU be the minimum and maximum values of the sensed physiological variable that are to be used for biofeedback, respectively. Each of these factors (stimL, stimU, ipL and ipU) is measured or decided shortly prior to the therapy. Let stim(n) be defined as a magnification factor of the current at the n-th sampling of the physiological signal that is used to construct the biofeedback signal, which then has the value ip(n). Then, let stim(n)=stimL when ip(n)<ipL; let stim(n)=stimU when ip(n)>ipU, and let stim(n) vary linearly between stimL and stimU as a function of ip(n), when ip(n) is between or at the endpoints ipL and ipU.

In this embodiment, the electrical biofeedback signal to the skin will be proportional to stim(n) multiplied by f(t), where f(t) is a monophasic rectangular electric pulse sequence having a repeat interval of, for example, 10 milliseconds and duration of 300 microseconds. The interval and pulse duration may be optimized for each patient, so that the psychological sensation of the cutaneous biofeedback is maximized for a given total skin current, but without any sensation of pain or discomfort.

A digital biofeedback signal to the skin may also be used. For example, ipL, ipU, and ipL+(ipU−ipL)/2 may be used as the only three levels that are applied to the skin, and each of them may have a pulse train duration of, e.g., 0.5, 1, or 2 seconds, for a total of 9 possible signal train combinations. The pulse train that is actually applied at any instant may then be selected according to the measured physiological signal, with higher amplitude and longer pulse trains corresponding to increasing values of the physiological signal.

Figure 11A:
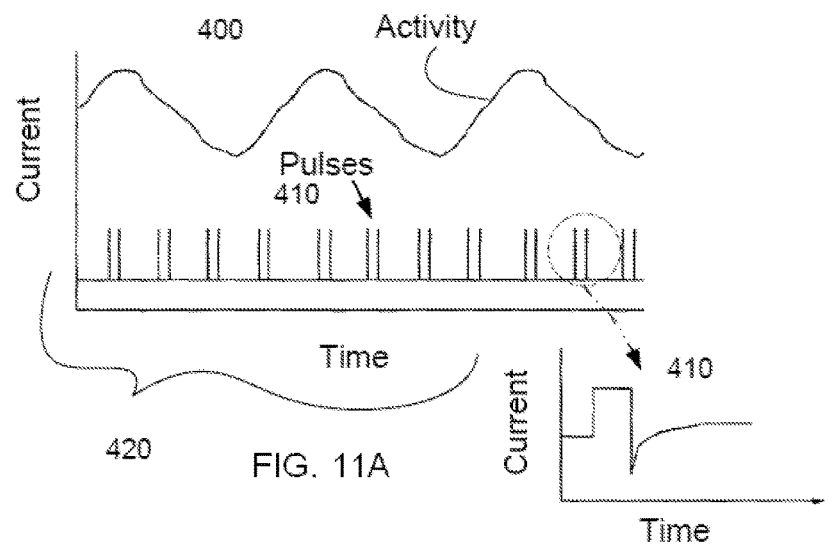
FIGS. 11A-11C show exemplary electrical voltage/current profiles and waveforms for stimulating and/or modulating impulses that are applied to a nerve, including a representation of the relation between stimulation pulses and physiological activity (FIG. 11A), and the shape of the an exemplary applied waveform on a short (FIG. 11B) and longer (FIG. 11C) time scale.

The selection of a waveform to stimulate a nerve that lies deep under the skin, such as a vagus nerve, is a more difficult problem because the selection must be made so as not to cause skin pain or muscle twitches. The waveform for stimulating the deep nerve will generally be superimposed upon the cutaneous biofeedback signal described above. FIG. 11A illustrates an exemplary electrical voltage/current profile for a stimulating, blocking and/or modulating impulse applied to a portion or portions of selected nerve (e.g. vagus nerve) in accordance with an embodiment of the present invention. For the preferred embodiment, the voltage and current refer to those that are non-invasively produced within the patient by the electrodes (or stimulator coils). As shown, a suitable electrical voltage/current profile 400 for the blocking and/or modulating impulse 410 to the portion or portions of a nerve may be achieved using pulse generator 310 in FIG. 2. In a preferred embodiment, the pulse generator 310 may be implemented using a power source 320 and a control unit 330 having, for instance, a processor, a clock, a memory, etc., to produce a pulse train 420 to the electrodes 340 that deliver the stimulating, blocking and/or modulating impulse 410 to the nerve. The parameters of the modulation signal 400, such as the frequency, amplitude, duty cycle, pulse width, pulse shape, etc., are preferably programmable. An external communication device may modify the pulse generator programming to facilitate treatment.

A device such as that disclosed in patent publication No. US2005/0216062 may be employed to generate the stimulation waveform. That patent publication discloses a multi-functional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated, as well as the outputs of various sensors which sense prevailing conditions prevailing in this substance, whereby the user of the system can manually adjust the signal, or have it automatically adjusted by feedback, to provide an electrical stimulation signal of whatever type the user wishes, who can then observe the effect of this signal on the entity being treated.

The stimulating and/or modulating impulse signal 410 in FIG. 11A preferably has a frequency, an amplitude, a duty cycle, a pulse width, a pulse shape, etc. selected to influence the therapeutic result, namely, stimulating and/or modulating some or all of the transmissions of the selected nerve. For example, the frequency may be about 1 Hz or greater, such as between about 15 Hz to 100 Hz, more preferably around 25 Hz. The modulation signal may have a pulse width selected to influence the therapeutic result, such as about 1 microseconds to about 1000 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz. The modulation signal may have a peak voltage amplitude selected to influence the therapeutic result, such as about 0.2 volts or greater, such as about 0.2 volts to about 40 volts.

An objective of the disclosed stimulator is to provide both nerve fiber selectivity and spatial selectivity. Spatial selectivity may be achieved in part through the design of the electrode (or magnetic coil) configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for vagus nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting activate indirectly, in an effort to entrain the naturally occurring electrical waveform, as suggested in patent number U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described below, are discovered by trial and error, and then deliberately improved upon.

Invasive nerve stimulation typically uses square wave pulse signals. However, Applicant found that square waveforms are not ideal for non-invasive stimulation of the vagus nerve because they produce excessive pain. Pre-pulses and similar waveform modifications have been suggested as methods to improve selectivity of nerve stimulation waveforms, but Applicant did not find them ideal [Aleksandra VUCKOVIC, Marco Tosato and Johannes J Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51(5,2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Figure 11B:
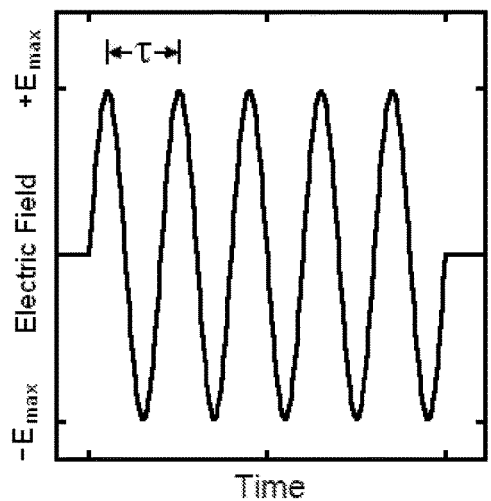
Figure 11C:
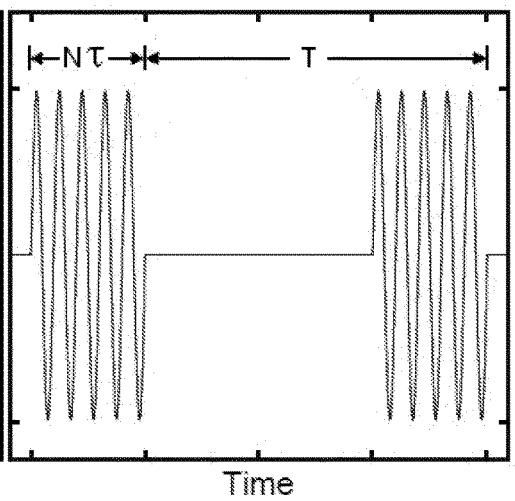

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (⅔, 1991):313-321; U.S. Pat. No. 7,734,340, entitled Stimulation design for neuromodulation, to De Ridder]. However, bursts of sinusoidal pulses were determined to be a preferred stimulation waveform, as shown in FIGS. 11B and 11C. As seen there, individual sinusoidal pulses have a period of tau, and a burst consists of N such pulses. This is followed by a period with no signal (the inter-burst period). The pattern of a burst followed by silent inter-burst period repeats itself with a period of T. For example, the sinusoidal period tau may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 11C to make the bursts discernable). When these exemplary values are used for T and tau, the waveform contains significant Fourier components at higher frequencies (1/200 microseconds=5000/sec), as compared with those contained in transcutaneous nerve stimulation waveforms, as currently practiced.

Applicant is unaware of such a waveform having been used with vagus nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters tau, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10(1989):187-191; Alex R WARD, Nataliya Shkuratova. Russian Electrical Stimulation: The Early Experiments. Physical Therapy 82 (10,2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10,2008):1167-1176; Alex R WARD. Electrical Stimulation Using Kilohertz-Frequency Alternating Current. Physical Therapy 89 (2,2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2,2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 11B and 11C may have an $E_{max}$ value of 17 V/m, which is sufficient to stimulate the nerve but is significantly lower than the threshold needed to stimulate surrounding muscle.

High frequency electrical stimulation is also known in the treatment of back pain at the spine [Patent application US20120197369, entitled Selective high frequency spinal cord modulation for inhibiting pain with reduced side effects and associated systems and methods, to ALATARIS et al.; Adrian A L KAISY, Iris Smet, and Jean-Pierre Van Buyten. Analgeia of axial low back pain with novel spinal neuromodulation. Poster presentation #202 at the 2011 meeting of The American Academy of Pain Medicine, held in National Harbor, Md., Mar. 24-27, 2011].

Those methods involve high-frequency modulation in the range of from about 1.5 KHz to about 50 KHz, which is applied to the patient's spinal cord region. However, such methods are different from the present invention because, for example, they is invasive; they do not involve a bursting waveform, as in the present invention; they necessarily involve A-delta and C nerve fibers and the pain that those fibers produce (see below), whereas the present invention does not; they may involve a conduction block applied at the dorsal root level, whereas the present invention may stimulate action potentials without blocking of such action potentials; and/or they involve an increased ability of high frequency modulation to penetrate through the cerebral spinal fluid, which is not relevant to the present invention. In fact, a likely explanation for the reduced back pain that is produced by their use of frequencies from 10 to 50 KHz is that the applied electrical stimulus at those frequencies causes permanent damage to the pain-causing nerves, whereas the present invention involves only reversible effects [LEE R C, Zhang D, Hannig J. Biophysical injury mechanisms in electrical shock trauma. Annu Rev Biomed Eng 2(2000):477-509].

Consider now which nerve fibers may be stimulated by the non-invasive vagus nerve stimulation waveform shown in FIGS. 11B and 11C. A vagus nerve in man consists of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves, communicating the state of the viscera to the central nervous system.

The largest nerve fibers within a left or right vagus nerve are approximately 20 µm in diameter and are heavily myelinated, whereas only the smallest nerve fibers of less than about 1 µm in diameter are completely unmyelinated. When the distal part of a nerve is electrically stimulated, a compound action potential may be recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 µm diameter), A-beta fibers (afferent or efferent fibers, 5-12 µm), A-gamma fibers (efferent fibers, 3-7 µm), A-delta fibers (afferent fibers, 2-5 µm), B fibers (1-3 µm) and C fibers (unmyelinated, 0.4-1.2 µm). The diameters of group A and group B fibers include the thickness of the myelin sheaths. It is understood that the anatomy of the vagus nerve is developing in newborns and infants, which accounts in part for the maturation of autonomic reflexes. Accordingly, it is also understood that the parameters of vagus nerve stimulation in the present invention are chosen in such a way as to account for this age-related maturation [PEREYRA P M, Zhang W, Schmidt M, Becker LE. Development of myelinated and unmyelinated fibers of human vagus nerve during the first year of life. J Neural Sci 110(1-2, 1992): 107-113].

The waveform disclosed in FIG. 11 contains significant Fourier components at high frequencies (e.g., ½00 microseconds=5000/sec), even if the waveform also has components at lower frequencies (e.g., 25/sec). Transcutaneously, A-beta, A-delta, and C fibers are typically excited at 2000 Hz, 250 Hz, and 5 Hz, respectively, i.e., the 2000 Hz stimulus is described as being specific for measuring the response of A-beta fibers, the 250 Hz for A-delta fibers, and the 5 Hz for type C fibers [George D. BAQUIS et al. TECHNOLOGY REVIEW: THE NEUROMETER CURRENT PERCEPTION THRESHOLD (CPT). Muscle Nerve 22 (Supplement 8,1999): S247-S259]. Therefore, the high frequency component of the noninvasive stimulation waveform will preferentially stimulate the A-alpha and A-beta fibers, and the C fibers will be largely unstimulated.

However, the threshold for activation of fiber types also depends on the amplitude of the stimulation, and for a given stimulation frequency, the threshold increases as the fiber size decreases. The threshold for generating an action potential in nerve fibers that are impaled with electrodes is traditionally described by Lapicque or Weiss equations, which describe how together the width and amplitude of stimulus pulses determine the threshold, along with parameters that characterize the fiber (the chronaxy and rheobase). For nerve fibers that are stimulated by electric fields that are applied externally to the fiber, as is the case here, characterizing the threshold as a function of pulse amplitude and frequency is more complicated, which ordinarily involves the numerical solution of model differential equations or a case-by-case experimental evaluation [David BOINAGROV, Jim Loudin and Daniel Palanker. Strength-Duration Relationship for Extracellular Neural Stimulation: Numerical and Analytical Models. J Neurophysiol 104(2010):2236-2248].

For example, REILLY describes a model (the spatially extended nonlinear nodal model or SENN model) that may be used to calculate minimum stimulus thresholds for nerve fibers having different diameters [J. Patrick REILLY. Electrical models for neural excitation studies. Johns Hopkins APL Technical Digest 9(1, 1988): 44-59]. According to REILLY's analysis, the minimum threshold for excitation of myelinated A fibers is 6.2 V/m for a 20 μm diameter fiber, 12.3 V/m for a 10 μm fiber, and 24.6 V/m for a 5 μm diameter fiber, assuming a pulse width that is within the contemplated range of the present invention (1 ms). It is understood that these thresholds may differ slightly from those produced by the waveform of the present invention as illustrated by REILLY's figures, for example, because the present invention prefers to use sinusoidal rather than square pulses. Thresholds for B and C fibers are respectively 2 to 3 and 10 to 100 times greater than those for A fibers [Mark A. CASTORO, Paul B. Yoo, Juan G. Hincapie, Jason J. Hamann, Stephen B. Ruble, Patrick D. Wolf, Warren M. Grill. Excitation properties of the right cervical vagus nerve in adult dogs. Experimental Neurology 227 (2011): 62-68]. If we assume an average A fiber threshold of 15 V/m, then B fibers would have thresholds of 30 to 45 V/m and C fibers would have thresholds of 150 to 1500 V/m. The present invention produces electric fields at the vagus nerve in the range of about 6 to 100 V/m, which is therefore generally sufficient to excite all myelinated A and B fibers, but not the unmyelinated C fibers. In contrast, invasive vagus nerve stimulators that have been used for the treatment of epilepsy have been reported to excite C fibers in some patients [EVANS M S, Verma-Ahuja S, Naritoku D K, Espinosa J A. Intraoperative human vagus nerve compound action potentials. Acta Neurol Scand 110(2004): 232-238].

It is understood that although devices of the present invention may stimulate A and B nerve fibers, in practice they may also be used so as not to stimulate the A-delta) and B fibers. In particular, if the stimulator amplitude has been increased to the point at which unwanted side effects begin to occur, the operator of the device may simply reduce the amplitude to avoid those effects. For example, vagal efferent fibers responsible for bronchoconstriction have been observed to have conduction velocities in the range of those of B fibers. In those experiments, bronchoconstriction was only produced when B fibers were activated, and became maximal before C fibers had been recruited [R. M. McALLEN and K. M. Spyer. Two types of vagal preganglionic motoneurones projecting to the heart and lungs. J. Physiol. 282(1978): 353-364]. Because proper stimulation with the disclosed devices does not result in the side-effect of bronchoconstriction, evidently the bronchoconstrictive B-fibers are possibly not being activated when the amplitude is properly set. Also, the absence of bradycardia or prolongation of PR interval suggests that cardiac efferent B-fibers are not stimulated. Similarly, A-delta afferents may behave physiologically like C fibers. Because stimulation with the disclosed devices does not produce nociceptive effects that would be produced by jugular A-delta fibers or C fibers, evidently the A-delta fibers may not be stimulated when the amplitude is properly set.

The use of feedback to generate the modulation signal 400 in FIG. 11 may result in a signal that is not periodic, particularly if the feedback is produced from sensors that measure naturally occurring, time-varying aperiodic physiological signals from the patient (see FIG. 1B). In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback were not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128; W Alan C MUTCH, M Ruth Graham, Linda G Girling and John F Brewster. Fractal ventilation enhances respiratory sinus arrhythmia. Respiratory Research 2005, 6:41, pp. 1-9].

So, in one embodiment of the present invention, the modulation signal 400 in FIG. 11, with or without feedback, will stimulate the selected nerve fibers in such a way that one or more of the stimulation parameters (power, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

Figure 12:
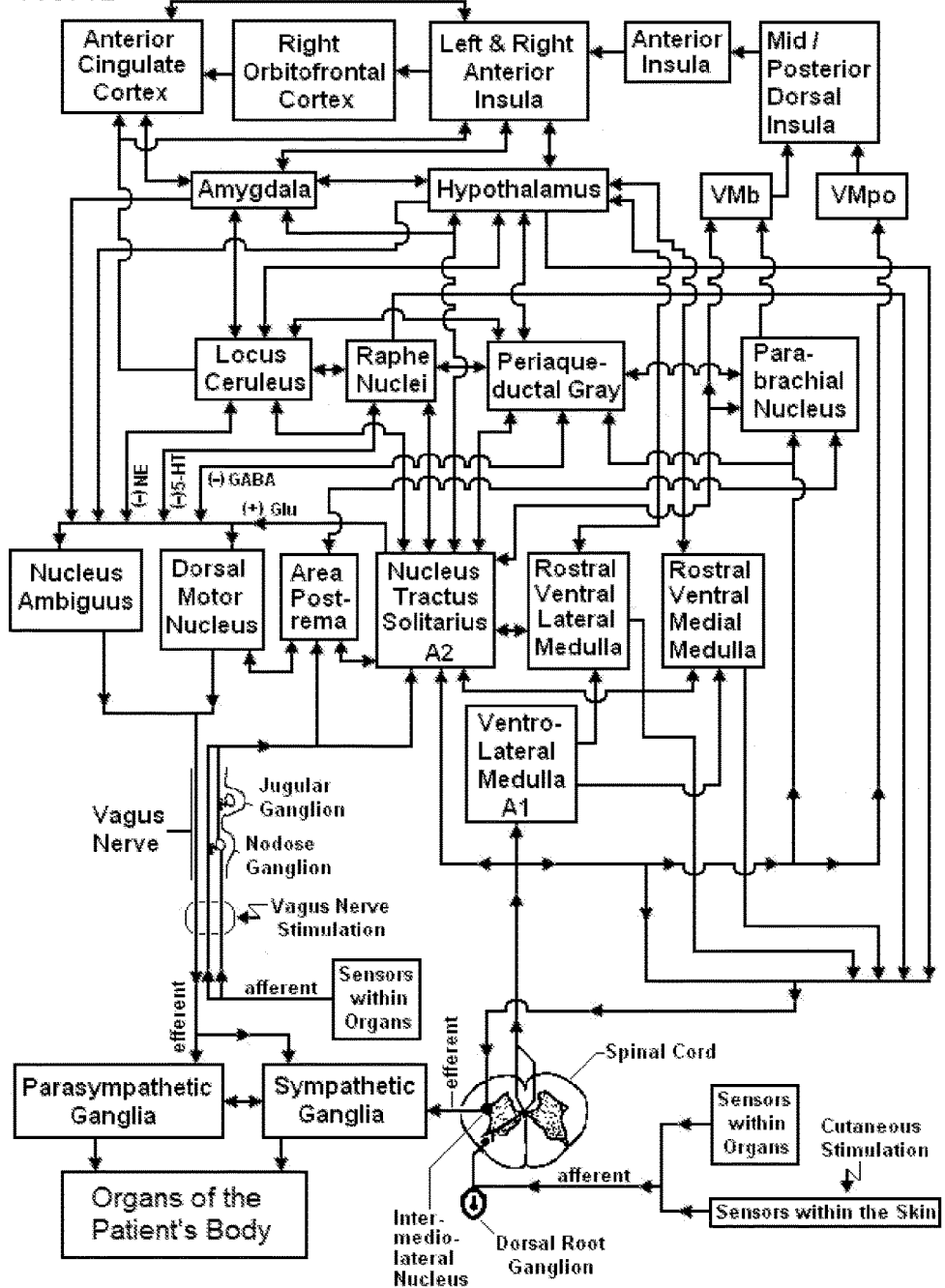
FIG. 12 shows structures within a patient's nervous system that may be modulated by electrical stimulation of a vagus nerve.

Selection of Stimulation Parameters to Activate or Suppress Selected Networks of the Brain FIG. 12 shows the location of the cervical stimulation as "Vagus Nerve Stimulation," relative to its connections with other anatomical structures that are potentially affected by the stimulation. In different embodiments of the invention, various brain and brainstem structures are preferentially modulated by the stimulation. Besides efferent output fibers that convey signals to the various organs in the body from the central nervous system, the vagus nerve conveys sensory (afferent) information about the state of the body's organs back to the central nervous system. Propagation of electrical signals in efferent and afferent directions is indicated by arrows in FIG. 12. If communication between structures is bidirectional, this is shown in FIG. 12 as a single connection with two arrows, rather than showing the efferent and afferent nerve fibers separately.

The vagus (or vagal) afferent nerve fibers arise from cell bodies located in the vagal sensory ganglia. These ganglia take the form of swellings found in the cervical aspect of the vagus nerve just caudal to the skull. There are two such ganglia, termed the inferior and superior vagal ganglia. They are also called the nodose and jugular ganglia, respectively (See FIG. 12). The jugular (superior) ganglion is a small ganglion on the vagus nerve just as it passes through the jugular foramen at the base of the skull. The nodose (inferior) ganglion is a ganglion on the vagus nerve located in the height of the transverse process of the first cervical vertebra.

Vagal afferents traverse the brainstem in the solitary tract, with some eighty percent of the terminating synapses being located in the nucleus of the tractus solitarius (or nucleus tractus solitarii, nucleus tractus solitarius, or NTS, see FIG. 12). The NTS projects to a wide variety of structures in the central nervous system, such as the amygdala, raphe nuclei, periaqueductal gray, nucleus paragigantocellurlais, olfactory tubercule, locus ceruleus, nucleus ambiguus and the hypothalamus. The NTS also projects to the parabrachial nucleus, which in turn projects to the hypothalamus, the thalamus, the amygdala, the anterior insula, and infralimbic cortex, lateral prefrontal cortex, and other cortical regions [JEAN A. The nucleus tractus solitarius: neuroanatomic, neurochemical and functional aspects. Arch Int Physiol Biochim Biophys 99(5,1991):A3-A52]. Such central projections are discussed below in connection with interoception and resting state neural networks.

With regard to vagal efferent nerve fibers, two vagal components have evolved in the brainstem to regulate peripheral parasympathetic functions. The dorsal vagal complex, consisting of the dorsal motor nucleus and its connections (see FIG. 12), controls parasympathetic function primarily below the level of the diaphragm (e.g. gut), while the ventral vagal complex, comprised of the nucleus ambiguus and nucleus retrofacial, controls functions primarily above the diaphragm in organs such as the heart, thymus and lungs, as well as other glands and tissues of the neck and upper chest, and specialized muscles such as those of the esophageal complex. For example, the cell bodies for the preganglionic parasympathetic vagal neurons that innervate the heart reside in the nucleus ambiguus, which is relevant to potential cardiovascular side effects that may be produced by vagus nerve stimulation.

Non-invasive stimulation of the cervical vagus nerve (nVNS) is a novel technology for treating various central nervous system disorders, primarily by stimulating specific afferent fibers of the vagus nerve to modulate brain function. This technology has been demonstrated in animal and human studies to treat a wide range of central nervous system disorders including headache (chronic and acute cluster and migraine), epilepsy, bronchoconstriction, anxiety disorders, depression, rhinitis, fibromyalgia, irritable bowel syndrome, stroke, traumatic brain injury, PTSD, Alzheimer's disease, autism, and others [See Cross Reference to Related Applications for the corresponding co-pending and commonly assigned applications, which are hereby incorporated by reference]. Many of these conditions have also been treated with limited efficacy using biofeedback, and the combined use of biofeedback with vagus nerve stimulation is intended to produce improved clinical results.

Applicants have discovered that as little as two-minutes of vagus nerve stimulation produces effects that may last up to 8 hours or longer, depending on the type and severity of indication. Broadly speaking, there are three components to the effects of nVNS on the brain. The strongest effect occurs during the two minute stimulation and results in significant changes in brain function that can be clearly seen as acute changes in autonomic function (e.g. measured using pupillometry, heart rate variability, galvanic skin response, or evoked potential) and activation and inhibition of various brain regions as shown in fMRI imaging studies. The second effect, of moderate intensity, lasts for 15 to 180 minutes after stimulation. Animal studies have shown changes in neurotransmitter levels in various parts of the brain that persist for several hours. The third effect, of mild intensity, lasts up to 8 hours and is responsible for the long lasting alleviation of symptoms seen clinically and, for example, in animal models of migraine headache. Thus, depending on the medical indication, whether it is a chronic or acute treatment, and the natural history of the disease, different treatment protocols may be used.

The vagus nerve stimulation may have excitatory and inhibitory effects. Some circuits involved in inhibition are illustrated in FIG. 12. Excitatory nerves within the dorsal vagal complex generally use glutamate as their neurotransmitter. To inhibit neurotransmission within the dorsal vagal complex, the present invention makes use of the bidirectional connections that the nucleus of the solitary tract (NTS) has with structures that produce inhibitory neurotransmitters, or it makes use of connections that the NTS has with the hypothalamus, which in turn projects to structures that produce inhibitory neurotransmitters. The inhibition is produced as the result of the stimulation waveforms that are disclosed in the previous section. Thus, acting in opposition to glutamate-mediated activation by the NTS of the area postrema and dorsal motor nucleus are: GABA, and/or serotonin, and/or norepinephrine from the periaqueductal gray, raphe nuclei, and locus coeruleus, respectively. FIG. 12 shows how those excitatory and inhibitory influences combine to modulate the output of the dorsal motor nucleus. Similar influences combine within the NTS itself, and the combined inhibitory influences on the NTS and dorsal motor nucleus produce a general inhibitory effect.

The activation of inhibitory circuits in the periaqueductal gray, raphe nucei, and locus coeruleus by the hypothalamus or NTS may also cause circuits connecting each of these structures to modulate one another. Thus, the periaqueductal gray communicates with the raphe nuclei and with the locus coeruleus, and the locus coeruleus communicates with the raphe nuclei, as shown in FIG. 12 [PUDOVKINA O L, Cremers T I, Westerink B H. The interaction between the locus coeruleus and dorsal raphe nucleus studied with dual-probe microdialysis. Eur J Pharmacol 7(2002); 445(1-2):37-42.; REICHLING D B, Basbaum A I. Collateralization of periaqueductal gray neurons to forebrain or diencephalon and to the medullary nucleus raphe magnus in the rat. Neuroscience 42(1,1991):183-200; BEHBEHANI M M. The role of acetylcholine in the function of the nucleus raphe magnus and in the interaction of this nucleus with the periaqueductal gray. Brain Res 252(2,1982):299-307]. The periaqueductal gray, raphe nucei, and locus coeruleus are also shown in FIG. 12 to project to many other sites within the brain.

The foregoing account of structures that are modulated by vagus nerve stimulation is provided as background information needed to understand an embodiment of the invention in which vagus nerve stimulation is used to modulate the activity of particular neural networks known as resting state networks. A neural network in the brain is accompanied by oscillations within the network. Low frequency oscillations are likely associated with connectivity at the largest scale of the network, while higher frequencies are exhibited by smaller sub-networks within the larger network, which may be modulated by activity in the slower oscillating larger network. The default network, also called the default mode network (DMN), default state network, or task-negative network, is one such network that is characterized by coherent neuronal oscillations at a rate lower than 0.1 Hz. Other large scale networks also have this slow-wave property, as described below [BUCKNER R L, Andrews-Hanna J R, Schacter D L. The brain's default network: anatomy, function, and relevance to disease. Ann N Y Acad Sci 1124(2008):1-38; PALVA J M, Palva S. Infra-slow fluctuations in electrophysiological recordings, blood-oxygenation-level-dependent signals, and psychophysical time series. Neuroimage 62(4,2012):2201-2211; STEYN-ROSS M L, Steyn-Ross D A, Sleigh J W, Wilson M T. A mechanism for ultra-slow oscillations in the cortical default network. Bull Math Biol 73(2,2011):398-416].

The default mode network corresponds to task-independent introspection (e.g., daydreaming), or self-referential thought. When the DMN is activated, the individual is ordinarily awake and alert, but the DMN may also be active during the early stages of sleep and during conscious sedation. During goal-oriented activity, the DMN is deactivated and one or more of several other networks, so-called task-positive networks (TPN), are activated. DMN activity is attenuated rather than extinguished during the transition between states, and is observed, albeit at lower levels, alongside task-specific activations. Strength of the DMN deactivation appears to be inversely related to the extent to which the task is demanding. Thus, DMN has been described as a task-negative network, given the apparent antagonism between its activation and task performance. The posterior cingulate cortex (PCC) and adjacent precuneus and the medial prefrontal cortex (mPFC) are the two most clearly delineated regions within the DMN [RAICHLE M E, Snyder A Z. A default mode of brain function: a brief history of an evolving idea. Neuroimage 37(4,2007):1083-1090; BROYD S J, Demanuele C, Debener S, Helps S K, James C J, Sonuga-Barke E J. Default-mode brain dysfunction in mental disorders: a systematic review. Neurosci Biobehav Rev 33(3,2009):279-96; BUCKNER R L, Andrews-Hanna J R, Schacter D L. The brain's default network: anatomy, function, and relevance to disease. Ann N Y Acad Sci 1124(2008):1-38; BUCKNER R L, Sepulcre J, Talukdar T, Krienen F M, Liu H, Hedden T, Andrews-Hanna J R, Sperling R A, Johnson K A. Cortical hubs revealed by intrinsic functional connectivity: mapping, assessment of stability, and relation to Alzheimer's disease. J Neurosci 29(2009):1860-1873; GREICIUS M D, Krasnow B, Reiss A L, Menon V. Functional connectivity in the resting brain: a network analysis of the default mode hypothesis. Proc Natl Acad Sci USA 100(2003): 253-258].

The term low frequency resting state networks (LFRSN or simply RSN) is used to describe both the task-positive and task-negative networks. Using independent component analysis (ICA) and related methods to assess coherence of fMRI Blood Oxygenation Level Dependent Imaging (BOLD) signals in terms of temporal and spatial variation, as well as variations between individuals, low frequency resting state networks in addition to the DMN have been identified, corresponding to different tasks or states of mind. They are related to their underlying anatomical connectivity and replay at rest the patterns of functional activation evoked by the behavioral tasks. That is to say, brain regions that are commonly recruited during a task are anatomically connected and maintain in the resting state (in the absence of any stimulation) a significant degree of temporal coherence in their spontaneous activity, which is what allows them to be identified at rest [SMITH S M, Fox P T, Miller K L, Glahn D C, Fox P M, et al. Correspondence of the brain's functional architecture during activation and rest. Proc Natl Acad Sci USA 106(2009): 13040-13045].

Frequently reported resting state networks (RSNs), in addition to the default mode network, include the sensorimotor RSN, the executive control RSN, up to three visual RSNs, two lateralized fronto-parietal RSNs, the auditory RSN and the temporo-parietal RSN. However, different investigators use different methods to identify the low frequency resting state networks, so different numbers and somewhat different identities of RSNs are reported by different investigators [COLE D M, Smith S M, Beckmann CF. Advances and pitfalls in the analysis and interpretation of resting-state FMRI data. Front Syst Neurosci 4(2010):8, pp. 1-15]. Examples of RSNs are described in publications cited by COLE and the following: ROSAZZA C, Minati L. Resting-state brain networks: literature review and clinical applications. Neurol Sci 32(5,2011):773-85; ZHANG D, Raichle M E. Disease and the brain's dark energy. Nat Rev Neurol 6(1,2010):15-28; DAMOISEAUX, J. S., Rombouts, S. A. R. B., Barkhof, F., Scheltens, P., Stam, C. J., Smith, S. M., Beckmann, C. F. Consistent resting-state networks across healthy subjects. Proc. Natl. Acad. Sci. U.S.A. 103 (2006): 13848-13853 FOX M D, Snyder A Z, Vincent J L, Corbetta M, Van Essen D C, Raichle M E. The human brain is intrinsically organized into dynamic, anticorrelated functional networks. Proc Natl Acad Sci USA102(2005):9673-9678; LI R, Wu X, Chen K, Fleisher A S, Reiman E M, Yao L. Alterations of Directional Connectivity among Resting-State Networks in Alzheimer Disease. AJNR Am J Neuroradiol. 2012 Jul. 12. [Epub ahead of print, pp. 1-6].

For example, the dorsal attention network (DAN) and ventral attention network (VAN) are two networks responsible for attentional processing. The VAN is involved in involuntary actions and exhibits increased activity upon detection of salient targets, especially when they appear in unexpected locations (bottom-up activity, e.g. when an automobile driver unexpectedly senses a hazard or unexpected situation). The DAN is involved in voluntary (top-down) orienting and increases activity after presentation of cues indicating where, when, or to what individuals should direct their attention [FOX M D, Corbetta M, Snyder A Z, Vincent J L, Raichle M E. Spontaneous neuronal activity distinguishes human dorsal and ventral attention systems. Proc Natl Acad Sci USA 103(2006):10046-10051; WEN X, Yao L, Liu Y, Ding M. Causal interactions in attention networks predict behavioral performance. J Neurosci 32(4,2012): 1284-1292]. The DAN is bilaterally centered in the intraparietal sulcus and the frontal eye field. The VAN is largely right lateralized in the temporal-parietal junction and the ventral frontal cortex. According to the present invention, it is generally desirable to activate DAN by vagus nerve stimulation when biofeedback efforts are in progress.

The attention systems (e.g., VAN and DAN) have been investigated long before their identification as resting state networks, and functions attributed to the VAN have in the past been attributed to the locus ceruleus/noradrenaline system [ASTON-JONES G, Cohen J D. An integrative theory of locus coeruleus-norepinephrine function: adaptive gain and optimal performance. Annu Rev Neurosci 28(2005):403-50; BOURET S, Sara S J. Network reset: a simplified overarching theory of locus coeruleus noradrenaline function. Trends Neurosci 28(11,2005):574-82; SARA S J, Bouret S. Orienting and Reorienting: The Locus Coeruleus Mediates Cognition through Arousal. Neuron 76(1, 2012):130-41; BERRIDGE C W, Waterhouse B D. The locus coeruleus-noradrenergic system: modulation of behavioral state and state-dependent cognitive processes. Brain Res Brain Res Rev 42(1,2003):33-84].

The attention systems originally described by PETERSON and Posner are more expansive than just the VAN and DAN system, with interacting anatomical components corresponding to alerting, orienting, and executive control [PETERSEN S E, Posner M I. The attention system of the human brain: 20 years after. Annu Rev Neurosci 35(2012): 73-89]. In that description, DAN and VAN comprise significant portions of the orienting system, and components largely involving locus ceruleus-norepinephrine function comprise the alerting system. Other resting state networks are involved with executive control [BECKMANN C F, DeLuca M, Devlin J T, Smith S M. Investigations into resting-state connectivity using independent component analysis. Philos Trans R Soc Lond B Biol Sci 360(1457, 2005):1001-1013].

MENON and colleagues describe the anterior insula as being at the heart of the ventral attention system [ECKERT M A, Menon V, Walczak A, Ahlstrom J, Denslow S, Horwitz A, Dubno J R. At the heart of the ventral attention system: the right anterior insula. Hum Brain Mapp 30(8,2009):2530-2541; MENON V, Uddin L Q. Saliency, switching, attention and control: a network model of insula function. Brain Struct Funct 214(5-6,2010):655-667]. However, SEELEY and colleagues used region-of-interest and independent component analyses of resting-state fMRI data to demonstrate the existence of an independent brain network comprised of both the anterior insula and dorsal ACC, along with subcortical structures including the amygdala, substantia nigra/ventral tegmental area, and thalamus. This network is distinct from the other well-characterized large-scale brain networks, e.g. the default mode network [SEELEY W W, Menon V, Schatzberg A F, Keller J, Glover G H, Kenna H, et al. Dissociable intrinsic connectivity networks for salience processing and executive control. J Neurosci 2007; 27(9):2349-2356]. CAUDA and colleagues found that the human insula is functionally involved in two distinct neural networks: i) the anterior pattern is related to the ventralmost anterior insula, and is connected to the rostral anterior cingulate cortex, the middle and inferior frontal cortex, and the temporoparietal cortex; ii) the posterior pattern is associated with the dorsal posterior insula, and is connected to the dorsal-posterior cingulate, sensorimotor, premotor, supplementary motor, temporal cortex, and to some occipital areas [CAUDA F, D'Agata F, Sacco K, Duca S, Geminiani G, Vercelli A. Functional connectivity of the insula in the resting brain. Neuroimage 55(1,2011):8-23; CAUDA F, Vercelli A. How many clusters in the insular cortex? Cereb Cortex. 2012 Sep. 30. (Epub ahead of print, pp. 1-2)]. TAYLOR and colleagues also report two such resting networks [TAYLOR K S, Seminowicz D A, Davis K D. Two systems of resting state connectivity between the insula and cingulate cortex. Hum Brain Mapp 30(9,2009):2731-2745]. DEEN and colleagues found three such resting state networks [DEEN B, Pitskel N B, Pelphrey K A. Three systems of insular functional connectivity identified with cluster analysis. Cereb Cortex 21(7,2011):1498-1506].

Before disclosing methods for modulating resting state networks using vagal nerve stimulation, we first discuss how stimulation of the vagus nerve can affect some of the relevant components of the brain, such as the insula (see FIG. 12). These structures are involved in the higher-level processing of sensory information. The sensory information consists not only of hearing, vision, taste & smell, and touch that may be used as biofeedback modalities, but also other sensory modalities such as proprioception, nociception and other forms of interoception.

For purposes of illustration in FIG. 12, we use interoceptive neural pathways leading to the insula [CRAIG A D. How do you feel—now? The anterior insula and human awareness. Nat Rev Neurosci 10(1,2009):59-70; BIELEFELDT K, Christianson J A, Davis B M. Basic and clinical aspects of visceral sensation: transmission in the CNS. Neurogastroenterol Motil 17(4,2005):488-499; MAYER E A, Naliboff B D, Craig A D. Neuroimaging of the brain-gut axis: from basic understanding to treatment of functional GI disorders. Gastroenterology 131(6,2006): 1925-1942]. Anatomically, interoceptive sensations are distinguished from surface touch (tactile) sensations by their association with the spinothalamic projection that ascend in the contralateral spinal cord, rather than with the dorsal column/medial lemniscal system which ascends the ipsilateral spinal cord. However, both contralateral and ipsilateral circuits are shown in the spinal cord in FIG. 12 to indicate that the discussion applies more generally to sensory processing, not just the interoception. In particular, it applies to also to the circuits along which cutaneous sensations arising from electrical stimulation are propagated [A. ANGEL. Processing of sensory information. Progress in Neurobiology 9(1977):1-122; G. WEDDELL and S. Miller. Cutaneous sensibility. Annual Review of Physiology 24(1962):199-222]. This is indicated in FIG. 12 as "Sensors within the skin", which are electrically stimulated as "Cutaneous stimulation."

Interoceptive sensations arise from signals sent by parasympathetic and sympathetic afferent nerves. The latter are considered to be the primary culprit for pain and other unpleasant emotional feelings, but parasympathetic afferents also contribute. Among afferents whose cell bodies are found in the dorsal root ganglia, the ones having type B cell bodies are most significant, which terminate in lamina I of the spinal and trigeminal dorsal horns. Other afferent nerves that terminate in the deep dorsal horn provide signals related to mechanoreceptive, proprioceptive and nociceptive activity.

Lamina I neurons project to many locations. First, they project to the sympathetic regions in the intermediomedial and intermediolateral cell columns of the thoracolumbar cord, where the sympathetic preganglionic cells of the autonomic nervous system originate (See FIG. 12). Second, in the medulla, lamina I neurons project to the A1 catecholaminergic cell groups of the ventrolateral medulla and then to sites in the rostral ventrolateral medulla (RVLM) which is interconnected with the sympathetic neurons that project to spinal levels. Only a limited number of discrete regions within the supraspinal central nervous system project to sympathetic preganglionic neurons in the intermediolateral column (see FIG. 12). The most important of these regions are the rostral ventral lateral medulla (RVLM), the rostral ventromedial medulla (RVMM), the midline raphe, the paraventricular nucleus (PVN) of the hypothalamus, the medullocervical caudal pressor area (mCPA), and the A5 cell group of the pons. The first four of these connections to the intermediolateral nucleus are shown in FIG. 12 [STRACK A M, Sawyer W B, Hughes J H, Platt K B, Loewy A D. A general pattern of CNS innervation of the sympathetic outflow demonstrated by transneuronal pseudorabies viral infections. Brain Res. 491(1,1989): 156-162].

The rostral ventral lateral medulla (RVLM) is the primary regulator of the sympathetic nervous system, sending excitatory fibers (glutamatergic) to the sympathetic preganglionic neurons located in the intermediolateral nucleus of the spinal cord. Vagal afferents synapse in the NTS, and their projections reach the RVLM via the caudal ventrolateral medulla. However, resting sympathetic tone also comes from sources above the pons, from hypothalamic nuclei, various hindbrain and midbrain structures, as well as the forebrain and cerebellum, which synapse in the RVLM. Only the hypothalamic projection to the RVLM is shown in FIG. 12.

The RVLM shares its role as a primary regulator of the sympathetic nervous system with the rostral ventromedial medulla (RVMM) and medullary raphe. Differences in function between the RVLM versus RVMM/medullary raphe have been elucidated for cardiovascular control, but are not well characterized for control of other organs such as those of the gut. Differential control of the RVLM by the hypothalamus may also occur via circulating hormones such as vasopressin. The RVMM contains at least three populations of nitric oxide synthase neurons that send axons to innervate functionally similar sites in the NTS and nucleus ambiguus. Circuits connecting the RVMM and RVLM may be secondary, via the NTS and hypothalamus.

In the medulla, lamina I neurons also project another site, namely, to the A2 cell group of the nucleus of the solitary tract, which also receives direct parasympathetic (vagal and glossopharyngeal) afferent input. As indicated above, the nucleus of the solitary tract projects to many locations, including the parabrachial nucleus. In the pons and mesencephalon, lamina I neurons project to the periaqueductal grey (PAG), the main homeostatic brainstem motor site, and to the parabrachial nucleus. Sympathetic and parasympathetic afferent activity is integrated in the parabrachial nucleus. It in turn projects to the insular cortex by way of the ventromedial thalamic nucleus (VMb, also known as VPMpc). A direct projection from lamina I to the ventromedial nucleus (VMpo), and a direct projection from the nucleus tractus solitarius to the VMb, provide a rostrocaudally contiguous column that represents all contralateral homeostatic afferent input. They project topographically to the mid/posterior dorsal insula (See FIG. 12).

In humans, this cortical image is re-represented in the anterior insula on the same side of the brain. The parasympathetic activity is re-represented in the left (dominant) hemisphere, whereas the sympathetic activity is re-represented in the right (non-dominant) hemisphere. These re-representations provide the foundation for a subjective evaluation of interoceptive state, which is forwarded to the orbitofrontal cortex (See FIG. 12).

The right anterior insula is associated with subjective awareness of homeostatic emotions (e.g., visceral and somatic pain, temperature, sexual arousal, hunger, and thirst) as well as all emotions (e.g., anger, fear, disgust, sadness, happiness, trust, love, empathy, social exclusion). This region is intimately interconnected with the anterior cingulate cortex (ACC). Unpleasant sensations are directly correlated with ACC activation [KLIT H, Finnerup N B, Jensen T S. Central post-stroke pain: clinical characteristics, pathophysiology, and management. Lancet Neurol 8(9, 2009):857-868]. The anterior cingulate cortex and insula are both strongly interconnected with the orbitofrontal cortex, amygdala, hypothalamus, and brainstem homeostatic regions, of which only a few connections are shown in FIG. 12.

Methods of the present invention comprise modulation of resting state networks containing or interacting with the insula using vagus nerve stimulation. A first method directly targets the front end of the interoceptive pathways shown in FIG. 12 (nucleus tractus solitarius, area postrema, and dorsal motor nucleus). The second method targets the distal end of the interoceptive pathways (anterior insula and anterior cingulate cortex).

According to the first method, electrical stimulation of A and B fibers alone of a vagus nerve causes increased inhibitory neurotransmitters in the brainstem, which in turn inhibits signals sent to the parabrachial nucleus, VMb and VMpo. The stimulation uses special devices and a special waveform (described above), which minimize effects involving C fibers that might produce unwanted side-effects. The electrical stimulation first affects the dorsal vagal complex, which is the major termination site of vagal afferent nerve fibers. The dorsal vagal complex consists of the area postrema (AP), the nucleus of the solitary tract (NTS) and the dorsal motor nucleus of the vagus. The AP projects to the NTS and dorsal motor nucleus of the vagus bilaterally. It also projects bilaterally to the parabrachial nucleus and receives direct afferent input from the vagus nerve. Thus, the area postrema is in a unique position to receive and modulate ascending interoceptive information and to influence autonomic outflow [PRICE CJ, Hoyda T D, Ferguson A V. The area postrema: a brain monitor and integrator of systemic autonomic state. Neuroscientist 14(2,2008):182-194].

Projections to and from the locus ceruleus are particularly significant in the present invention because they are also used in the second method that is described below. The vagus nerve transmits information to the locus ceruleus via the nucleus tractus solitarius (NTS), which has a direct projection to the dendritic region of the locus ceruleus. Other afferents to, and efferents from, the locus ceruleus are described by SARA et al, SAMUELS et al, and ASTON-JONES [SARA S J, Bouret S. Orienting and Reorienting: The Locus Coeruleus Mediates Cognition through Arousal. Neuron 76(1,2012):130-41; SAMUELS E R, Szabadi E. Functional neuroanatomy of the noradrenergic locus coeruleus: its roles in the regulation of arousal and autonomic function part I: principles of functional organization. Curr Neuropharmacol 6(3):235-53; SAMUELS, E. R., and Szabadi, E. Functional neuroanatomy of the noradrenergic locus coeruleus: its roles in the regulation of arousal and autonomic function part II: physiological and pharmacological manipulations and pathological alterations of locus coeruleus activity in humans. Curr. Neuropharmacol. 6(2008), 254-285; Gary ASTON-JONES. Norepinephrine. Chapter 4 (pp. 47-57) in: Neuropsychopharmacology: The Fifth Generation of Progress (Kenneth L. Davis, Dennis Charney, Joseph T. Coyle, Charles Nemeroff, eds.) Philadelphia: Lippincott Williams & Wilkins, 2002].

In addition to the NTS, the locus ceruleus receives input from the nucleus gigantocellularis and its neighboring nucleus paragigantocellularis, the prepositus hypoglossal nucleus, the paraventricular nucleus of the hypothalamus, Barrington's nucleus, the central nucleus of the amygdala, and prefrontal areas of the cortex. These same nuclei receive input from the NTS, such that stimulation of the vagus nerve may modulate the locus ceruleus via the NTS and a subsequent relay through these structures.

The locus ceruleus has widespread projections throughout the cortex [SAMUELS E R, Szabadi E. Functional neuroanatomy of the noradrenergic locus coeruleus: its roles in the regulation of arousal and autonomic function part I: principles of functional organization. Curr Neuropharmacol 6 (3):235-53]. It also projects to subcortical regions, notably the raphe nuclei, which release serotonin to the rest of the brain. An increased dorsal raphe nucleus firing rate is thought to be secondary to an initial increased locus ceruleus firing rate from vagus nerve stimulation [Adrienne E. DORR and Guy Debonnelv. Effect of vagus nerve stimulation on serotonergic and noradrenergic transmission. J Pharmacol Exp Ther 318(2,2006):890-898; MANTA S, Dong J, Debonnel G, Blier P. Enhancement of the function of rat serotonin and norepinephrine neurons by sustained vagus nerve stimulation. J Psychiatry Neurosci 34(4,2009):272-80]. The locus ceruleus also has projections to autonomic nuclei, including the dorsal motor nucleus of the vagus, as shown in FIG. 1A [FUKUDA, A., Minami, T., Nabekura, J., Oomura, Y. The effects of noradrenaline on neurones in the rat dorsal motor nucleus of the vagus, in vitro. J. Physiol., 393 (1987): 213-231; MARTINEZ-PENA y Valenzuela, I., Rogers, R. C., Hermann, G. E., Travagli, R. A. (2004) Norepinephrine effects on identified neurons of the rat dorsal motor nucleus of the vagus. Am. J. Physiol. Gas-trointest. Liver Physiol., 286, G333-G339; TERHORST, G. J., Toes, G. J., Van Willigen, J. D. Locus coeruleus projections to the dorsal motor vagus nucleus in the rat. Neuroscience, 45(1991): 153-160].

Figure 13:
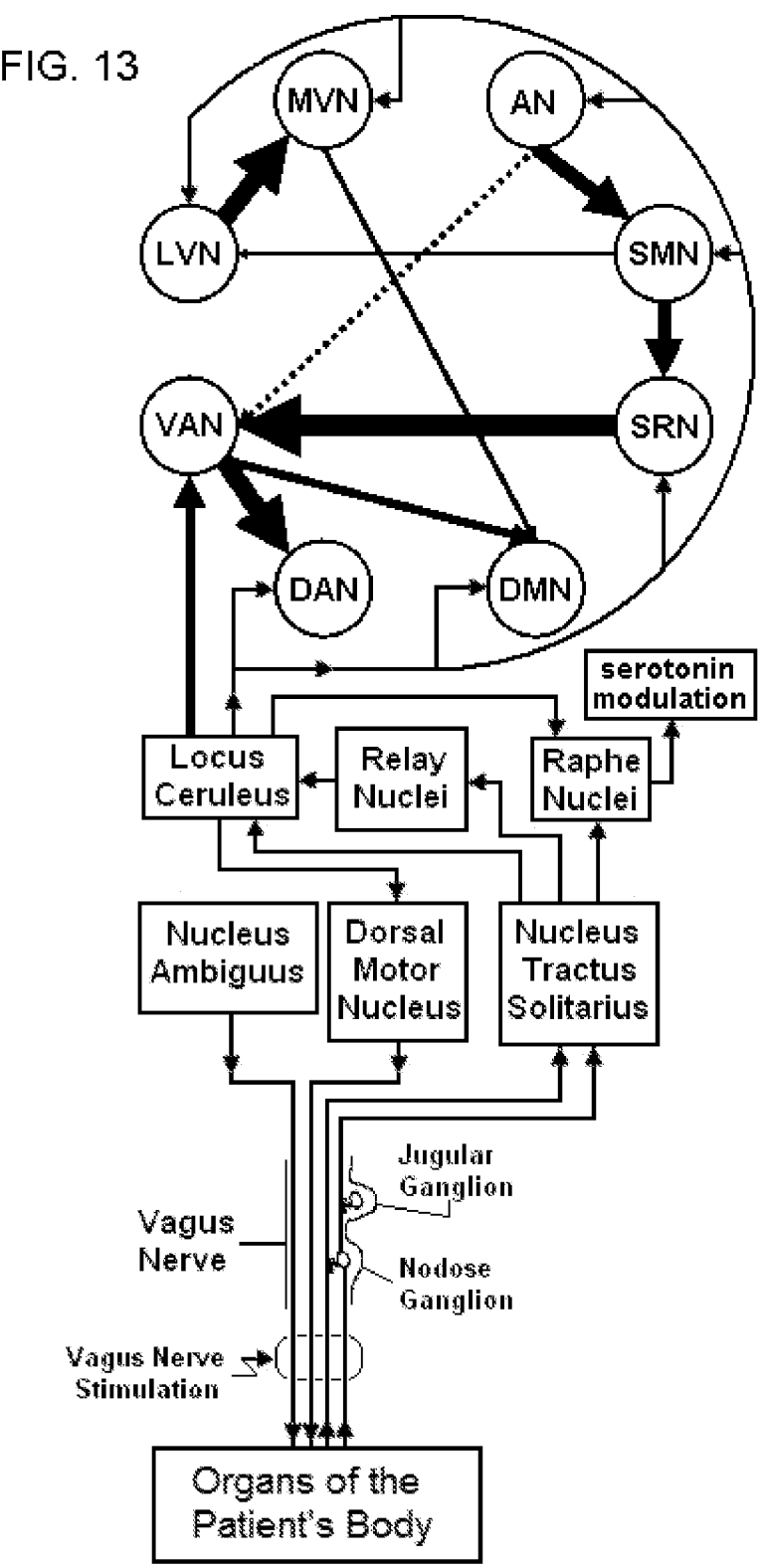
FIG. 13 shows functional networks within the brain (resting state networks) that may be modulated by electrical stimulation of a vagus nerve.

Selective Activation of Resting State Networks by Stimulation of the Cervical Vagus Nerve The above-mentioned circuits shown can be represented in terms of functional resting state networks that may also contain various components that are shown in FIG. 12. A simplified representation of those networks is shown in FIG. 13. For purposes of discussion, we adopt the set of resting state networks identified by LI et al, with the understanding that according to the above-cited publications, a more or less detailed set could also be adopted [LI R, Wu X, Chen K, Fleisher A S, Reiman E M, Yao L. Alterations of Directional Connectivity among Resting-State Networks in Alzheimer Disease. AJNR Am J Neuroradiol. 2012 Jul. 12. [Epub ahead of print, pp. 1-6]. A similar set of resting state networks is described by DING et al [DING JR, Liao W, Zhang Z, Mantini D, Xu Q, Wu G R, Lu G, Chen H. Topological fractionation of resting-state networks. PLoS One 6(10, 2011):e26596, pp. 1-9]. FIG. 13 also shows connections between the networks, with the larger arrows indicating stronger connections. Solid and dashed arrows are, respectively, for positive and negative connections. According to the present invention, by activating particular resting state networks using vagus nerve stimulation, one may preferentially generate evoked potentials that correspond to those resting state networks, and conversely, confirm that particular resting state networks have been activated.

As described above, the dorsal attention network (DAN) and ventral attention network (VAN) are two networks responsible for attentional processing. The VAN is involved in involuntary actions and exhibits increased activity upon detection of salient targets, especially when they appear in unexpected locations (bottom-up activity, e.g. when an automobile driver unexpectedly senses a hazard). The DAN is involved in voluntary (top-down) orienting and increases activity after presentation of cues indicating where, when, or to what individuals should direct their attention [FOX M D, Corbetta M, Snyder A Z, Vincent J L, Raichle M E. Spontaneous neuronal activity distinguishes human dorsal and ventral attention systems. Proc Natl Acad Sci USA 103(2006):10046-10051; WEN X, Yao L, Liu Y, Ding M. Causal interactions in attention networks predict behavioral performance. J Neurosci 32(4,2012):1284-1292]. The DAN is bilaterally centered in the intraparietal sulcus and the frontal eye field. The VAN is largely right lateralized in the temporal-parietal junction and the ventral frontal cortex.

The sensory-motor network (SMN) is the network covering the somatosensory, premotor, and supplementary motor cortices. Cutaneous stimulation would preferentially activate the SMN, so the vagus nerve stimulation may be directed to affect the SMN to enhance the cutaneous signals. The lateral visual network (LVN) and medial visual network (MVN) are two networks for visual processing and are respectively located in the lateral and medial parts of the visual cortex. The auditory network (AN) is responsible for auditory processing and is located in the bilateral superior temporal gyrus and in the primary and secondary auditory cortices. The LVN, MVN, AN, and SMN are four networks related to sensory processing, and the DMN, SRN, DAN, and VAN are associated with higher cognitive function.

The present invention modulates the activity of these resting state networks via the locus ceruleus by electrically stimulating the vagus nerve, as indicated in FIG. 13. Stimulation of a network by that route may activate or deactivate a resting state network, depending on the detailed configuration of adrenergic receptor subtypes within the network and their roles in enhancing or depressing neural activity within the network, as well as subsequent network-to-network interactions.

According to the invention, one key to preferential stimulation of a particular resting state network, such as those involving the insula, is to use a vagus nerve stimulation signal that entrains to the signature EEG pattern of that network (see below and MANTINI D, Perrucci M G, Del Gratta C, Romani G L, Corbetta M. Electrophysiological signatures of resting state networks in the human brain. Proc Natl Acad Sci USA 104(32,2007):13170-13175). By this EEG entrainment method, it may be possible to preferentially activate, attenuate or deactivate particular networks, such as DAN or VAN. Activation of another network such as the SMN, VAN or DMN may also produce the same effect, via network-to-network interactions. Although the locus ceruleus is presumed to project to all of the resting networks, it is thought to project most strongly to the ventral attention network (VAN) [CORBETTA M, Patel G, Shulman GL. The reorienting system of the human brain: from environment to theory of mind. Neuron 58(3,2008):306-24; MANTINI D, Corbetta M, Perrucci M G, Romani G L, Del Gratta C. Large-scale brain networks account for sustained and transient activity during target detection. Neuroimage 44(1,2009):265-274]. Thus, deactivation of a particular network may also be attempted by activating another resting state network, because the brain switches between them.

Stimulation waveforms may be constructed by superimposing or mixing the burst waveform shown in FIGS. 11B and 11C, in which each component of the mixture may have a different period T, effectively mixing different burst-per-second waveforms. The relative amplitude of each component of the mixture may be chosen to have a weight according to correlations in different bands in an EEG for a particular resting state network. Thus, MANTINI et al performed simultaneous fMRI and EEG measurements and found that each resting state network has a particular EEG signature [see FIG. 3 in: MANTINI D, Perrucci M G, Del Gratta C, Romani G L, Corbetta M. Electrophysiological signatures of resting state networks in the human brain. Proc Natl Acad Sci USA 104(32,2007):13170-13175]. They reported relative correlations in each of the following bands, for each resting state network that was measured: delta (1-4 Hz), theta (4-8 Hz), alpha (8-13 Hz), beta (13-30 Hz), and gamma (30-50 Hz) rhythms. For recently-identified resting state networks, measurement of the corresponding signature EEG networks will have to be performed.

According to the present embodiment of the invention, multiple signals shown in FIGS. 11B and 11C are constructed, with periods T that correspond to a location near the midpoint of each of the EEG bands (e.g., using the MINATI data, T equals approximately 0.4 sec, 0.1667 sec, 0.095 sec, 0.0465 sec, and 0.025 sec, respectively). A more comprehensive mixture could also be made by mixing more than one signal for each band. These signals are then mixed, with relative amplitudes corresponding to the weights measured for any particular resting state network, and the mixture is used to stimulate the vagus nerve of the patient. Phases between the mixed signals are adjusted to optimize the fMRI signal for the resting state network that is being stimulated, thereby producing entrainment with the resting state network. Stimulation of a network may activate or deactivate a network, depending on the detailed configuration of adrenergic receptors within the network and their roles in enhancing or depressing neural activity within the network, as well as subsequent network-to-network interactions. It is understood that variations of this method may be used when different combined fMRI-EEG procedures are employed and where the same resting state may have different EEG signatures, depending on the circumstances [WU C W, Gu H, Lu H, Stein E A, Chen J H, Yang Y. Frequency specificity of functional connectivity in brain networks. Neuroimage 42(3,2008):1047-1055; LAUFS H. Endogenous brain oscillations and related networks detected by surface EEG-combined fMRI. Hum Brain Mapp 29(7, 2008):762-769; MUSSO F, Brinkmeyer J, Mobascher A, Warbrick T, Winterer G. Spontaneous brain activity and EEG microstates. A novel EEG/fMRI analysis approach to explore resting-state networks. Neuroimage 52(4,2010): 1149-1161; ESPOSITO F, Aragri A, Piccoli T, Tedeschi G, Goebel R, Di Salle F. Distributed analysis of simultaneous EEG-fMRI time-series: modeling and interpretation issues. Magn Reson Imaging 27(8,2009):1120-1130; FREYER F, Becker R, Anami K, Curio G, Villringer A, Ritter P. Ultra-high-frequency EEG during fMRI: pushing the limits of imaging-artifact correction. Neuroimage 48(1,2009):94-108]. Once the network is entrained, one may also attempt to change the signature EEG pattern of a network, by slowly changing the frequency content of the stimulation & EEG pattern of the network to which the stimulator is initially entrained. An objective in this case would be to modify the frequency content of the resting state signature EEG.

Protocols for Evoking Potentials by Stimulation of the Cervical Vagus Nerve

As described in connection with FIG. 1B, the present invention makes use of methods that have been described previously for stimulating and recording visual, auditory, somatosensory, olfactory, gustatory, and vestibular evoked potentials [William R. GOFF. Human average evoked potentials: procedures for stimulating and recording. Chapter 3, pp. 101-156 in: Bioelectric Recording Techniques. Part B. Electroencephalography and Human Brain Potentials (Richard F. Thompson and Michale M. Patterson, eds). New York: Academic Press, 1974; David REGAN. Human Brain Electrophysiology. Evoked potentials and evoked magnetic fields in science and medicine. New York: Elsevier Science Publishing Co., 1989, pp. 1-672; Terence W. PICTON, Otavio G. Lins and Michael Scherg. The recording and analysis of event-related potentials. Chapter 1 (pp. 3-73) in Handbook of Neuropsychology, Vol. 10 (F. Boller and J. Grafman, eds). Amsterdam: Elsevier Science B.V., 1995; Monica FABIANI, Gabriele Gratton and Michael G. H. Coles. Event Related Potentials. Methods, Theory, and Applications. Chapter 3, pp. 53-84 In: John T. Cacioppo, Louis G. Tassinary and Gary G. Berntson (eds). Handbook of Psychophysiology, 2nd Ed. Cambridge: Cambridge University Press, 2000; Steven J. LUCK. An introduction to event-related potentials and their neural origins. Chapter 1 (pp. 1-50) in: Steven J. LUCK. An Introduction to the Event-Related Potential Technique. Cambridge, Mass.: MIT Press, 2005; Todd C. HANDY (ed). Event-related Potentials: A Methods Handbook. Camridge, Mass.: MIT Press, 2005, pp. 1-380; Steven J LUCK and Emily S Kappenman, eds. Oxford handbook of event-related potential components. Oxford: Oxford University Press, 2012, pp. 1-626]. Thus, a stimulus for one or more of these senses may be generated by the device of the present invention ("Other Sensory Stimuli" in FIG. 1B), which then activates receptors for the corresponding sense(s) ("Other Sense Organs" in FIG. 1B), and the resulting neuronal signal is then transmitted to the central nervous system, for processing by brain structures. The corresponding electrical currents within the brain are detected as electrical potentials using electrodes on the scalp of the subject, and those potentials are then recorded by data acquisition components of the system, as a function of time relative to the time-of-onset of the sensory stimulus (see FIG. 1B).

If any of the above-mentioned senses is stimulated with a stimulus having high enough intensity, the subject may sense the stimulus as being painful. However, if the activation of pain sensors is the primary subject of the evoked potential investigation, the stimulus is customarily chosen to be a focused pulse of laser light [TREEDE R D, Lorenz J, Baumgärtner U. Clinical usefulness of laser-evoked potentials. Neurophysiol Clin 33(6,2003):303-314; GARCIA-LARREA L, Frot M, Valeriani M. Brain generators of laser-evoked potentials: from dipoles to functional significance; Neurophysiol Clin 33(6,2003):279-292]. In the present invention, the investigator may also stimulate the cervical cutaneous sense receptors with an electrical current that evokes pain on the part of the subject (see FIG. 1B). In fact, in preliminary experiments, the investigator will ordinarily increase the electrical current arising from the vagus nerve stimulator in such a way as to ascertain the range of currents (and stimulation voltages) that first reach a sensory threshold and that eventually first produce a painful sensation in the skin on the neck of the patient.

Ordinarily, the sensory stimuli that are applied in order to evoke potentials correspond to exteroceptive sense organs. However, the stimulation of interoceptive receptors may result in the generation of evoked potentials as well, which has been investigated primarily by stimulating gastrointestinal interoceptors that can result in the sensation of internal pain [SARKAR S, Hobson A R, Furlong P L, Woolf C J, Thompson D G, Aziz Q. Central neural mechanisms mediating human visceral hypersensitivity. Am J Physiol Gastrointest Liver Physiol 281(5,2001):G1196-G1202]. Such evoked potentials are relevant to the present invention because gastrointestinal sensory information may be transmitted by branches of the vagus nerve [TOUGAS G, Hudoba P, Fitzpatrick D, Hunt R H, Upton A R. Cerebral evoked potential responses following direct vagal and esophageal electrical stimulation in humans. American Journal of Physiology 264(3 Pt 1,1993):G486-G491]. However, a caveat is that the evoked potential latencies observed in such experiments are extremely long and are considered to be responses induced by polysynaptic neural transmission, not directly reflecting ascending conduction of the vagus nerve [USAMI K, Kawai K, Sonoo M, Saito N. Scalp-recorded evoked potentials as a marker for afferent nerve impulse in clinical vagus nerve stimulation. Brain Stimul 6(4,2013):615-623].

Vagus nerve stimulation has also been used in other attempts to evoke potentials that are measured with scalp electrodes. In the earliest investigations, the potentials that were purportedly evoked by invasive vagus nerve stimulation were determined to be artifacts involving the stimulation of muscle, which are generated in the region of the stimulating electrodes in the neck area [HAMMOND E J, Uthman B M, Reid S A, Wilder B J. Electrophysiologic studies of cervical vagus nerve stimulation in humans: II. Evoked potentials. Epilepsia 33(6,1992):1021-1028]. Evoked potentials were also described in U.S. Pat. No. 8,150,508 and U.S. Pat. No. 8,280,505, both entitled Vagus nerve stimulation method, to CRAIG, and U.S. Pat. No. 8,615,309, entitled Microburst electrical stimulation of cranial nerves for the treatment of medical conditions, to CRAIG. However, those patents pertain only to the production of evoked potentials through stimulation of a nerve with an implanted nerve stimulator, and they did not disclose the approximate latencies of purported evoked potentials, which could arise artificially through the stimulation of muscle as described above. These considerations apply also to U.S. Pat. No. 7,801,601, entitled Controlling neuromodulation using stimulus modalities, to MASCHINO et al.

In other investigations, a branch of the vagus nerve was electrically stimulated at the tragus of the ear, and evoked potentials were purportedly measured [FALLGATTER A J, Neuhauser B, Herrmann M J, Ehlis A-C, Wagener A, Scheuerpflug P, Reiners K and Riederer P. Far field potentials from the brain stem after transcutaneus vagus nerve stimulation. J Neural Transm 110(2003):1437-1443; FALLGATTER A J, Ehlis A-C, Ringel T M, Herrmann M J. Age effect on far field potentials from the brain stem after transcutaneus vagus nerve stimulation. Int J Psychophysiol 56(2005):37-43; POLAK T, Ehlis A C, Langer J B M, Plichta M M, Metzger F, Ringel T M, and Fallgatter A J. Noninvasive measurement of vagus activity in the brain stem—a methodological progress towards earlier diagnosis of dementias? J Neural Transm 114(2007):613-619; POLAK T, Markulin F, Ehlis A-C, Langer J B M, Ringel T M, Fallgatter A J. Far field potentials from brain stem after transcutaneous vagus nerve stimulation: optimization of stimulation and recording parameters. J Neural Transm 116(2009):1237-1242]. However, those evoked potentials have also been shown to be artifacts involving the stimulation of muscle [B. LEUTZOW, Lange J, Gibb A, Schroeder H, Nowak A, Wendt M, Usichenko T I. Vagal Sensory Evoked Potentials Disappear Under the Neuromuscular Block—An Experimental Study. Brain Stimul 6(5,2013):812-816].

Other investigators have attempted to detect changes in EEG waveforms following vagus nerve stimulation, but measurement of the EEG waveform was not time-locked to the nerve stimulation, as would be required for the measurement of an evoked potential. The acute or chronic effects of vagus nerve stimulation on surface EEG waveforms is difficult to detect anyway [Michael BEWERNITZ, Georges Ghacibeh, Onur Seref, Panos M. Pardalos, Chang-Chia Liu, and Basim Uthman. Quantification of the impact of vagus nerve stimulation parameters on electroencephalographic measures. AIP Conf. Proc. DATA MINING, SYSTEMS ANALYSIS AND OPTIMIZATION IN BIOMEDICINE; Nov. 5, 2007, Volume 953, pp. 206-219; Michael Andrew BEWERNITZ. Data mining and time series analysis of brain dynamical behavior with applications in epilepsy. PhD. Dissertation. Gainesville, Fla.: University of Florida. 2008. pp: 1-246]. However, such effects may exist nevertheless, although they too might be the artificial result of muscle stimulation [KOO B. EEG changes with vagus nerve stimulation. J Clin Neurophysiol. 18(5,2001):434-41; KUBA R, Guzaninová M, Brázdil M, Novák Z, Chrastina J, Rektor I. Effect of vagal nerve stimulation on interictal epileptiform discharges: a scalp EEG study. Epilepsia. 43(10,2002):1181-8; RIZZO P, Beelke M, De Carli F, Canovaro P, Nobili L, Robert A, Fornaro P, Tanganelli P, Regesta G, Ferrillo F. Modifications of sleep EEG induced by chronic vagus nerve stimulation in patients affected by refractory epilepsy. Clin Neurophysiol. 115(3,2004):658-664; Zhaoyang CHEN, Hongwei Hao, Luming Li, Jie Dong. Wavelet Transform for Rabbit EEG with Vagus Nerve Electric Stimulation. Proceedings of the 28th IEEE EMBS Annual International Conference New York City, USA, Aug. 30-Sep. 3, 2006 pp. 1715-1718].

Recently, USAMI and colleagues tried once again to measure credible, non-artifactual potentials that are evoked by the invasive, direct stimulation of the cervical vagus nerve [USAMI K, Kawai K, Sonoo M, Saito N. Scalp-recorded evoked potentials as a marker for afferent nerve impulse in clinical vagus nerve stimulation. Brain Stimul 6(4,2013):615-623]. They determined that some of the early latency peaks and troughs in the evoked potential waveform actually had their origin in currents within the central nervous system, as evidenced by the fact that they do not disappear upon the administration of muscle relaxant to the subject. Applicants also performed the cervical vagus nerve stimulation experiment that was reported by USAMI, except that in our experiments, the cervical vagus nerve was stimulated noninvasively using electrodes positioned on the subject's neck. We measured the location of peaks and troughs in the potentials that were evoked by the noninvasive vagus nerve stimulation and found that they were similar to those of the peaks and troughs that had been determined to be non-artifactual by USAMI et al. The results are shown in FIG. 14A, which displays the voltages that were measured with scalp electrodes, as a function of time since the onset of the electrical stimulus. The latency extrema are identified there with the labels P1, N1, and P2 as in FIG. 1 of USAMI et al. The latencies were also found to be similar to those described by USAMI et al. Thus, whereas the P1, N1, and P2 peak or trough latencies in FIG. 14A were found at 3.1, 5.3, and 16.7 msec, respectively, the ones described by USAMI et al. were measured to be 2.8, 3.6, and 11.3 msec, respectively. These relatively small differences may be attributed to the fact that our vagus nerve stimulation was noninvasive, whereas theirs was invasive, as well as to differences in the stimulation currents in the vicinity the vagus nerve itself, and to differences in evoked potential waveforms between individuals.

The similarity between the evoked potentials that we measured, versus those measured by USAMI et al, are evidence that our noninvasive vagus nerve stimulation experiments did in fact produce evoked potentials that result from action potentials that we generated in the cervical vagus nerve. An alternate explanation for the evoked potentials that we measured is that they were evoked by the stimulation of cutaneous receptors that lie between the surface of the skin and the cervical vagus nerve. However, that explanation is not likely because evoked potentials that are produced by the electrical stimulation of cutaneous receptors have latencies that are considerably different than the P1, N1, and P2 latency values that are shown in FIG. 14A [SLIMP J C, Rubner D E, Snowden M L, Stolov W C. Dermatomal somatosensory evoked potentials: cervical, thoracic, and lumbosacral levels. Electroencephalogr Clin Neurophysiol 84(1,1992):55-70; KRAMER J K, Taylor P, Steeves J D, Curt A. Dermatomal somatosensory evoked potentials and electrical perception thresholds during recovery from cervical spinal cord injury. Neurorehabil Neural Repair 24(4,2010):309-317]. Furthermore, when the noninvasive stimulator electrodes were displaced slightly from the positions used to produce the data shown in FIG. 14A, the evoked potential waveform was measured instead to be what is shown in FIG. 14B, which is dissimilar to what is shown in FIG. 14A. Thus, the evoked potential shown in FIG. 14B is not likely to be due to the stimulation of the vagus nerve, but is likely evoked by stimulation of receptors in the skin and/or muscle that are situated near the vagus nerve.

Given that a particular evoked potential can be quantified that represents stimulation of the vagus nerve, the operator can use this measurement to confirm that action potentials have been created in the vagus nerve during electrical stimulation. In this manner, the operator may, for example, vary a characteristic of the electrical impulses generator by the vagus nerve stimulator in order to ensure that such stimulation is effectively stimulating the vagus nerve at a therapeutic level. For example, if such stimulation does not initially generate the evoked potentials that would confirm the firing of the action potentials in the vagus nerve, the operator may vary aspects of the signal, such as the amplitude, frequency, pulse width and/or duty cycle until such an evoked potential is generated. In addition or alternatively, the operator may vary the placement or orientation of the device on the subject's neck to ensure proper stimulation of the vagus nerve. As another alternative, the operator may position the vagus nerve stimulator onto the other side of the patient's neck (left to right or vice versa) in an attempt to optimize the stimulation. Note that the present methods for optimizing the position of the vagus nerve stimulation electrodes are different from the ones disclosed in U.S. Pat. No. 8,412,338, entitled Devices and methods for optimizing electrode placement for anti-inflammatory stimulation, to FALTYS. The FALTYS patent is concerned with positioning of the electrode based on the appearance of stimulation artifacts, which he defines as a signal or signals resulting from the electrode that is not part of the desired stimulation. In contrast, the present disclosure is concerned with the positioning of the electrode based on the appearance in an evoked potential waveform of a feature that is thought NOT to be a stimulation artifact.

One application of direct vagus nerve stimulation at the neck is to modulate neurotransmitter levels within the central nervous system of patients with certain medical disorders such as primary headache (e.g., migraine), or fibromyalgia, who have a demonstrable habituation deficit with regard to their evoked potentials. Thus, the patient may be tested (without feedback or biofeedback) by stimulating "other sense organs" or the cervical cutaneous senses in FIG. 1B, and measuring the corresponding evoked potentials, over an extended period of time (e.g., visual, auditory, or traditional somatosensory EPs, as reviewed in COPPOLA G, Pierelli F, Schoenen J. Habituation and migraine. Neurobiol Learn Mem 92(2,2009):249-259). The patients who do not exhibit significant habituation in their evoked potentials, in response to the sensory stimulation over a prolonged period of time, are then subjected to an acute direct stimulation of the vagus nerve. The patient is then retested (again without feedback or biofeedback) by stimulating "other sense organs" and re-measuring the previously-measured evoked potentials (visual, auditory, or traditional somatosensory EPs). For some of the individuals (the "responders"), the effect of the intervening acute vagus nerve stimulation is to significantly reduce the magnitude of features of evoked potentials, thereby artificially effecting a form of EP habituation. Those individuals are therefore candidates for chronic treatment of their migraine headaches, by performing the vagus nerve stimulation on a regular basis, with the objective of reducing the duration, frequency and severity of symptoms associated with the disorder (e.g., migraine attacks, pain associated with fibromyalgia, etc.). Methods for doing so were disclosed in the co-pending, commonly assigned patent application U.S. Ser. No. 13/109,250, entitled Electrical and magnetic stimulators used to treat migraine/sinus headache and comorbid disorders, to SIMON et al, and U.S. Ser. No. 13/183,721 entitled Electrical and magnetic stimulators used to treat migraine/sinus headache, rhinitis, sinusitis, rhinosinusitis, and comorbid disorders, to SIMON et al. On the other hand, some individuals (the "non-responders") may exhibit no significant changes to the magnitude of features of their evoked potentials following acute stimulation of their vagus nerve. It may be decided on the basis of this outcome that the "non-responders" are candidates for treatment by methods other than performing vagus nerve stimulation on a regular basis [OZKUL Y, Bozlar S. Effects of fluoxetine on habituation of pattern reversal visually evoked potentials in migraine prophylaxis. Headache 42(7,2002):582-587].

Vagus nerve stimulation may also be useful for the treatment of patients irrespective of whether the patient exhibits a deficit in the habituation of evoked potentials, and irrespective of whether the vagus nerve stimulation promotes the normalization of habituation of evoked potentials. In migraineurs, for example, the likely usefulness of the vagus nerve stimulation may more generally be based primarily upon the baseline characteristics of an evoked potential, measured during one or more phases of the migraine headache, particularly during the interictal phase. In fact, it is preferable to perform the measurements during multiple times throughout the interictal phase, in view of the changes in the evoked potential that occur throughout that phase. A method for using previously measured values of characteristics of the baseline evoked potential, to infer the likelihood of therapeutic success, is as follows. If the migraine attack is in progress, noninvasive vagus nerve stimulation is administered, and its effect on the reduction of headache pain is measured. The pain measurement may be based on self-reporting of the patient, or it may be based on an objective physiological measurement of pain. Note that evoked potentials themselves may be correlated with the level of pain and that EEG and autonomic physiological variables collectively (heart rate variability, electrodermal response) may also be measured as being correlated with the level of pain [LI D, Puntillo K, Miaskowski C. A review of objective pain measures for use with critical care adult patients unable to self-report. J Pain 9(2008): 2-10; TOUSIGNANT-Laflamme Y, Rainville P, Marchand S. Establishing a link between heart rate and pain in healthy subjects: a gender effect. J Pain 6(2005): 341-347; NIR R R, Sinai A, Raz E, Sprecher E, Yarnitsky D. Pain assessment by continuous EEG: association between subjective perception of tonic pain and peak frequency of alpha oscillations during stimulation and at rest. Brain Res 1344(2010): 77-86; Tor D. WAGER, Lauren Y. Atlas, Martin A. Lindquist, Mathieu Roy, Choong-Wan Woo and Ethan Kross. An fMRI-Based Neurologic Signature of Physical Pain. N Engl J Med 368(2013):1388-1397].

The measurement of pain may also be made following stimulation with multiple sets of vagus nerve stimulation parameters, in order to evaluate the stimulation parameters that have the greatest effect on the reduction of pain. After vagus nerve stimulation, the evoked potential may be measured again, and the features of the baseline evoked potential may then be compared with features of the post-stimulation evoked potential. Changes in the evoked potential may involve differences in amplitudes and latencies of peaks and troughs, which are of potential predictive value. When such measurements are performed on populations of migraineurs and control normal individuals, statistical methods may then be used to determine which features of the pre- and post-stimulation evoked potentials, as well as their differences, are most closely related to the reduction of pain in the migraineur. The statistical methods may also be used to predict which parameters of the vagus nerve stimulation have the greatest effect on the reduction of pain and on the features of the pre- and post-stimulation evoked potentials. The vagus nerve stimulation may then be re-applied to the patient, with a different set of stimulation parameters, selected on the basis of the relation between those parameters and pain reduction, as well as on characteristics of the pre- and/or post-stimulation evoked potentials.

The vagus nerve stimulation may also be used as a prophylaxis to reduce the frequency or severity of migraine attacks. In that case, the vagus nerve stimulation is applied to the patient over a prolonged period of time, and its quantitative effects on the frequency and severity of the migraine attacks is measured. When such measurements are performed on populations of migraineurs and control normal individuals, statistical methods may then be used to determine which features of the initial pre- and post-stimulation evoked potentials, as well as their differences, are most closely related to reduction in the chronic frequency and severity of migraine attacks. Thereafter, the likelihood that vagus nerve stimulation will be successful in treating a migraineur chronically may be inferred from the measured features of his/her initial pre- and post-stimulation evoked potentials, as well as differences between the pre- and post-stimulation evoked potentials.

Biofeedback Stimulation Protocols

As discussed above in connection with FIG. 1B, devices and methods according to the present invention may involve combined biofeedback and automatic control mechanisms, which begin with measurement of physiological properties of the individual using sensors. One such physiological property is the evoked potential, measured using scalp electrodes. The present invention also contemplates the measurement and processing of many other types of physiological signals, including all of those that have been used in conventional biofeedback experiments. The following are the physiological signals that are nowadays ordinarily used for biofeedback: the EEG (also measured using scalp electrodes, but not time-locked to a stimulus as in an evoked potential measurement), the electromyogram (EMG), the electrodermal response, hand temperature measurements; heart rate variability; and fMRI image features. The use of these and other biofeedback modalities was described in a co-pending, commonly assigned application, entitled Closed-loop, autonomic methods of biofeedback using non-invasive vagus nerve stimulation, to SIMON et al.

In some situations, the relevant features of the evoked potentials may be generated primarily by the central nervous system structures that are involved in conscious neural processing and control. As an example of that situation, the individual may consciously react to the sensations that result from the vagus nerve stimulation, as evidenced by the appearance of a P300 peak in his/her transient evoked potential. After detecting the P300 peak, the device can use that fact to vary the parameters of the next vagus nerve stimulation. For example, the P300 peak may appear once the stimulation amplitude reaches a sensory threshold that is recognized by the subject, or the properties of the P300 peak may change when the stimulation amplitude is so large that it produces pain.

The system shown in FIG. 1B may also be used to train an individual to consciously and voluntarily control the "other physiological system" that is labeled in the figure. In such a biofeedback application, the skin at the subject's neck is stimulated in proportion to a previous or concurrently measured property of the "other physiological system" (e.g., electrodermal voltage measured on the subject's hand), such that the subject is made consciously aware of the magnitude of the measured physiological property through the magnitude of the skin stimulation. Alternatively, the stimulation applied to the subject's neck is a function of the features of the measured evoked potential (e.g., amplitude or latency of one or more particular EP waveform peaks or troughs). The subject then attempts to mentally control the magnitude of the skin stimulation, and thereby consciously control the magnitude of the measured physiological property through thought alone. The electrical signals that simulate cutaneous nerves within the skin may be analog signals that vary in some continuous way relative to the physiological property that is being transduced. Alternatively, the biofeedback signals may be digital, comprising recognizable coded pulse trains, as has been suggested in connection with tactile communication devices for the blind. For example, electrocutaneous signals with three discrete intensity levels and three discrete long-pulse durations can be discriminated [R. H. GIBSON. Electrical stimulation of pain and touch. pp. 223-261. In: D. R. Kenshalo, ed. The Skin Senses. Springfield, Ill.: Charles C Thomas, 1968; Erich A. PFEIFFER. Electrical stimulation of sensory nerves with skin electrodes for research, diagnosis, communication and behavioral conditioning: A survey. Medical and Biological Engineering. 6(6,1968):637-651; Alejandro HERNANDEZ-ARIETA, Hiroshi Yokoi, Takashi Ohnishi, Tamio Arai. An f-MRI study of an EMG Prosthetic Hand Biofeedback System. In: T. Arai et al. (Eds.). IAS-9, Proceedings of the 9th International Conference on Intelligent Autonomous Systems, University of Tokyo, Tokyo, Japan, Mar. 7-9, 2006, Amsterdam: IOS Press, 2006, pp. 921-929; Kahori KITA, Kotaro Takeda, Rieko Osu, Sachiko Sakata, Yohei Otaka, Junichi Ushiba. A Sensory feedback system utilizing cutaneous electrical stimulation for stroke patients with sensory loss. Proc. 2011 IEEE International Conference on Rehabilitation Robotics, Zurich, Switzerland, Jun. 29-Jul. 1, 2011, 2011:5975489, pp 1-6].

Methods for treating and training a patient according to the present invention comprise stimulating the vagus nerve as indicated in FIGS. 1B, 7 and 8, using the electrical stimulation devices and stimulation waveforms that are disclosed here, such as those in FIG. 11. Stimulation may be performed on the left or right vagus nerve, or on both of them simultaneously or alternately. The position and angular orientation of the device are adjusted at the preferred location on the neck, above the vagus nerve, until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. The correctness of the location of the stimulator on the patient's neck may be verified by any of the methods disclosed in the co-pending, commonly assigned application U.S. Ser. No. 13/872,116, entitled DEVICES AND METHODS FOR MONITORING NON-INVASIVE VAGUS NERVE STIMULATION, to SIMON et al., which is incorporated by reference]. Straps, harnesses, or frames may then be used to maintain the stimulator in position (see FIG. 8).

Physiological sensors will have been attached to the patient, and the corresponding physiological measurements will then be made continuously, as described above. Ordinarily, one of those physiological signals will be used to construct a biofeedback signal that is applied electrically to the skin of the patient's neck. The appropriate range of that electrocutaneous biofeedback signal will then be determined as described in the section above entitled "Selection of the electrical stimulation waveform," with the vagus nerve stimulation reduced to an amplitude that is not sufficient to materially stimulate the vagus nerve. Other biofeedback signal modalities could be used too, such as an audio or visual biofeedback signal, but they are not used in the basic invention.

At this point, the patient will attempt to use biofeedback to modify the relevant physiological signal, or will be trained to do so. For example, the physiological signal could be an electrodermal sensor for measuring galvanic skin response, a thermometer for measuring finger temperature and the associated blood flow, or an EEG-derived signal. Strategies for voluntarily modulating the biofeedback signal include deliberately entering a particular emotional state or relaxing muscles. The invention is intended to work with any of the biofeedback signals that have been described in literature that is cited herein, and the intended biomedical applications of such published biofeedback methods apply as well to the present invention.

According to one view, individuals who learn to perform biofeedback do so through a type of neural natural selection, in which pre-existing, randomly-activated efferent neural circuit paths are consciously selected, and the pool of possible circuit paths is measured by the person-to-person lability of the corresponding physiological variable. According to this view, an individual with little lability will have few circuit paths from which to select, and will therefore be disadvantaged in terms of his or her potential to learn biofeedback skills. That is to say, by measuring the natural, unprovoked physiological variability in the physiological signal that is used for biofeedback, i.e., the magnitude of apparent "noise" in the signal about a baseline, one might be able to infer the likelihood that the individual will be able to learn to perform biofeedback [R. Sergio GUGLIELMI and Alan H. Roberts. Volitional vasomotor lability and vasomotor control. Biological Psychology 39(1994):29-44].

This view is sometimes referred to as an efferent or so-called "feedforward" mechanism of biofeedback learning. Note that use of the term "feedforward" in this sense refers to the efferent direction and has nothing to do with the above-mentioned use of the term "feedforward" in engineering control theory. According to the present invention, if the vagus nerve is even stimulated with a sequence of randomly selected stimulation parameters so as to indirectly and artificially increase the lability of the physiological signal, this alone may increase the likelihood that the patient may learn to perform biofeedback [Thomas G. DUNN, Scott E. Gillig, Sharon E. Ponsor, Nolan Weil, and Sharon Williams Utz. The learning process in biofeedback: is it feedforward or feedback? Biofeedback and Self-Regulation 11(2,1986): 143-156; Sharon Williams UTZ. The effect of instructions on cognitive strategies and performance in biofeedback. Journal of Behavioral Medicine 17(3, 1994):291-308; J. M. LACROIX. The acquisition of autonomic control through biofeedback: the case against an afferent process and a two-process alternative. Psychophysiology 18(5,1981):573-587].

An alternate, and not mutually exclusive, view of biofeedback learning is that the acquisition of voluntary visceral control is dependent upon the ability to perceive or discriminate changes in visceral function. According to this view, biofeedback enhances discrimination of interoceptive events by providing additional exteroceptive cues. Thus, the individual must learn to discriminate interoceptive cues related to the target response and to develop skills so as to attain control of the response, including possibly the development of new sensory abilities during the training process. This view of biofeedback learning is sometimes known as an "afferent" mechanism, to distinguish it from the "efferent" mechanism described in the previous paragraph.

The present invention provides another mechanism whereby such discrimination can occur. Instead of, or in addition to, providing the additional exeroceptive cues, the present invention is novel in that it provides additional interoceptive clues. Interoceptive cues are included in those provided by "Other Sense Organs" of FIG. 1B. However, in the present context we refer not to such naturally occurring interoceptive signals, but instead to interoceptive signals that are produced artificially as a result of the vagus nerve stimulation. They correspond to the stimulation of afferent vagus nerve fibers that convey a sense of their excitation to regions of the brain that could result in the conscious but artificial awareness of the viscera, particularly the anterior insula (see FIG. 12) [CRITCHLEY H D, Wiens S, Rotshtein P, Ohman A, Dolan R J. Neural systems supporting interoceptive awareness. Nat Neurosci 7(2,2004):189-195; CRAIG, A. D. How do you feel? Introception: the sense of the physiological condition of the body. Nat. Rev. Neurosci 3(2002):655-666; CRAIG A D. How do you feel—now? The anterior insula and human awareness. Nat Rev Neurosci 10(1,2009):59-70]. In one embodiment, the magnitude of stimulation of those afferent fibers is made to increase or decrease according to the corresponding level of the physiological signal that is being sensed. One may regard that method as a type of augmented biofeedback that involves interoceptive sensation, rather than exteroceptive sensation. This stimulation of afferent vagal nerve fibers is also intended to simulate the adaptation of interoceptors that may be required for the direct, voluntary control of the viscera [Barry R. DWORKIN. Learning and Physiological Regulation. Chicago: University of Chicago Press, 1993, Chapter 8, pp. 162-185].

After determining whether and to what extent the patient is able to consciously control the biofeedback signal, biofeedback will be suspended and the parameters suitable for vagus nerve stimulation will then be determined. Ordinarily, the amplitude of the stimulation signal is set to the maximum that is comfortable for the patient, and then the other stimulation parameters are adjusted. In general, the stimulator signal may have a frequency and other parameters that are selected to produce a therapeutic result in the patient, i.e., stimulation parameters for each patient are adjusted on an individualized basis, in order to produce an effect that is relevant to the condition that is being treated. The parameter values may be selected in such a way as to activate or suppress particular resting state networks of the brain that are relevant to the patient's condition, as described in the section above entitled "Selection of stimulation parameters to activate or suppress selected resting state networks of the brain." Preliminary control theory procedures, including tuning and the training of a support vector machine, may also be performed in order to allow the system to vary its stimulation parameters in response to fluctuating environmental and sensed physiological signals, as described in the section "Use of biofeedback and automatic control theory methods to treat and train patients."

A typical stimulation waveform was shown in FIGS. 11B and 11C. As seen there, individual sinusoidal pulses have a period of tau, and a burst consists of N such pulses. This is followed by a period with no signal (the inter-burst period). The pattern of a burst followed by silent inter-burst period repeats itself with a period of T. For example, the sinusoidal period tau may be 200 microseconds; the number of pulses per burst may be N=5; and the whole pattern of burst followed by silent inter-burst period may have a period of T=40000 microseconds, which is comparable to 25 Hz stimulation. More generally, there may be 1 to 20 pulses per burst, preferably five pulses. Each pulse has a duration of 1 to 1000 microseconds (i.e., about 1 to 10 KHz), preferably 200 microseconds (about 5 KHz). A burst followed by a silent inter-burst interval repeats at 1 to 5000 bursts per second (bps), preferably at 5-50 bps, and even more preferably 10-25 bps stimulation (10-25 Hz). The preferred shape of each pulse is a full sinusoidal wave, although triangular or other shapes may be used as well.

Such a signal may be constructed by circuits within the stimulator housing (30 in FIG. 3), or it may be transmitted to the housing using radio transmission from the base station or any of the other components of the control unit (see FIG. 6). Compression of the signal is also possible, by transmitting only the signal parameters tau, N, T, Emax, etc., but in that case, the stimulator housing's control electronics would then have to construct the waveform from the transmitted parameters.

After the cutaneous and deep nerve stimulation waveform parameters have been preliminarily selected, and it has been determined that the patient can perform biofeedback, stimulation sessions can be initiated in which the biofeedback and vagus nerve stimulation are performed simultaneously. The duration of a stimulation session depends on the physiological condition that is being treated, and success of the stimulation may be judged in terms of whether the sensed physiological signal is adjusted by the stimulation to be within a clinically desirable range. Alternatively, other indices of clinical success may be made, depending on the condition that is being treated.

The three mechanisms shown in FIG. 1B (biofeedback, artificial interoceptive sensation, and direct stimulation via the vagus nerve to effect automatic control) will collectively modulate the physiological system, interacting with one another to determine the value of the sensed physiological signal. Part of the interaction is determined by the manner in which the nerve stimulator/biofeedback device/physiological controller is programmed. For example, direct stimulation of the physiological system via the vagus nerve may be programmed to follow and amplify changes that occur as a result of biofeedback. An embodiment of that example would occur when a migraineur uses galvanic skin response biofeedback alone to consciously reduce sympathetic tone through muscular and emotional modulation, whereupon the device senses that reduction through its programming and then amplifies the effect by increasing parasympathetic tone after a brief time delay, by directly stimulating vagal parasympathetic efferent nerve fibers. The present invention may be used to amplify such biofeedback-induced effects by first detecting the patient's attempted muscular relaxation and the associated reduction in sympathetic tone, and by then stimulating the vagus nerve to increase parasympathetic tone.

In migraine patients, biofeedback may also involve an attempt to modulate components of evoked potentials that are related to a particular pathway, generally by decreasing the magnitude of particular peak or troughs that may be associated with pain. The migraine-related pathway involves pre- and postganglionic parasympathetic neurons in the superior salivatory nucleus (SSN) and sphenopalatine ganglion (SPG), respectively. The SSN stimulates the release of acetylcholine, vasopressin intestinal peptide, and nitric oxide from meningeal terminals of SPG neurons, resulting directly or indirectly in the migraine-related cascade of events that include the dilation of intracranial blood vessels, plasma protein extravasation, and local release of inflammatory molecules that activate adjacent terminals of meningeal nociceptors. The SSN receives extensive input from more than fifty brain areas, many of which may be modulated by the locus ceruleus.

When the locus ceruleus is activated through vagus nerve stimulation, it will respond by increasing norepinephrine secretion, which in turn will alter cognitive function through the prefrontal cortex, increase motivation through nucleus accumbens, activate the hypothalamic-pituitary-adrenal axis, and increase the sympathetic discharge/inhibit parasympathetic tone through the brainstem. Such inhibition of parasympathetic tone will specifically inhibit the parasympathetic pathway via the superior salivatory nucleus, thereby blocking the positive feedback loop that contributes to the maintenance of migraine pain [Commonly assigned, co-pending patent application US20110276107, entitled Electrical and magnetic stimulators used to treat migraine/sinus headache, rhinitis, sinusitis, rhinosinusitis, and comorbid disorders, to SIMON et al, which is hereby incorporated by reference].

Minimally Invasive Embodiment of the Vagus Nerve Stimulator

An alternate embodiment of the present invention, involving minimally invasive rather than noninvasive vagus nerve stimulation, is illustrated by FIG. 15. As ordinarily practiced, the electrodes used to stimulate a vagus nerve are implanted about the nerve during open neck surgery. However, in a commonly assigned, copending application, Applicant disclosed that it is also possible to electrically stimulate a vagus nerve using a minimally invasive surgical approach, namely percutaneous nerve stimulation. In that procedure, a pair of electrodes (an active and a return electrode) are introduced through the skin of a patient's neck to the vicinity of a vagus nerve, and wires connected to the electrodes extend out of the patient's skin to a pulse generator [Publication number US20100241188, entitled Percutaneous electrical treatment of tissue, to J. P. ERRICO et al.; SEPULVEDA P, Bohill G, Hoffmann T J. Treatment of asthmatic bronchoconstriction by percutaneous low voltage vagal nerve stimulation: case report. Internet J Asthma Allergy Immunol 7(2009):e1 (pp 1-6); MINER, J. R., Lewis, L. M., Mosnaim, G. S., Varon, J., Theodoro, D. Hoffman, T. J. Feasibility of percutaneous vagus nerve stimulation for the treatment of acute asthma exacerbations. Acad Emerg Med 2012; 19: 421-429].

In the present invention, electrodes are preferably also introduced percutaneously to the vicinity of a vagus nerve, but unlike the previous minimally invasive disclosure, the electrodes are not ultimately connected to wires that extend outside the patient's skin. Instead, in the present invention, the percutaneously implanted stimulator receives energy wirelessly from an external transmitter that need not be in close proximity to the skin of the patient, and electrical pulse generation occurs within the implanted stimulator using that energy.

Figure 15A:
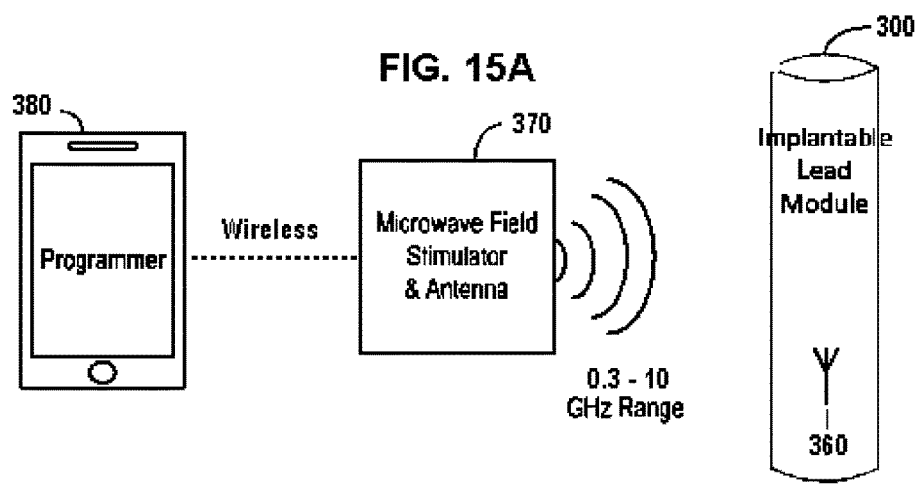
FIGS. 15A-15C illustrate an embodiment of the nerve stimulator, including a schematic view of a nerve modulating system (implantable lead module or electrical stimulator) according to one or more aspects of the present invention (FIG. 15A); a schematic view of an implantable stimulation device according to the present invention (FIG. 15B); and a more specific view (FIG. 15C) of the components of one embodiment of the implantable stimulation device shown in FIG. 15B.

As shown in FIG. 15A, the nerve modulating device 300 of the minimally invasive embodiment of the invention (also known as an implantable lead module or simply an electrical nerve stimulator) is powered by the receipt of far-field or approximately plane wave electromagnetic energy with frequencies in the range of 0.3 to 10 GHz (preferably about 800 MHz to about 6 GHz, and more preferably about 800 MHz to about 1.2 MHz) which is received wirelessly by an antenna 360 within, or attached to, the device 300. The energy that powers the nerve modulating device 300 is transmitted by an external device, which in FIG. 15A is labeled as a Controller 370. Controller 370 is in turn controlled by a programmer device 380, which preferably communicates with controller 370 wirelessly. In operation, the nerve modulating device 300 is implanted within the patient, the controller 370 may be either outside of the patient or implanted within the patient, and the programmer 380 is operated manually by the patient or a caregiver. The antenna of the controller 370 is actively tuned/matched to the resonant frequency of an antenna in the implanted device 300 so that the maximum efficiency of power transmission is achieved. There may be several antennae at various orientations in the external unit and/or in the implanted signal generator to enhance coupling efficiency in various orientations. The unit 370 supplying power and control to the implanted device 300 could be AC powered and/or battery powered. If powered by rechargeable batteries, a battery charger may be an accessory to the system. The controller 370 is preferably both portable and rechargeable. In one embodiment, it may be worn around the neck as a pendant, placed in a pocket, or clipped to clothing. This wireless transmitter 370 is preferably recharged at a recharging base and has a significant range of transmission, preferably up to four feet, so that patients can sleep without having to wear the transmitter.

Figure 15B:
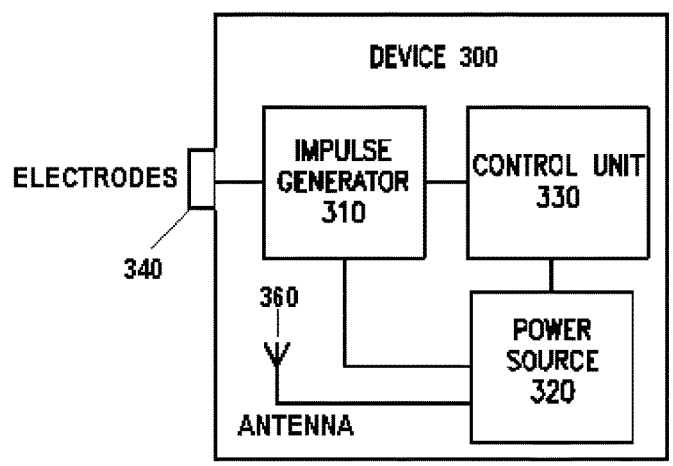

FIG. 15B is a more detailed schematic diagram of the nerve modulating device 300 for delivering electrical impulses to nerves. As shown, device 300 comprises an electrical impulse generator 310; a power source 320 coupled to the electrical impulse generator 310; a control unit 330 in communication with the electrical impulse generator 310 and coupled to the power source 320; and one or more electrodes 340 coupled to the electrical impulse generator 310. Nerve modulating device 300 is configured to generate electrical impulses sufficient to modulate the activity of one or more selected regions of a nerve (not shown). The power source 320 receives energy wirelessly via an antenna 360, wherein the energy is in the form of far-field or approximately plane-wave electromagnetic waves with frequencies in the range of 0.3 to 10 GHz, preferably about 800 MHz to about 1.2 MHz.

The control unit 330 may control the electrical impulse generator 310 for generation of a signal suitable for amelioration of a patient's condition when the signal is applied via the electrodes 340 to the nerve. It is noted that nerve modulating device 300 excluding the electrodes 340 may be referred to by its function as a pulse generator. U.S. Patent Application Publications 2005/0075701 and 2005/0075702, both to SHAFER, both of which are incorporated herein by reference, relating to stimulation of neurons of the sympathetic nervous system to attenuate an immune response, contain descriptions of pulse generators that may be applicable to various embodiments of the present invention.

Figure 15C:
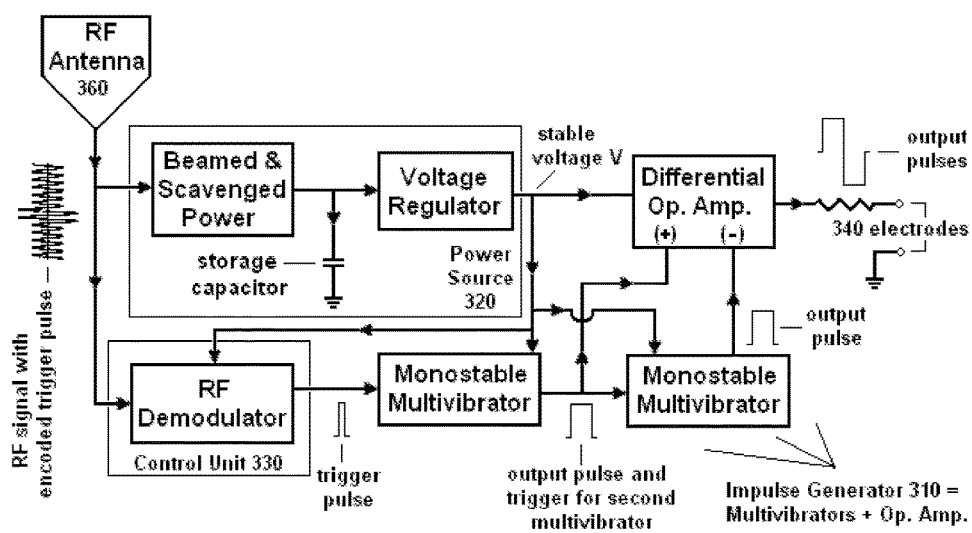

FIG. 15C illustrates one embodiment of the nerve modulating device 300 that consumes relatively little power and may therefore receive power from a correspondingly weak and/or distant external transmitter. To achieve low power consumption, the embodiment is designed to use a minimum of components. This may be accomplished by designing the device to produce constant voltage pulses, rather than constant current pulses, because circuits for the latter are more complex and consume more power than the former. However, for some patients a constant current pulse may be preferred, depending on the detailed anatomy of the patient's neck in the vicinity of the stimulated nerve (see below). Consequently, constant current pulses are also contemplated by the invention [DELIMA, J. A. and Cordeiro, A. S. A simple constant-current neural stimulator with accurate pulse-amplitude control. Engineering in Medicine and Biology Society, 2001. Proceedings of the 23rd Annual International Conference of the IEEE (Vol. 2, 2001) 1328-1331]. In either case, simplicity of circuit design is provided by a design that makes the amplitude of the pulse constant, rather than by allowing the amplitude to be variable. Accordingly, the present invention modulates the stimulation power to the nerve by altering the number and timing of the pulses, rather than by modulating the amplitude of individual pulses. Additional simplicity of design may be achieved by using communication that occurs in one direction only, from the transmitter to the stimulator (simplex communication according to the ANSI definition, rather than half or full duplex communication).

The stimulator circuit is novel in that it removes one (or more) elements from conventional stimulators, without sacrificing performance. In particular, the present invention removes from conventional designs the ability of the stimulator to vary the amplitude of the stimulation pulses. Unexpectedly, one can get substantially the same stimulatory effect as that provided by conventional stimulators, by keeping waveform parameters fixed, particularly the amplitude of pulses, but by then controlling the number and timing of pulses that the nerve experiences, in order to achieve the same physiologically desirable level of nerve stimulation. In essence, this invention uses an adjustable number of fixed voltage (or fixed current) pulses with fixed duration to elicit desired changes in nerve response. These fixed voltage pulses create one long continuous pulse to the nerve to ensure that sufficient energy is delivered to the nerve to cause the nerve to reach its action potential and fire. Thus, the present invention reaches the threshold energy level for a nerve to fire by adjusting the duration of the pulse received by the nerve, rather than adjusting the amplitude of the pulse.

In another aspect of the invention, the specific number of fixed amplitude pulses that will be delivered to the nerve is preferably determined through an iterative process with each patient. Once the surgeon determines the number of fixed voltage pulses required to stimulate the nerve for a particular patient, this number is programmed into either the external controller or the implantable stimulator.

A constant-voltage pulse design teaches against prevailing preferred designs for vagus nerve stimulators. Thus, constant-voltage pulses are used in cardiac pacemakers, deep brain stimulation, and some implantable neuromodulators for treatment of incontinence and chronic pain, but constant-current pulses are used for cochlear implants and vagus nerve stimulators [D. PRUTCHI and M. Norris Stimulation of excitable tissues. Chapter 7, pp. 305-368. In: Design and development of medical electronic instrumentation. Hoboken: John Wiley & Sons, 2005]. In the latter applications, the constant current design is said to be preferred because slight variations in stimulator-to-nerve distance change the ability of the constant-voltage pulse stimulator to depolarize the nerve, which is less of a problem with constant-current pulse stimulators. With the constant current design, the stimulation thresholds stay more or less constant even with changing electrode impedance and ingrowth of tissue into the neural interface [Emarit RANU. Electronics. Chapter 10, pp. 213-243. In: Jeffrey E. Arle, Jay L. Shils (eds). Essential Neuromodulation. Amsterdam, Boston: Academic Press. 2011]. For example, the BION stimulators described in the background section of the present application generate only constant current pulses.

In some embodiments of the present invention, a constant voltage pulse is used because it can be produced with a simpler circuit that consumes less power, as compared with constant pulse current circuits. The above-mentioned potential problem with variation in stimulator-to-nerve distance is addressed by anchoring the stimulator to the vagus nerve. Furthermore, the problem may be circumvented to some extent in the present invention by coating the stimulator's electrodes with a very thin layer of poorly conducting material. This is because the presence of a poorly conducting boundary layer surrounding the stimulator minimizes the differential effects of conductivity variations and electrode location during constant current and constant voltage stimulation [Mark M. STECKER. Nerve stimulation with an electrode of finite size: differences between constant current and constant voltage stimulation. Computers in Biology and Medicine 34(2004):51-94].

Additional circuit simplicity and minimized power requirements are accomplished in the embodiment shown in FIG. 15C by fixing the characteristics of the stimulation pulses, rather than by adding circuits that would allow the characteristics to be adjusted through use of external control signals. For example, the output pulses shown in FIG. 15C are shown to be generated using a pair of monostable multivibrators. The first multivibrator receives a trigger pulse from the control unit 330, resulting in a pulse of fixed duration. The second multivibrator is triggered by the falling edge of the first multivibrator's pulse, and the pair of pulses from the two multivibrators are combined with suitable polarity using a differential operational amplifier. Thus, in this example, the impulse generator 310 consists of the multivibrators and operational amplifier. The amplifier in turn presents the stimulation pulses to the electrodes 340. The time period that a monostable multivibrator remains in its unstable state (the pulse width) is a function of its component resistor and capacitor values, so if the pulse width can be preselected for a patient, the device can be designed using correspondingly fixed R and C values. On the other hand, if a variable pulse width is needed during preliminary testing with a patient, the multivibrator circuit can be made more complex, with the pulse width selected on the basis of coded signals that are transmitted to the impulse generator 310 via the control unit 330. Once the appropriate pulse width has been selected, a control signal may be sent from the control unit 330 to disable extraneous power consumption by the variable pulse-width circuitry. Proper pulse width is particularly important in stimulating nerve fibers having the appropriate diameters [see discussion below and SZLAVIK R B, de Bruin H. The effect of stimulus current pulse width on nerve fiber size recruitment patterns. Med Eng Phys 21(6-7,1999):507-515].

It is also understood that more complex pulses may also be preferred, which would require a correspondingly more complex circuitry and possibly additional power consumption, as compared with the circuit shown in FIG. 15C [JEZERNIK S, Morari M. Energy-optimal electrical excitation of nerve fibers. IEEE Trans Biomed Eng 52(4,2005): 740-743; Wongsarnpigoon A, Woock J P, Grill W M. Efficiency analysis of waveform shape for electrical excitation of nerve fibers. IEEE Trans Neural Syst Rehabil Eng 18(3, 2010):319-328; FOUTZ T J, Ackermann D M Jr, Kilgore K L, McIntyre C C (2012) Energy efficient neural stimulation: coupling circuit design and membrane biophysics. PLoSONE 7(12): e51901. doi:10.1371/journal-.pone.0051901, pp. 1-8; McLEOD K J, Lovely D F, Scott R N. A biphasic pulse burst generator for afferent nerve stimulation. Med Biol Eng Comput 25(1,1987):77-80].

The control unit 330 in FIG. 15C is shown to exercise its control only by presenting trigger pulses to the impulse generator 310. In this example, the train of pulses appearing across the electrodes 340 is determined only by the timing of the sequence of trigger pulses. The trigger pulses are themselves encoded in the signal that is transmitted from controller 370 in FIG. 15A, shown in FIG. 15C as "RF signal with encoded trigger pulse." The trigger pulses are extracted and reconstructed from the transmitted signal by an RF demodulator in the control unit 330. There are many methods for transmitting and decoding such control signals, and the present invention may be designed to use any of them [Robert PUERS and Jef Thoné. Short distance wireless communications. Chapter 7, pp. 219-277, In: H.-J. Yoo, C. van Hoof (eds.), Bio-Medical CMOS ICs. New York: Springer, 2011]. Because the timing of pulses is determined by the trigger pulses emanating from the transmitted signal, the circuit shown in FIG. 15C does not even need a clock, thereby reducing its power requirements. However, in other embodiments a clock may be included as part of the timing circuitry. It is understood that in order to command a pulse of the treatment signal and switch that pulse to the electrodes, it is possible to use a control RF signal having a different frequency than the one used to provide power, or encode the command based on variation in the RF signal's amplitude, pulse width and/or duration.

The transmitted RF signal is received by an antenna 360, and the signal provides power for the stimulation device 300, in addition to the control signals. The power is provided by the power source 320 in FIG. 15C. As shown there, energy from the transmitted RF signal (beamed power) is accumulated in a storage capacitor, which is eventually discharged in conjunction with the creation of stimulation pulses that are applied to the electrodes 340. In addition to the beamed power, there may also be scavenged power, which arises from the reception of ambient electromagnetic radiation by the antenna 360. Special circuits and antennas may be used to scavenge such ambient electromagnetic radiation [Soheil RADIOM, Majid Baghaei-Nejad, Guy Vandenbosch, Li-Rong Zheng, Georges Gielen. Far-field RF Powering System for RFID and Implantable Devices with Monolithically Integrated On-Chip Antenna. In: Proc. Radio Frequency Integrated Circuits Symposium (RFIC), 2010 IEEE, Anaheim, Calif., 23-25 May 2010, pp. 113-116]. Power scavenging may be most appropriate in a hospital setting where there is significant ambient electromagnetic radiation, due to the use there of diathermy units and the like [FLODERUS B, Stenlund C, Carlgren F. Occupational exposures to high frequency electromagnetic fields in the intermediate range (>300 Hz-10 MHz). Bioelectromagnetics 23(8,2002):568-577].

The stimulator circuit comprises either a battery or a storage device, such as a capacitor, for storing energy or charge and then delivering that charge to the circuit to enable the circuit to generate the electrical impulses and deliver those impulses to the electrodes. The energy for the storage device is preferably wirelessly transmitted to the stimulator circuit through a carrier signal from the external controller. In the preferred embodiments, the energy is delivered to the energy storage device between electrical impulses. Thus, the energy is not being delivered in "real-time", but during the periods when the pulse is not being delivered to the nerve or during the refractory period of the nerve. For example, a typical electrical impulse may be ON for about 200 uS and then OFF for about 39,000 uS. The energy is delivered during this longer OFF time, which enables the system to use a much smaller signal from the external generator. The external generator delivers the carrier signal over the OFF period to charge the energy storage device, which then releases this energy or charge to the remainder of the circuit to deliver the electrical impulse during the 200 uS ON time.

Transmitting energy to the storage device in between the electrical impulses provides a number of advantages. First, it increases the length of time that the electrical energy can be delivered to charge the storage device. This reduces the strength of the signal required to deliver the electrical energy to the storage device, thereby reducing the overall power requirements of the external controller and reducing the complexity of the stimulator circuitry. In addition, it enhances the safety of the device because it reduces the risk that uncontrolled environmental RF energy will create an electrical connection between the nerve and the charged energy. Since the storage device is receiving electrical energy between electrical impulses, there is no electrical connection between the stimulator circuit and the nerve as the storage device is charged. This reduces the risk of the electrical energy being accidently applied to the nerve.

In order to power the impulse generator and demodulation circuits, the power source 320 in FIG. 15C makes use of a voltage regulator, the output from which is a stable voltage V. The circuits that may be selected for the voltage regulator comprise those described by BOYLESTAD [Robert L BOYLESTAD and Louis Nashelsky. Power Supplies (Voltage Regulators). Chapter 18, pp. 859-888. In: Electronic devices and circuit theory, 8th ed. Upper Saddle River, N.J.: Prentice Hall, 2002].

In preferred embodiments of the minimally invasive stimulator, the parameters of fixed stimulation pulses are generally as follows. The shape of the pulse is square, sine, triangular or trapezoidal with negative voltage return to eliminate DC bias. The electrical impulse will typically have a frequency of between about 1-500 Hz, preferably about 1 to 50 Hz, and more preferably about 10-35 Hz. In an exemplary embodiment, the frequency for the impulse received by the nerve is about 25 Hz. The preferred fixed voltage received by the nerve is between about 1-20 V and will typically vary depending on the size and type of electrode and the distance between the electrode and the nerve. In certain embodiments where the nerve is directly attached to the nerve (or implanted adjacent to the nerve), the fixed voltage is preferably about 1 to 4 volts, more preferably about 2 volts. In other embodiments, wherein the electrode is, for example, injected into the patient and implanted outside of the sheath, the voltage is preferably between about 7-15 volts and more preferably about 10 V. In embodiments wherein the current is fixed or held constant, the preferred fixed current is about 0.5 mA to about 20 mA. Similar to voltage, the fixed current will vary depending on the size and type of electrode and its distance from the nerve. In those embodiments where the electrode is adjacent to, or on, the nerve, the current is preferably about 0.5 to 5 mA and more preferably about 3.5 mA. In those embodiments, where the electrode is spaced from the nerve (just as an injectable electrode outside of the sheath), the current is preferably about 7-15 mA and more preferably about 10 mA. The pulse duration is preferably between about 50 to 1000 uS.

Benefits of the disclosed system include the following features. The implanted signal generator can be much smaller than a traditional implanted generator. The surgery to implant this system can be done under local anesthesia on an outpatient basis in a non-hospital setting resulting in faster recovery and less scarring. Furthermore, since there is no implanted battery, the patient does not need additional surgeries to replace batteries, which is especially important if the patient has a treatment protocol that requires treatments involving significant power and duration. Also, the limited circuitry implanted in the body will be more reliable than traditional implanted generators. Because the treatment is powered and controlled from outside the body, changes to the treatment protocol can be made quickly and easily. In the event of an emergency, the patient or caregiver can quickly turn-off or remove the power/control unit to stop treatment.

The stimulator circuit is novel in that it removes one (or more) elements from conventional stimulators, without sacrificing performance. In particular, the present invention removes from conventional designs the ability of the stimulator to vary the amplitude of the stimulation pulses. Unexpectedly, one can get substantially the same stimulatory effect as that provided by conventional stimulators, by keeping waveform parameters fixed, particularly the amplitude of pulses, but by then controlling the number and timing of pulses that the nerve experiences, in order to achieve the same physiologically desirable level of nerve stimulation. In essence, this invention is using an adjustable number of fixed voltage (or current) pulses with fixed duration to elicit desired changes in nerve response.

The electrode and signal generator are primarily, but not exclusively, intended for stimulation of the vagus nerve in the neck, for conditions that include headache and fibromyalgia. In those applications, the typical signal would be square or sine pulses of fixed amplitude approximately 2 Volts, where each pulse has a fixed duration of 200 uS. Typically 5 of these pulses would be produced every 40 mS to produce an effective 25 Hz signal.

Although the preferred embodiments of the invention are as described above, it is understood that one may also modify the capabilities of the device as follows. Optionally, the pulse command could have an address or other identifier associated with it so that only a particular signal generator would be activated. This would allow a patient to have multiple implanted signal generators in the body with each responding to its own command from the same or multiple power/control units. Another option would be to have circuitry or a processor in the implanted signal generator that could communicate a signal back to the power/control unit. This signal could contain status information such as voltage, current, number of pulses applied or other applicable data. The antennae and RF signals in this system could also be replaced by closely coupled coils of wire and lower frequency signals that are inductively coupled through the body.

For such minimally invasive stimulators, the cutaneous (e.g. tactile) stimulation shown in FIG. 1B is not feasible unless additional skin-surface electrodes were to be applied to the subject. Nevertheless, in such applications, the individual may also consciously respond to the artificial interoceptive signals that are applied through the minimally invasive vagus nerve stimulator, as though they were a biofeedback signal. Otherwise, the biofeedback methods that are disclosed herein would have to be performed using sensory modalities that do not involve cervical electrical stimulation, for example, by using auditory or visual biofeedback that is produced through the "Other Sensory Stimuli" component of FIG. 1B.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for treating a medical condition in a patient, the method comprising:
    applying a first sensory stimulus to the patient;
    measuring a first baseline evoked potential from the patient, wherein the first baseline potential is evoked by the first sensory stimulus;
    applying an electrical impulse transcutaneously through an outer skin surface of the patient to a vagus nerve of the patient;
    measuring a second evoked potential from the patient subsequent to the applying, wherein the second evoked potential relates to a response of the patient to the medical condition as a function of a characteristic of the electrical impulse;
    comparing a characteristic of the first baseline evoked potential with a characteristic of the second evoked potential; and
    determining, based on the comparing, whether the electrical impulse has triggered an action potential in the vagus nerve.

2. The method of claim 1, further comprising:
    varying an amplitude of the electrical impulse based on the comparing.

3. The method of claim 1, further comprising:
    varying a frequency of the electrical impulse based on the comparing.

4. The method of claim 1, wherein the applying comprises positioning an electrode in contact with the outer skin surface.

5. The method of claim 4, further comprising:
    varying a position of the electrode on the outer skin surface based on the comparing.

6. The method of claim 4, further comprising:
    varying an orientation of the electrode on the outer skin surface based on the comparing.

7. The method of claim 1, wherein the measuring comprises positioning an electrode on a scalp of the patient and measuring a voltage fluctuation arising from an ionic current within a brain of the patient.

8. The method of claim 1, further comprising:
    measuring an acute response of the patient to the medical condition as a function of a characteristic of the electrical impulse; and
    comparing the acute response with the first baseline evoked potential and the second evoked potential.

9. The method of claim 8, wherein the acute response comprises a reduction in pain.

10. The method of claim 1, wherein the sensory stimulus comprises at least one of a visual stimulus, an auditory stimulus, a somatosensory stimulus, a painful stimulus, an olfactory stimulus, a gustatory stimulus, a vestibular stimulus, or an interoceptive stimulus.

11. The method of claim 1, wherein the action potential in the vagus nerve is associated with an increase in a habituation of the second evoked potential compared to a habituation of the first baseline evoked potential.

12. The method of claim 1, wherein the action potential in the vagus nerve is associated with a deficit in a habituation of the second evoked potential compared to a habituation of the first baseline evoked potential.

13. The method of claim 1, wherein the medical condition comprises a primary headache.

14. A method for treating a medical condition in a patient, the method comprising:
    applying a first sensory stimulus to the patient;
    measuring a first baseline electrical potential from the patient, wherein the first baseline electrical potential is evoked by the first sensory stimulus;
    applying an electrical impulse transcutaneously through an outer skin surface of a neck of the patient to a vagus nerve of the patient;
    measuring an acute response of the patient to the medical condition as a function of a characteristic of the electrical impulse; and
    comparing the acute response with the first baseline electrical potential.

15. The method of claim 14, further comprising varying an amplitude of the electrical impulse based on the comparing.

16. The method of claim 14 further comprising varying a frequency of the electrical impulse based on the comparing.

17. The method of claim 14 wherein the applying comprises positioning an electrode in contact with the outer skin surface.

18. The method of claim 17 further comprising varying a position of the electrode on the outer skin surface based on the comparing.

19. The method of claim 17 further comprising varying an orientation of the electrode on the outer skin surface based on the comparing.

20. The method of claim 14 wherein the first sensory stimulus comprises at least one of a visual stimulus, an auditory stimulus, a somatosensory stimulus, a painful stimulus, an olfactory stimulus, a gustatory stimulus, a vestibular stimulus, or an interoceptive stimulus.

21. The method of claim 14 further comprising determining, based on the comparing, whether the electrical impulse has triggered an action potential in the vagus nerve.

22. The method of claim 21 wherein the action potential in the vagus nerve is associated with an increase in a habituation of the acute response compared to a habituation of the first baseline electrical potential.

23. The method of claim 21 wherein the action potential in the vagus nerve is associated with a deficit in a habituation of the acute response compared to a habituation of the first baseline electrical potential.

24. The method of claim 14 wherein the medical condition comprises a primary headache.

25. The method of claim 24 wherein the acute response is a reduction in pain.

26. A method comprising:
measuring a first evoked potential from a patient having an outer skin surface and a vagus nerve, wherein the first evoked potential has a first characteristic and was evoked via a first sensory stimulus applied to the patient; applying an electrical impulse transcutaneously through the outer skin surface to the vagus nerve after the first evoked potential has been measured; measuring a second evoked potential from the patient responsive to the electrical impulse being applied, wherein the second evoked potential has a second characteristic, performing a comparison between the first characteristic and the second characteristic; and taking an action based on the comparison being informative of the electrical impulse causing a response in the patient.

27. The method of claim 26, wherein the electrical impulse causes an action potential in the vagus nerve.

\* \* \* \* \*